US012577530B2

(12) United States Patent
Butts et al.

(10) Patent No.: US 12,577,530 B2
(45) Date of Patent: Mar. 17, 2026

(54) GENERATION OF A POPULATION OF HINDBRAIN CELLS AND HINDBRAIN-LIKE ORGANOIDS FROM PLURIPOTENT STEM CELLS

(71) Applicants: The Regents of the University of California, Oakland, CA (US); The J. David Gladstone Institutes, a testamentary trust established under the Will of J. David Gladstone, San Francisco, CA (US)

(72) Inventors: Jessica C. Butts, San Francisco, CA (US); Todd C. McDevitt, San Francisco, CA (US)

(73) Assignees: The J. David Gladstone Institutes, a testamentary trust established under the Will of J. David Gladstone, San Francisco, CA (US); The Regents of the University of California, Oakland, CA (US)

( * ) Notice: Subject to any disclaimer, the term of this patent is extended or adjusted under 35 U.S.C. 154(b) by 905 days.

(21) Appl. No.: 17/254,263

(22) PCT Filed: Jun. 13, 2019

(86) PCT No.: PCT/US2019/036990
§ 371 (c)(1),
(2) Date: Dec. 19, 2020

(87) PCT Pub. No.: WO2019/245859
PCT Pub. Date: Dec. 26, 2019

(65) Prior Publication Data
US 2021/0284962 A1     Sep. 16, 2021

Related U.S. Application Data

(60) Provisional application No. 62/688,236, filed on Jun. 21, 2018.

(51) Int. Cl.
| | |
|---|---|
| *C12N 5/0793* | (2010.01) |
| *A01K 67/0271* | (2024.01) |
| *B01J 23/50* | (2006.01) |
| *B01J 27/224* | (2006.01) |
| *B01J 35/61* | (2024.01) |
| *B01J 35/63* | (2024.01) |
| *B01J 37/02* | (2006.01) |
| *B01J 37/08* | (2006.01) |
| *C07C 5/333* | (2006.01) |
| *C07D 301/06* | (2006.01) |
| *C10G 11/02* | (2006.01) |
| *C10G 45/04* | (2006.01) |
| *C10G 47/02* | (2006.01) |
| *B01J 35/40* | (2024.01) |
| *B01J 35/45* | (2024.01) |

(52) U.S. Cl.
CPC ........ *C12N 5/0619* (2013.01); *A01K 67/0271* (2013.01); *B01J 23/50* (2013.01); *B01J 27/224* (2013.01); *B01J 35/612* (2024.01); *B01J 35/613* (2024.01); *B01J 35/633* (2024.01); *B01J 35/635* (2024.01); *B01J 37/0203* (2013.01); *B01J 37/08* (2013.01); *C07C 5/3335* (2013.01); *C07D 301/06* (2013.01); *C10G 11/02* (2013.01); *C10G 45/04* (2013.01); *C10G 47/02* (2013.01); *A01K 2207/12* (2013.01); *A01K 2227/105* (2013.01); *A01K 2227/106* (2013.01); *B01J 35/40* (2024.01); *B01J 35/45* (2024.01); *C07C 2521/08* (2013.01); *C07C 2521/18* (2013.01); *C07C 2523/50* (2013.01); *C10G 2300/202* (2013.01); *C10G 2300/207* (2013.01); *C12N 2501/105* (2013.01); *C12N 2501/13* (2013.01); *C12N 2501/15* (2013.01); *C12N 2501/385* (2013.01); *C12N 2501/41* (2013.01); *C12N 2501/415* (2013.01); *C12N 2501/42* (2013.01); *C12N 2501/727* (2013.01); *C12N 2501/999* (2013.01); *C12N 2506/02* (2013.01); *C12N 2506/45* (2013.01); *C12N 2513/00* (2013.01); *C12N 2533/90* (2013.01); *C12N 2535/00* (2013.01)

(58) Field of Classification Search
None
See application file for complete search history.

(56) References Cited

FOREIGN PATENT DOCUMENTS

| | | | |
|---|---|---|---|
| WO | WO-2014153230 A1 | 9/2014 | |
| WO | WO-2017123791 A1 | 7/2017 | |
| WO | WO-2017210138 A1 * | 12/2017 | ........... A01K 67/027 |
| WO | WO-2019245859 A1 | 12/2019 | |

OTHER PUBLICATIONS

Brown, Chelsea R., et al. "Generation of V2a interneurons from mouse embryonic stem cells." Stem Cells and Development 23.15 (2014): 1765-1776. (Year: 2014).*
Inestrosa, Nibaldo C., and Lorena Varela-Nallar. "Wnt signalling in neuronal differentiation and development." Cell and tissue research 359 (2015): 215-223. (Year: 2015).*
Esfandiari, Fereshteh, et al. "Glycogen synthase kinase-3 inhibition promotes proliferation and neuronal differentiation of human-induced pluripotent stem cell-derived neural progenitors." Stem cells and development 21.17 (2012): 3233-3243. (Year: 2012).*
Jia, Xu-feng, et al. "ROCK inhibition enhances neurite outgrowth in neural stem cells by upregulating YAP expression in vitro." Neural regeneration research 11.6 (2016): 983. (Year: 2016).*

(Continued)

*Primary Examiner* — Kara D Johnson
*Assistant Examiner* — Constantina E Stavrou
(74) *Attorney, Agent, or Firm* — Schwegman Lundberg & Woessner, P.A.

(57) ABSTRACT

Provided herein are methods of generating hindbrain cells, including respiratory hindbrain cells, from pluripotent stem cells. Also provided are methods of generating a three-dimensional organoid comprising a population of hindbrain cells including a heterogeneous population of interneurons.

33 Claims, 78 Drawing Sheets

(56)            References Cited

OTHER PUBLICATIONS

SM, Chambers. "Highly efficient neural conversion of human ES and iPS cells by dual inhibition of SMAD signaling." Nat Biotechnol 27 (2009): 275-280. (Year: 2009).*

Lancaster, Madeline A., and Juergen A. Knoblich. "Generation of cerebral organoids from human pluripotent stem cells." Nature protocols 9.10 (2014): 2329-2340. (Year: 2014).*

"International Application Serial No. PCT US2019 036990, International Preliminary Report on Patentability mailed Dec. 30, 2020", 7 pgs.

"International Application Serial No. PCT/US2019/036990, International Search Report mailed Sep. 18, 2019", 3 pgs.

"International Application Serial No. PCT/US2019/036990, Written Opinion mailed Sep. 18, 2019", 5 pgs.

Butts, et al., "Development of the Cerebellum: Simple Steps to Make a 'Little Brain'", Development, vol. 141, No. 21, (Nov. 1, 2014), 4031-4041.

Butts, et al., "Differentiation of V2a Interneurons from Human Pluripotent Stem Cells", Proc. Natl. Acad. Sci. USA, vol. 114, No. 19, (May 9, 2017), 4969-4974.

* cited by examiner

Cluster 0: Chemosensing

Mutation leads to respiratory distress

D17 before dissociation
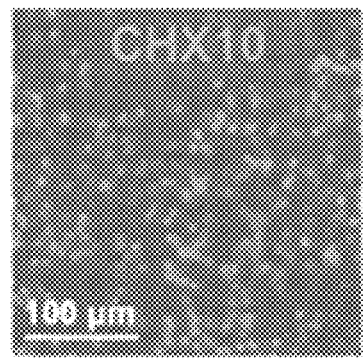 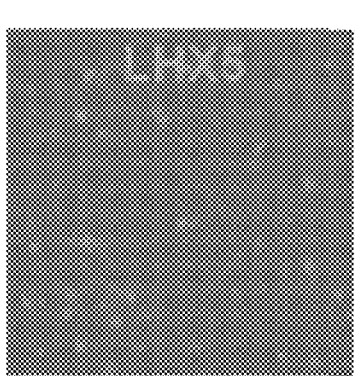 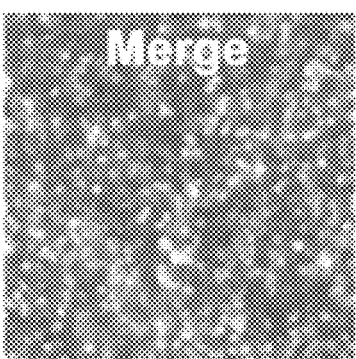
FIG. 10C

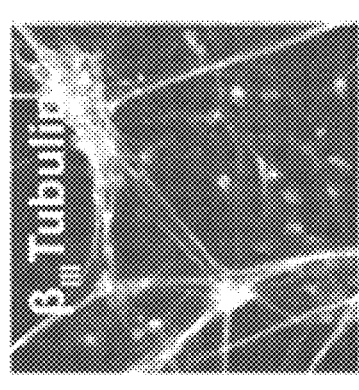
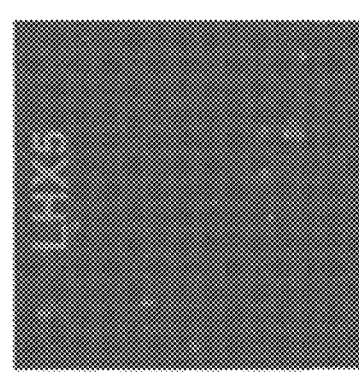
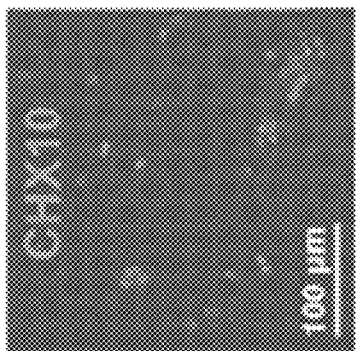
FIG. 10E

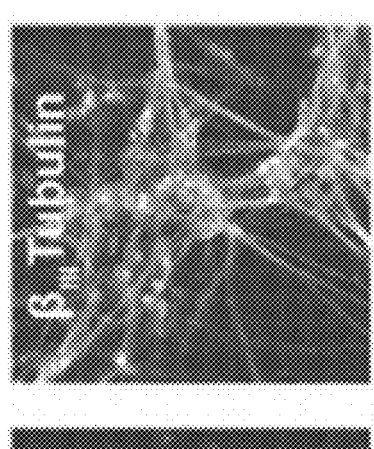
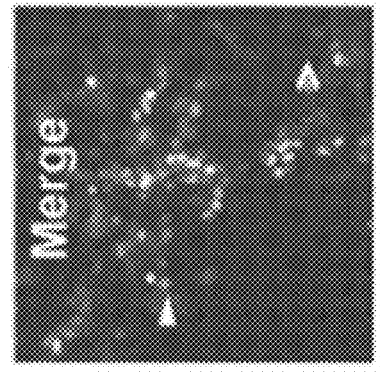
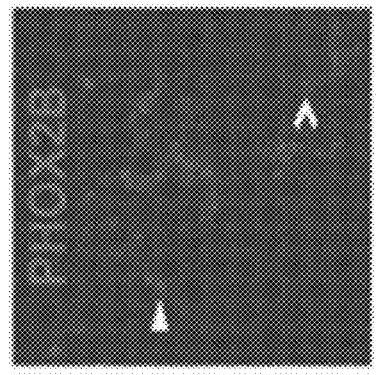
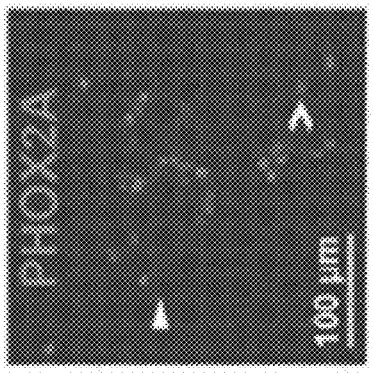
FIG. 10F 24 hr
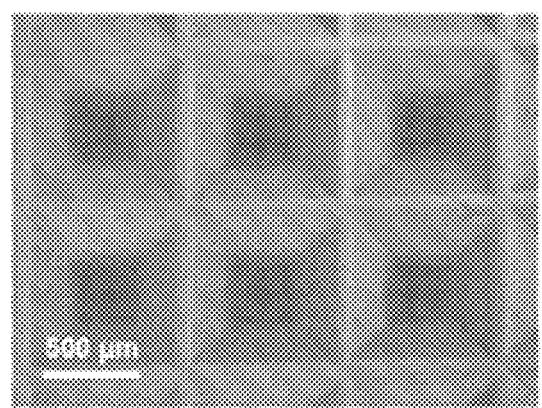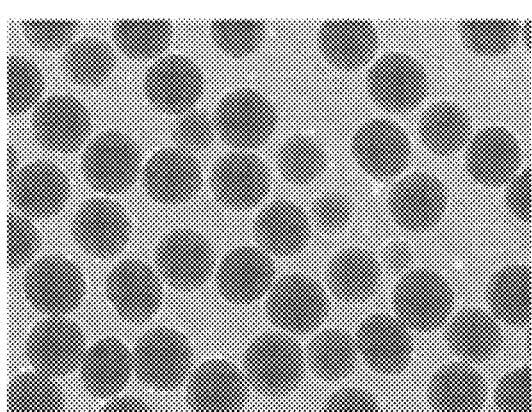
FIG. 12A ORBI- SHAKER CO²
All Environmental Shaker

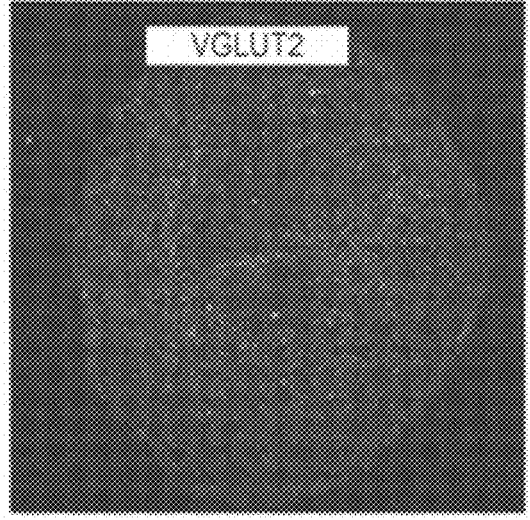
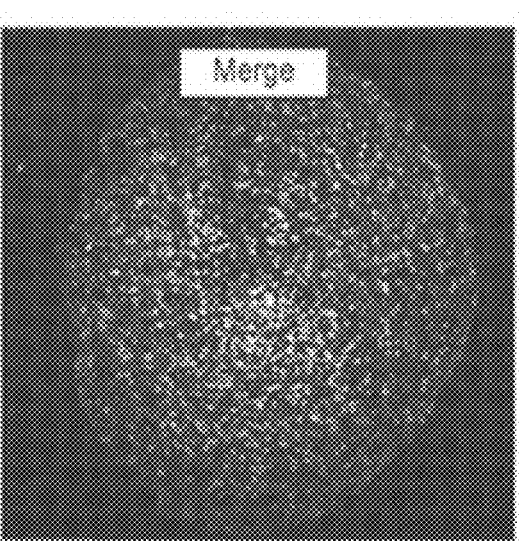
FIG. 21F
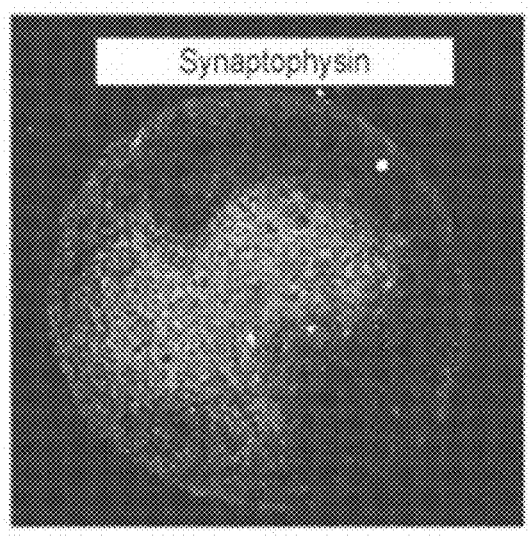
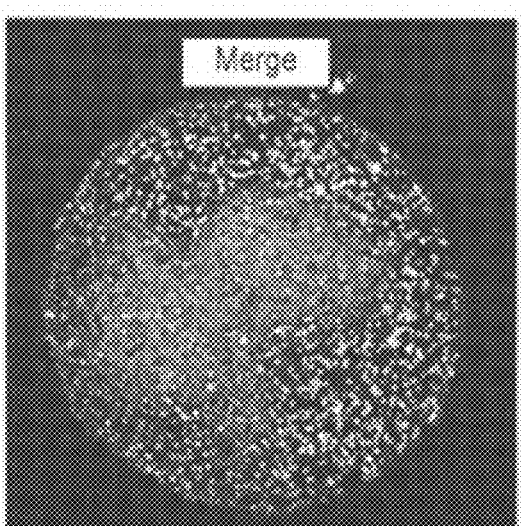
FIG. 21G

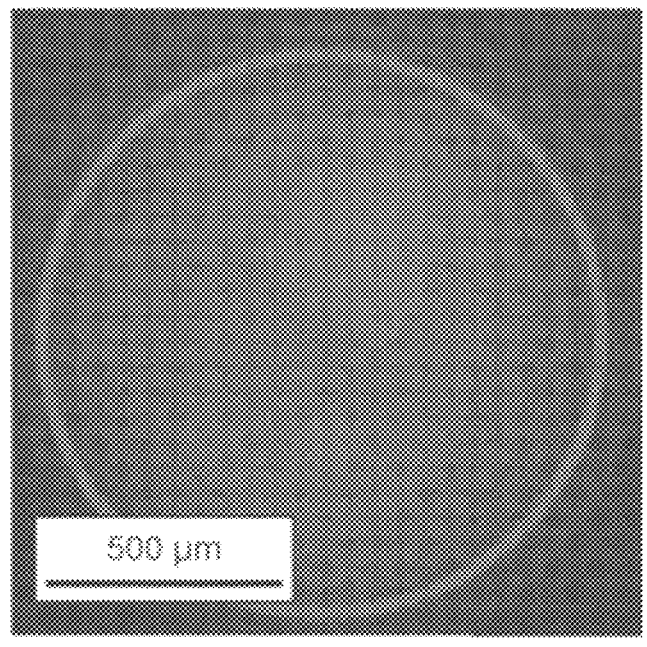
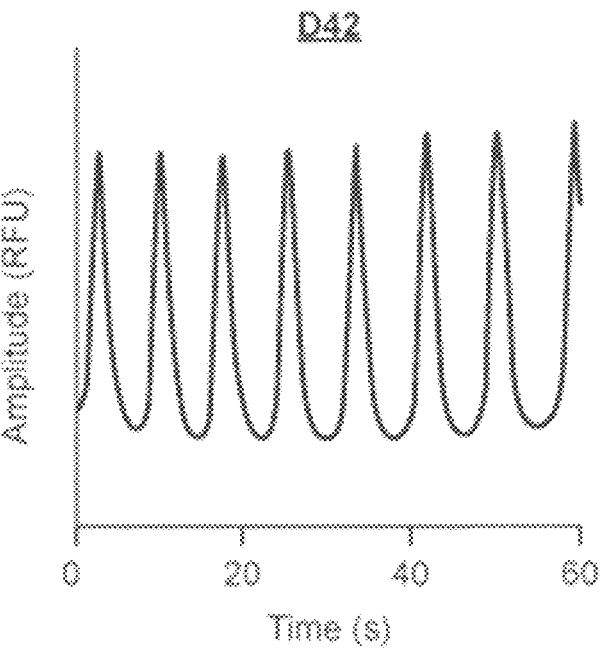
FIG.22A

D52
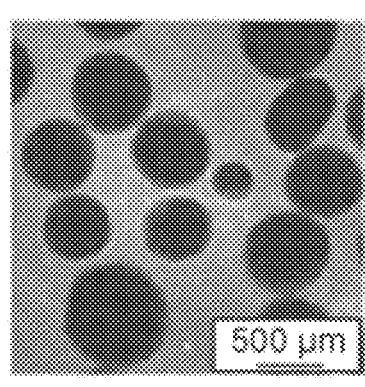
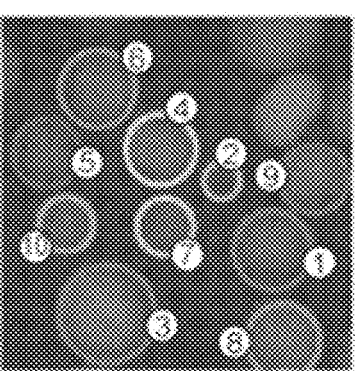
i
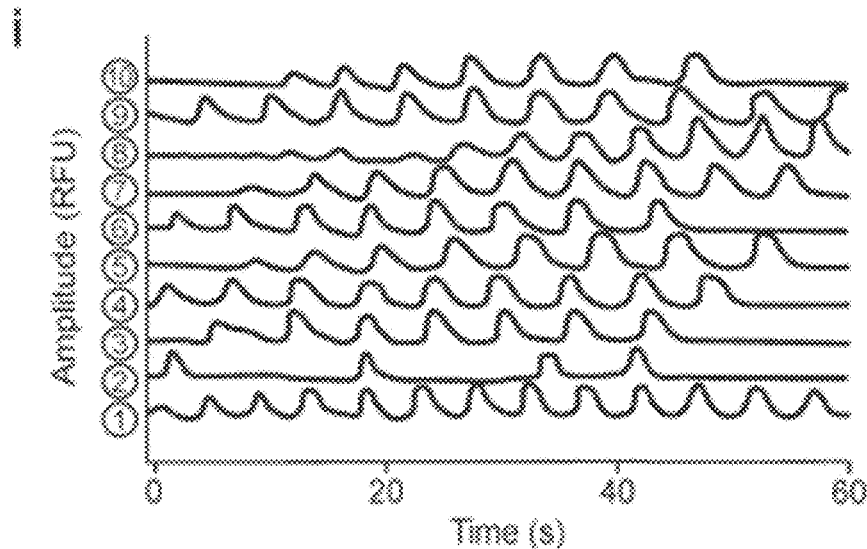
ii
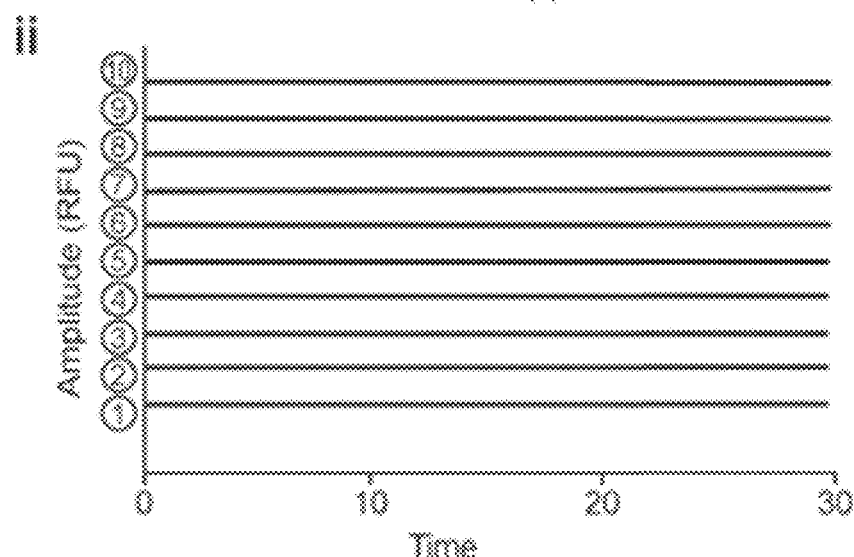
FIG. 22B

D63
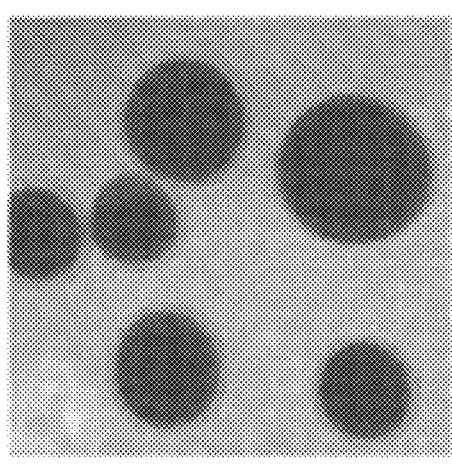
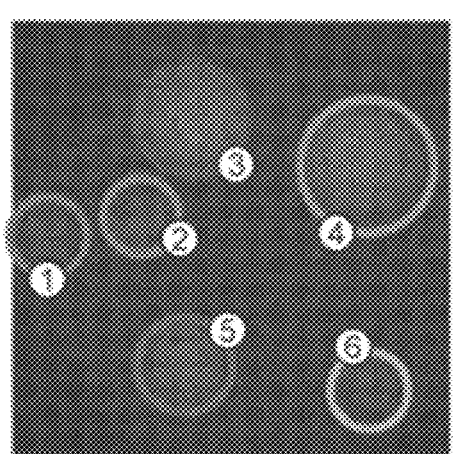
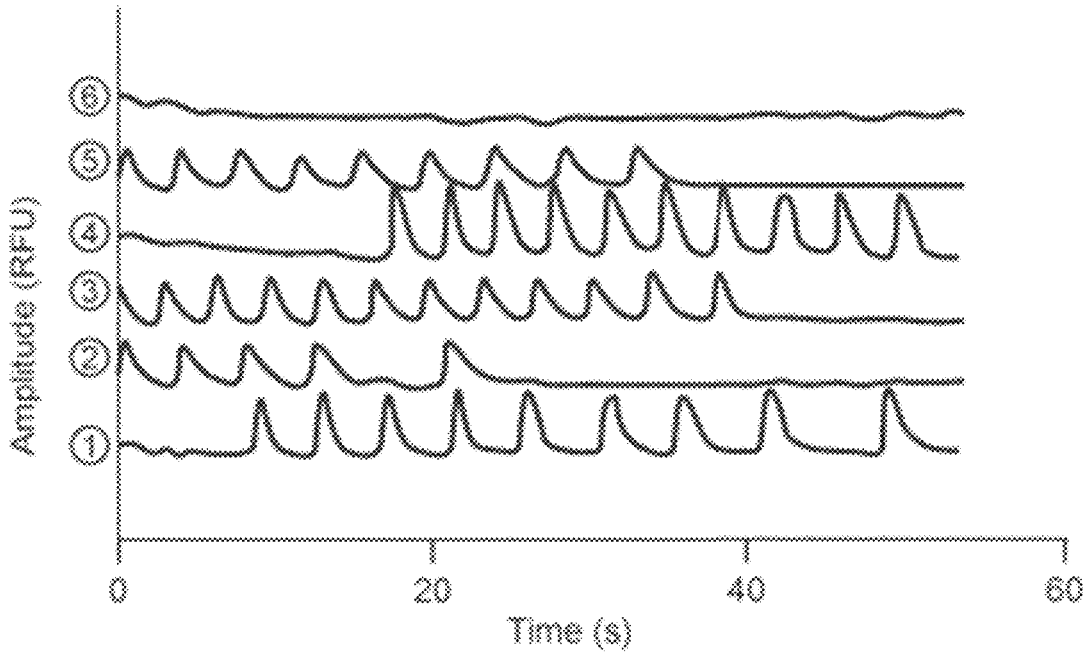
FIG. 22C

D69
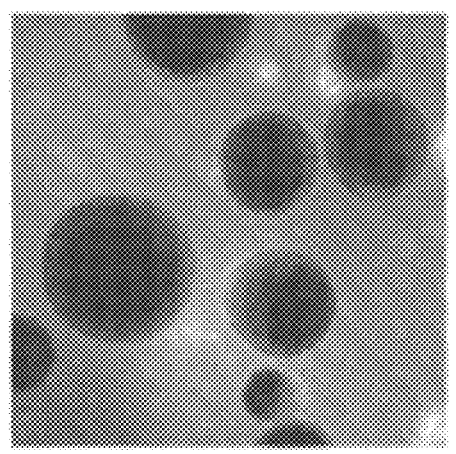
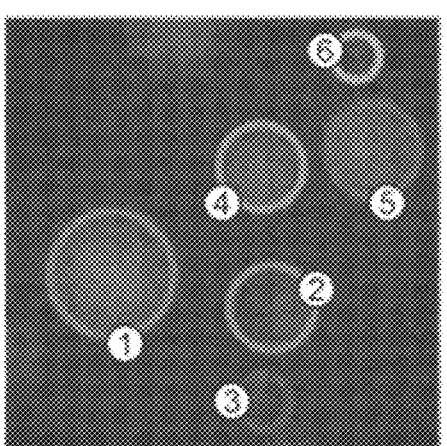
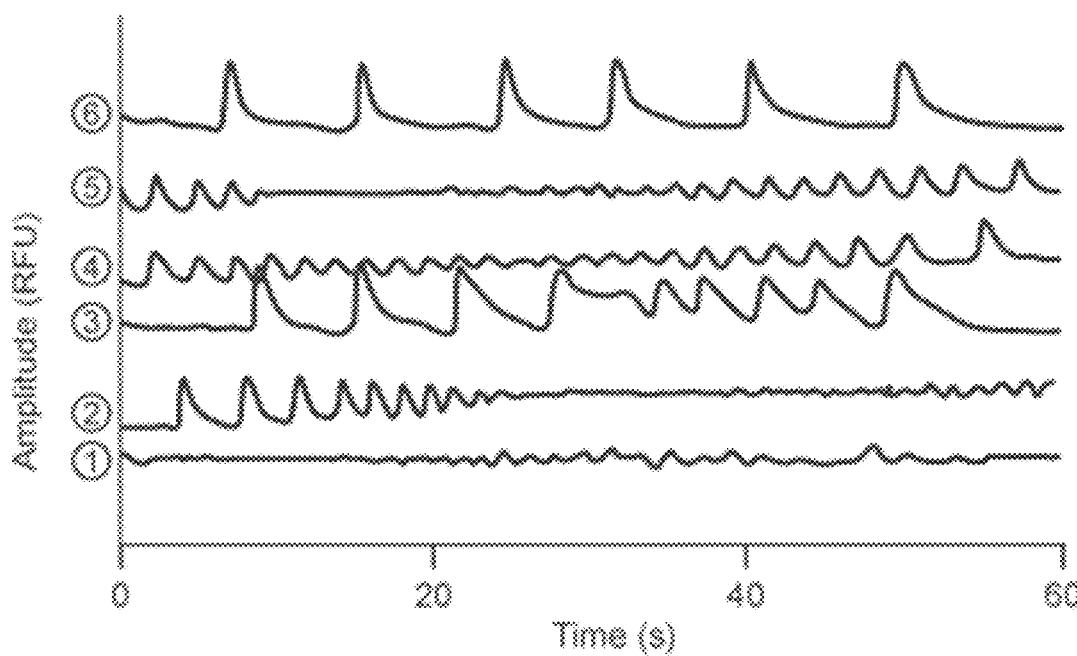
FIG. 22D

D82
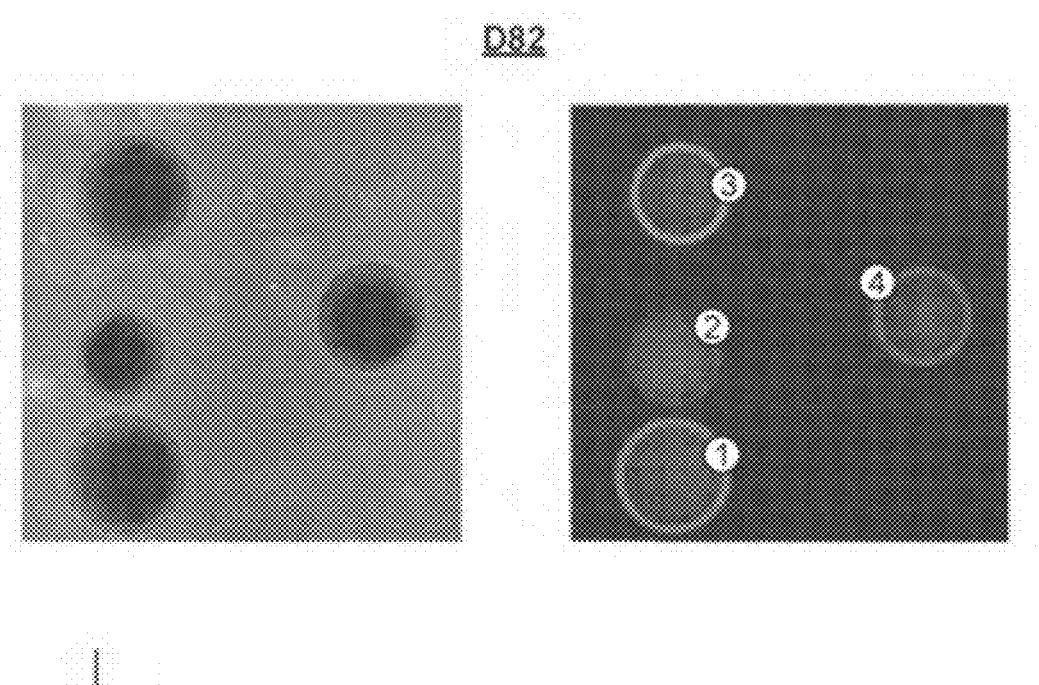
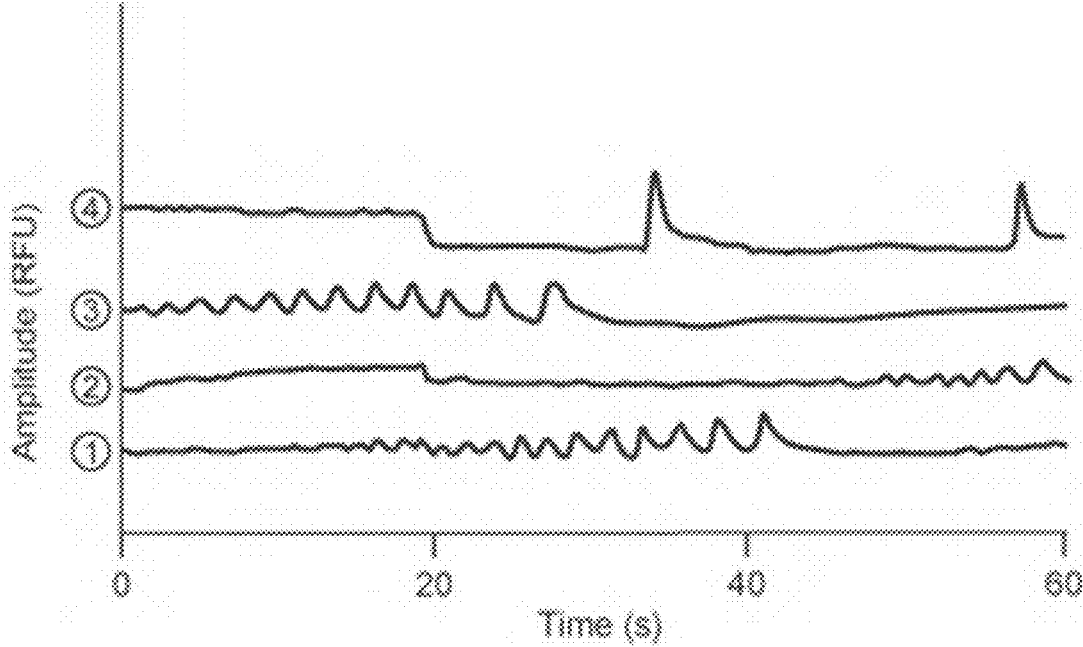
FIG. 22E

D92
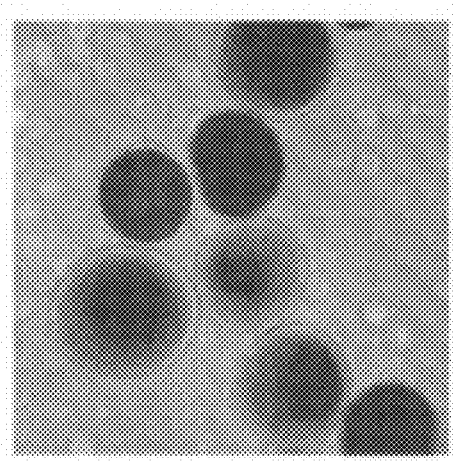
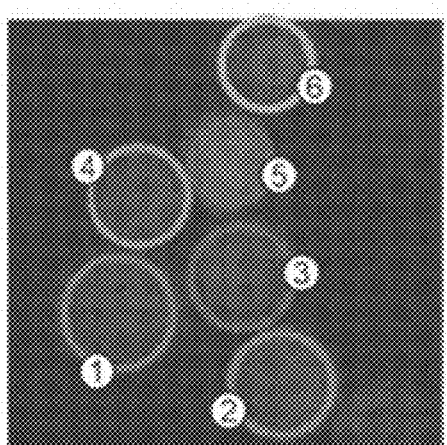
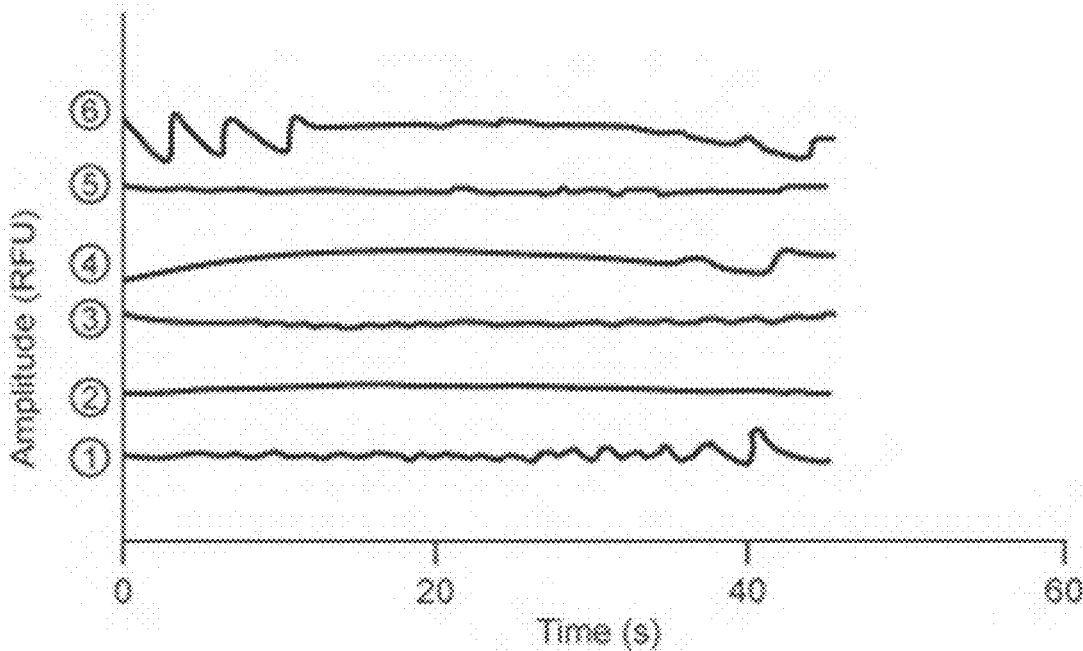
FIG. 22F

GENERATION OF A POPULATION OF HINDBRAIN CELLS AND HINDBRAIN-LIKE ORGANOIDS FROM PLURIPOTENT STEM CELLS

PRIORITY APPLICATIONS

This application is a U.S. national Stage Filing under 35 U.S.C. 371 from International Patent Application Serial No. PCT/US2019/036990, filed Jun. 13, 2019, published as WO/2019/245859 A1 on Dec. 26, 2019, which application claims the benefit of priority to U.S. Provisional Patent Application Ser. No. 62/688,236, filed Jun. 21, 2018, the contents of both which are incorporated by reference herein in their entireties.

INTRODUCTION

The hindbrain is the most conserved central nervous system structure in vertebrates and is critical to the control of autonomic function, including respiration. V2a and V0 interneurons (IN) are critical neuronal populations in the phrenic circuit that provide input to respiratory control centers, while chemosensitive neurons respond to changes in metabolic activity. Damage to these populations by cervical spinal cord injury or disease (i.e. ALS) dramatically diminishes respiration.

There are currently no in vitro sources to study hindbrain development and neuronal functional interactions. Thus, there remains a need to develop methods to generate hindbrain neuronal populations to produce in vitro models, which can be used in screening therapeutics and evaluating the therapeutic potential of hindbrain neuronal populations in repairing injury to the central nervous system.

SUMMARY

Provided herein are methods of generating hindbrain cells, including respiratory hindbrain cells, from pluripotent stem cells (PSCs). Also provided are methods of generating a three-dimensional organoid comprising a population of hindbrain cells including a heterogeneous population of interneurons.

Methods of generating a heterogeneous population of interneurons comprising V2a interneurons, V0 interneurons, and chemosensing interneurons, or a combination thereof, from PSCs are provided. Methods of generating a three-dimensional organoid comprising a population of hindbrain cells including a heterogeneous population of interneurons comprising V2a interneurons, V0 interneurons, and chemosensing interneurons, or a combination thereof, are also provided.

A method of the present disclosure may include treating a population of PSCs in vitro with a Wingless-Int (WNT) signaling pathway activator; and culturing the population of PSCs in a neural induction medium comprising: a retinoic acid (RA) signaling pathway activator, a sonic hedgehog (Shh) signaling pathway activator, and a Notch signaling pathway inhibitor, wherein the culturing results in generation of the population of hindbrain cells comprising the heterogeneous population of interneurons, wherein the heterogeneous population of interneurons comprises V2a interneurons, V0 interneurons, chemosensing interneurons, or a combination thereof; and generation of the three-dimensional organoid. Another method of the present disclosure may include culturing a first population of PSCs in vitro in a neural induction medium that comprises: a retinoic acid signaling pathway activator, a sonic hedgehog (Shh) signaling pathway activator, and a Notch signaling pathway inhibitor, wherein the culturing results in generation of a second population of cultured cells comprising CHX10+ V2a interneurons, LHX5+ V0 interneurons, PHOX2A/B+ chemosensing interneurons, or a combination thereof.

In some embodiments, the PSCs used in the methods described herein are human pluripotent stem cells (hPSCs).

In some embodiments, the retinoic acid signaling pathway activator includes a retinoic acid receptor agonist. In exemplary embodiments, the retinoic acid receptor agonist includes retinoic acid, or a derivative thereof. In some embodiments, the Shh signaling pathway activator includes a Smoothened agonist. In exemplary embodiments, the Smoothened agonist is purmorphamine (pur), or a derivative thereof. In some embodiments, the Notch signaling pathway inhibitor includes an inhibitor of Notch receptor activation. In exemplary embodiments, the inhibitor of Notch receptor activation is a Notch receptor antagonist or a γ-secretase inhibitor. In some aspects, the γ-secretase inhibitor is N-[(3, 5-difluorophenyl)acetyl]-L-alanyl-2-phenyl]glycine-1,1-dimethylethyl ester (DAPT). In exemplary embodiments, the WNT signaling pathway activator is selected from the group consisting of CHIR99021, WAY-316606, IQ1, QS11, SB-216763, BIO, and DCA. In some embodiments, the WNT signaling pathway activator is a GSK3 inhibitor, for example, including, without limitation, CHIR99021.

In some embodiments, at least 10%, e.g., at least 20%, 30%, 40%, 50%, 60%, 70%, or 80%, of the population of hindbrain cells including the heterogeneous population of interneurons are V2a interneurons. In such embodiments, the V2a interneurons are CHX10+ V2a interneurons. In some embodiments, at least 10%, e.g., at least 20%, 30%, 40%, 50%, 60%, 70%, or 80%, of the population of hindbrain cells including the heterogeneous population of interneurons are V0 interneurons. In such embodiments, the V0 interneurons are LHX5+ V0 interneurons. In some embodiments, at least 10%, e.g., at least 20%, 30%, 40%, 50%, 60%, 70%, or 80%, of the population of hindbrain cells including the heterogeneous population of interneurons are chemosensing interneurons. In such embodiments, the chemosensing interneurons are PHOX2A+ or PHOX2B+ chemosensing interneurons.

In some embodiments, gene expression in the population of hindbrain cells including the heterogeneous population of interneurons is increased, compared to the population of PSCs, for one or more genes selected from: PHOX2A, PHOX2B, ADCYAP1, CHX10, SOX14, IRX3, LHX5, PAX2, MAB21L2, SOX21, EVX1, and EVX2.

In some embodiments, the culturing comprises contacting the population of PSCs, in order, with: a WNT signaling pathway activator; a first neural induction medium comprising the retinoic acid signaling pathway activator; and a second neural induction medium comprising the retinoic acid signaling pathway activator, the Shh signaling pathway activator, and the Notch signaling pathway inhibitor, under conditions sufficient to generate the population of hindbrain cells comprising the heterogeneous population of interneurons, wherein the heterogeneous population of interneurons is enriched for V2a interneurons, V0 interneurons, chemosensing interneurons, or a combination thereof.

The present disclosure further provides a method including reseeding at least some of the population of hindbrain cells including the heterogeneous population of interneurons onto a neural maturation substrate; and culturing the seeded population of hindbrain cells including the heterogeneous population of interneurons in a neural maturation medium, thereby generating a mature population of hindbrain cells including the heterogeneous population of interneurons.

The present disclosure further provides an isolated three-dimensional organoid generated according to any of the methods described herein. In some embodiments, the isolated three-dimensional organoid comprises a neural rosette. In some embodiments, the isolated three-dimensional organoid comprises V0 interneurons, V2a interneurons, and chemosensing neurons. In some embodiments, the isolated three-dimensional organoid comprises more V0 interneurons than V2a interneurons. In some embodiments, the isolated three-dimensional organoid exhibits synchronous, periodic $Ca^{2+}$-transients.

In addition to the provided methods, the present disclosure also provides a non-human animal model of hindbrain development, including a population of hindbrain cells comprising a heterogeneous population of interneurons produced according to the methods described herein.

BRIEF DESCRIPTION OF THE DRAWINGS

FIG. 1A shows the schematic detailing experimental procedure. Cultures were dissociated and replated at day 17 and analysis occurred at day 20. FIGS. 1B and 1C show the flow cytometry analysis of CHX10 at day 17 and day 20 without replating as well as at day 20 with a replating step in the presence of 10 µM or 1 µM rock inhibitor (Ri) using the WTB (FIG. 1B) or WTC (FIG. 1C) hiPSC cell line. *=p<0.05, one-way ANVOA and Tukey post hoc comparison FIG. 2A shows schematic detailing experimental procedure. FIGS. 2B and 2C show flow cytometry analysis of CHX10 following differentiation without WNT activation (untreated, UT) or with WNT activation (CHIR) using the WTB (FIG. 2B) or WTC (FIG. 2C) hiPSC cell line. *=p<0.05, un-paired t-test FIG. 3A shows a tSNE plot of replated V2a interneuron cultures indicating 5 clusters. FIG. 3B shows neurofilament light chain (NEFL) expression (dark gray dots) FIG. 3C shows neurofilament medium chain (NEFM) expression (dark gray dots). FIG. 3D show a dendrogram of the relationship between clusters

FIG. 5A shows a flow cytometry analysis of CHX10 from the V2a interneuron population analyzed by single cell RNA sequencing. FIG. 5B shows (HX10 expression (dark gray dots). Light gray dots represent remaining cells in the population. FIG. 5C-5E show a violin plot of CHX10, SOX14, and SOX21 expression.

FIG. 9A shows genes that are expressed in respiratory hindbrain regions including the Bötzinger Complex and the pre Bötzinger Complex. FIG. 9B shows genes implicated in respiratory distress.

FIGS. 10A-10F show confirmation of hindbrain respiratory populations in vitro. FIG. 10A shows a flow cytometry analysis of CHX10, LHX5, PHOX2B, and PHOX2A in the hPSC-derived cultures. FIG. 10B shows a dotplot of CHX10 and LHX5 co-staining. FIGS. 10C and 10D show immunocytochemistry on in vitro cultures at day 17 of CHX10 LHX5 and nuclei labeling (FIG. 10C) as well as PHOX2A, PHOX2B and nuclei labeling (FIG. 10D). FIGS. 10E and 10F show immunocytochemistry on in vitro cultures that were dissociated at day 17 and replated for 6 days. Images show CHX10, LHX5, $\beta_{III}$Tubulin, and nuclei labeling (FIG. 10E) as well as PHOX2A, PHOX2B, $\beta_{III}$Tubulin, and nuclei labeling (FIG. 10F).

FIG. 11A shows a flow cytometry analysis of CHX10 and LHX5 expression with varying purmorphamine (pur) concentration. *=p<0.05 compared to 30 nM and 100 nM, one-way ANVOA and Tukey post hoc comparison. $=p<0.05 compared to 30 nM and 30 nM, one-way ANVOA and Tukey post hoc comparison. FIG. 11B shows a flow cytometry analysis of CHX10 and LHX5 expression with varying RA concentration. *=p<0.05 compared to 30 nM and 100 nM, one-way ANVOA and Tukey post hoc comparison. $=p<0.05 compared to all groups, one-way ANVOA and Tukey post hoc comparison.

FIG. 12A-12G show hindbrain organoid differentiation. FIG. 12A shows formation of aggregates from hPSCs. FIG. 12B shows a rotary orbital shaker for suspension culture. FIG. 12C shows phase contrast images of organoids at day 5, day 12, and day 17 of the differentiation. FIG. 12D shows the diameter of the aggregates throughout the 17 day differentiation. FIG. 12E shows the circularity, as calculated by the ratio of the long axis to the short axis, throughout the 17 day differentiation. FIG. 12F shows a flow cytometry analysis of CHX10, LHX5, PHOX2B, and PHO2A at day 17. FIG. 12G shows immunocytochemistry of organoids at day 17.

FIG. 13A shows phase contrast images of the organoids at day 1, day 3, and day 7. FIG. 13B shows phase contrast images of the organoids at day 17 treated with 10 nM, 100 nM, and 1 µM. FIG. 13C shows the diameter of the organoids throughout the differentiation. FIG. 13D shows a flow cytometry analysis of CHX10, LHX5, PHOX2B, and PHO2A at day 17 of organoids treated with 10 nM, 100 nM, and 1 µM pur. >p<0.05 compared to 100 nM and 1 µM, $ p<0.05 compared to 10 nM and 1 µM, * p<0.05 compared to 10 nM and 100 M.

FIG. 14A shows phase contrast images of the organoids at day 3, day 7, day 11, day 13, and day 17. FIG. 14B shows H&E staining of sectioned organoids at day 3, day 7, day 11, day 13, and day 17.

FIG. 15A shows immunostaining for OCT4 and SOX2 at day 3, day 7, day 11, and day 17. FIG. 15B shows immunostaining for Ki67 and PH3 at day 3, day 7, day 11, and day 17.

5

Figure 16A:
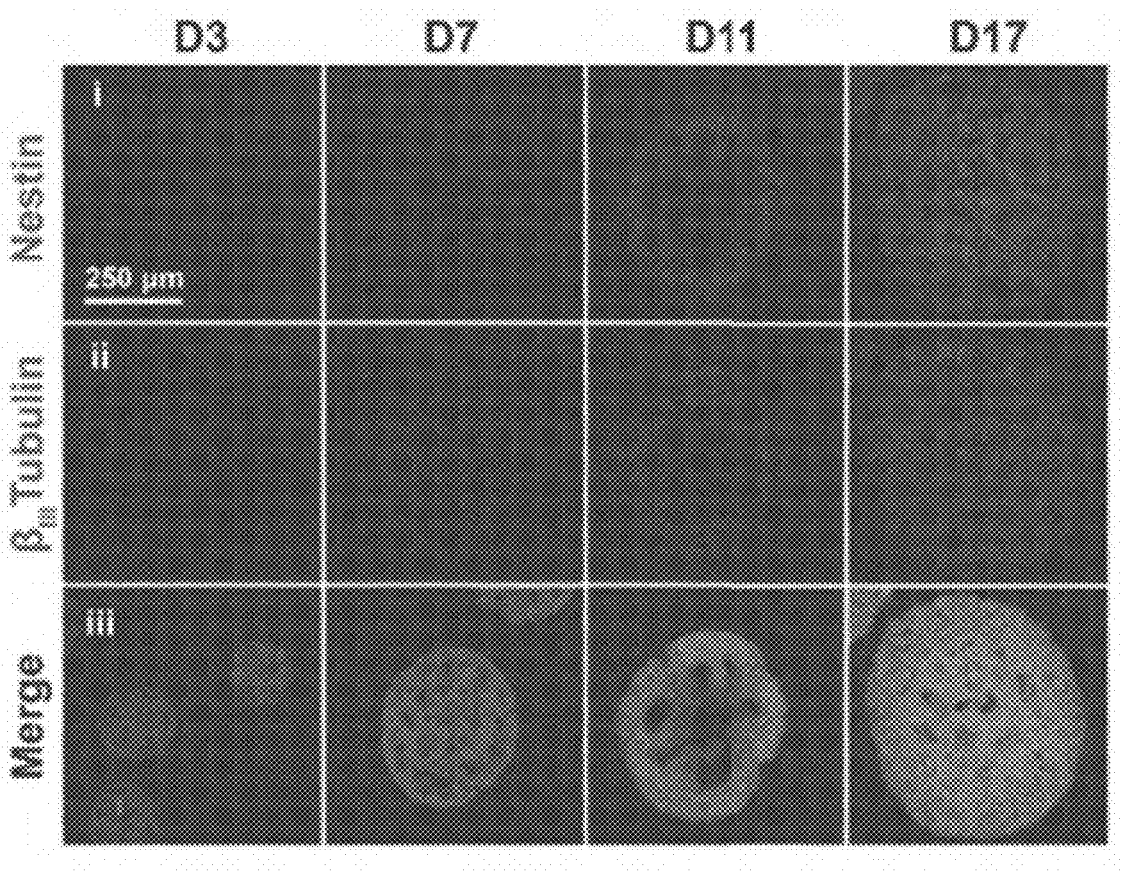
Figure 16B:
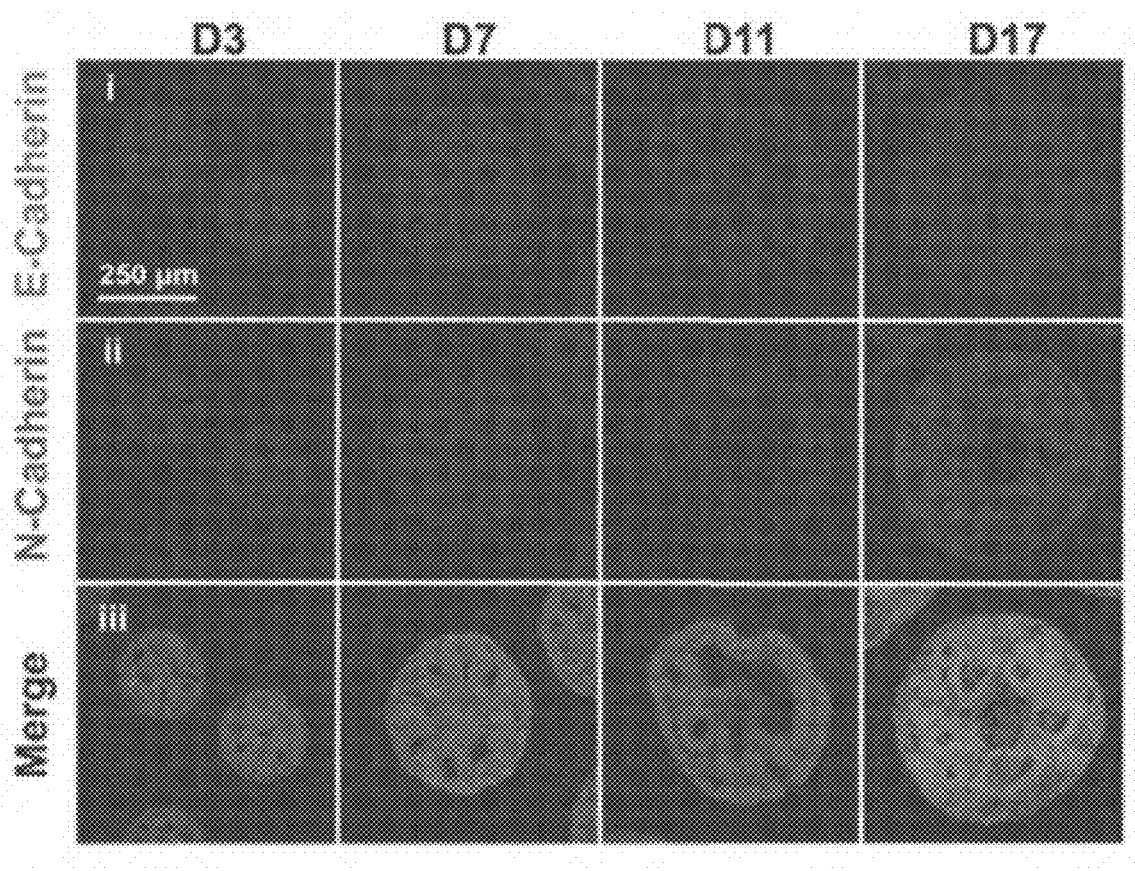

FIG. 16A-16B show analysis of neurogenesis in organoid sections throughout differentiation. FIG. 16A shows immunostaining for Nestin and BinTubulin at day 3, day 7, day 11, and day 17. FIG. 16B shows immunostaining for N-Cadherin and E-Cadherin at day 3, day 7, day 11, and day 17.

Figure 17A:
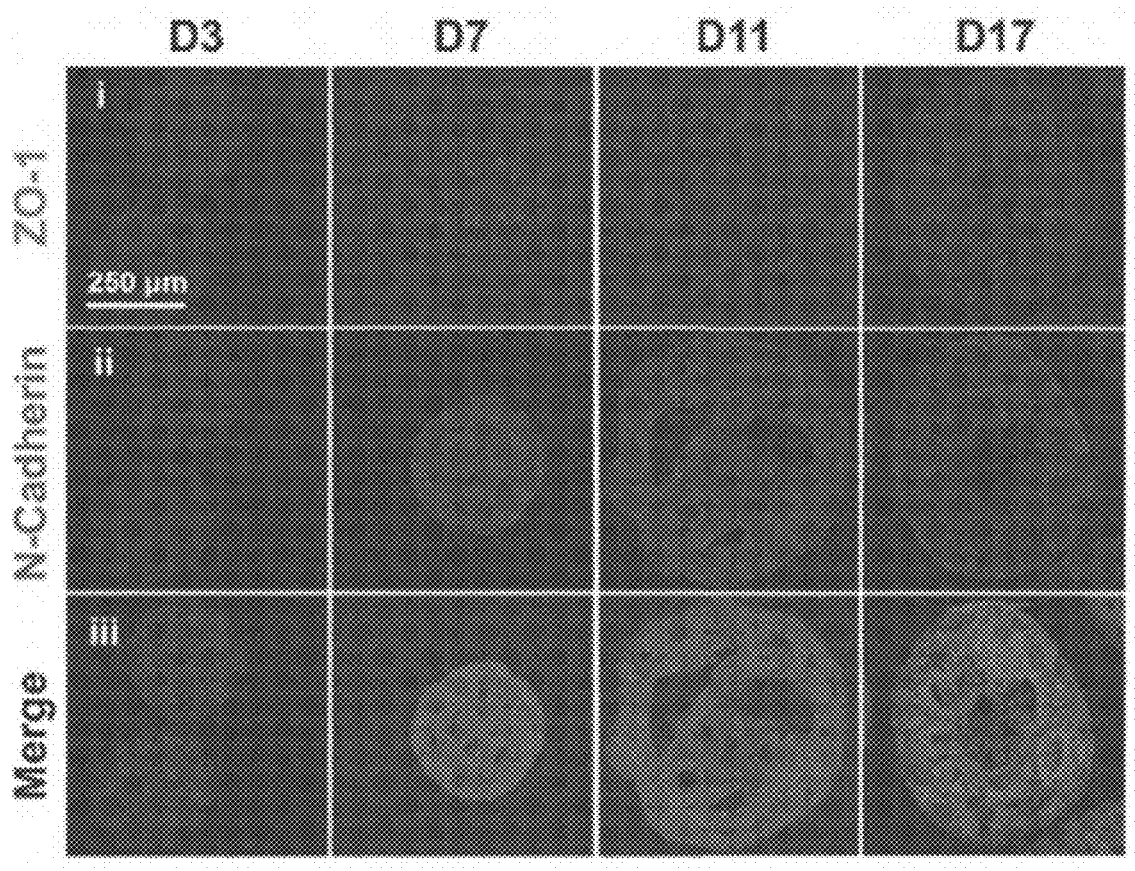
Figure 17B:
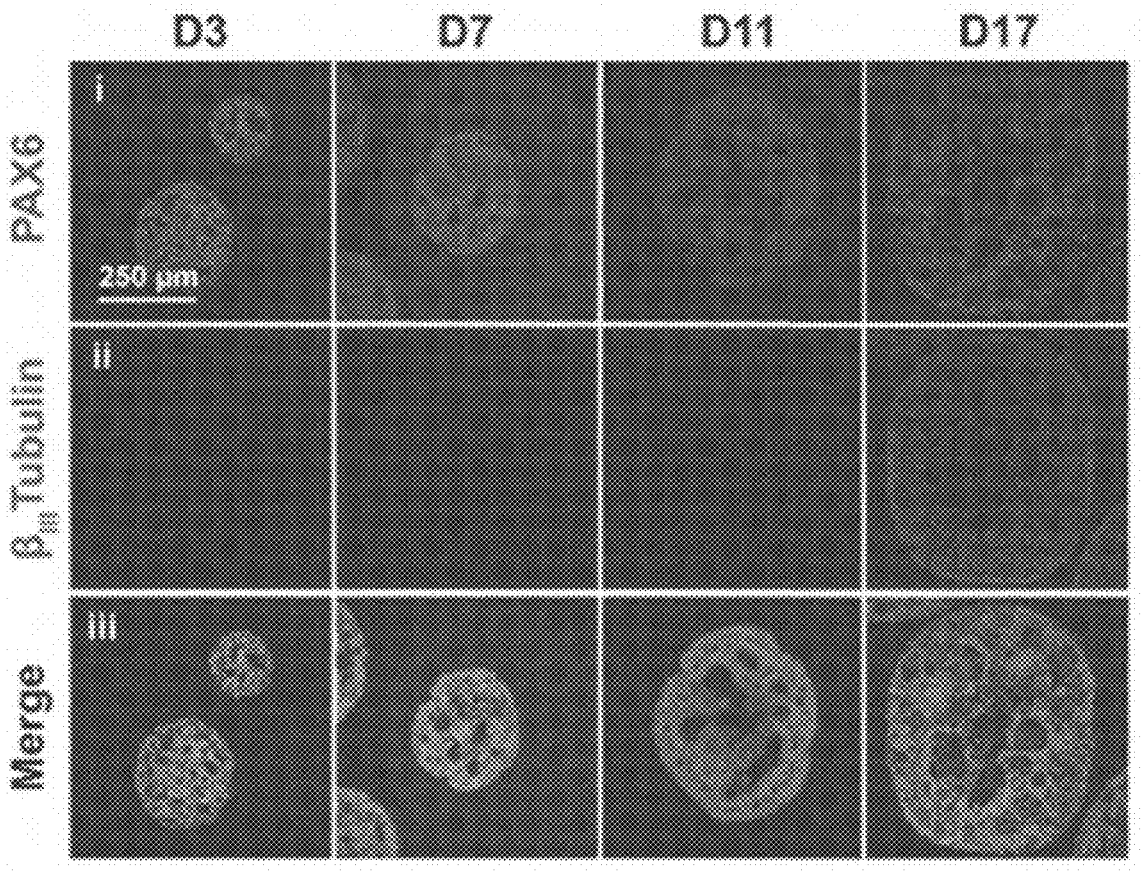

FIG. 17A-17B show analysis of rosette formation in organoid sections throughout differentiation. FIG. 17A shows immunostaining for N-Cadherin and ZO-1 at day 3, day 7, day 11, and day 17. FIG. 17B shows immunostaining for PAX6 and Bun Tubulin at day 3, day 7, day 11, and day 17.

Figure 18A:
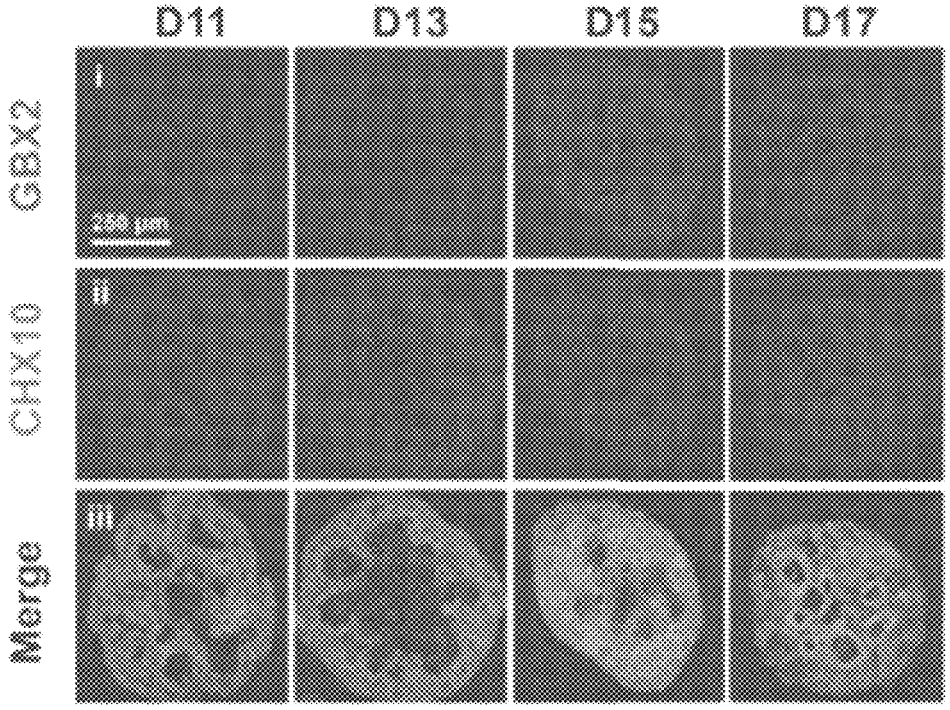
Figure 18B:
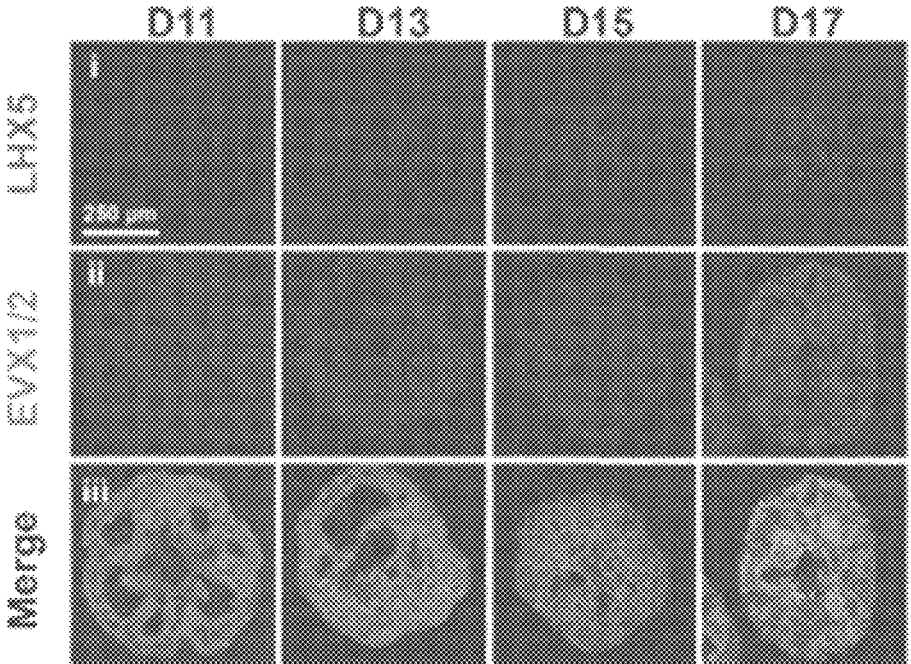
Figure 18C:
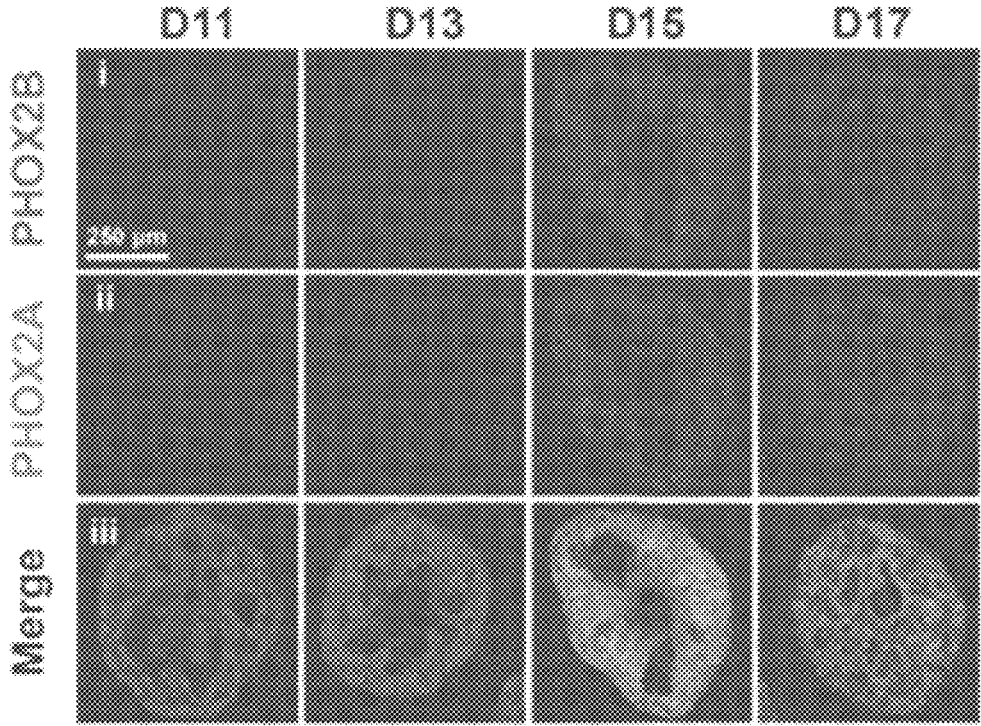

FIGS. 18A-18C show results from an analysis of pluripotency and proliferation in organoid sections throughout differentiation. FIG. 18A shows immunostaining for CHX10 and GBX2 at day 11, day 13, day 15, and day 17. Scale bar=250 μm. FIG. 18B shows immunostaining for EVX1/2 and LHX5 at day 11, day 13, day 15, and day 17. Scale bar=250 μm. FIG. 18C shows immunostaining for PHOX2A and PHOX2B at day 11, day 13, day 15, and day 17. Scale bar=250 μm.

Figure 19A:
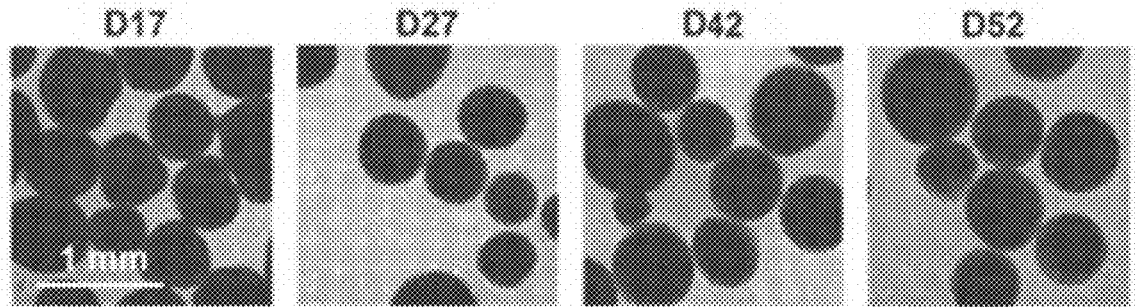
Figure 19B:
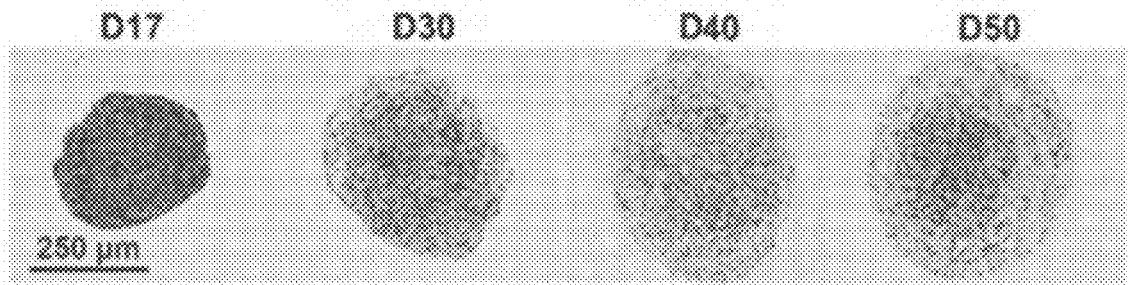

FIGS. 19A-19B show phase contrast and H&E of organoids during maturation. FIG. 19A shows phase contrast images of the organoids at day 17, day 27, day 42, and day 52. FIG. 19B shows H&E staining of sectioned organoids at day 17, day 30, day 40, and day 50.

Figure 20:
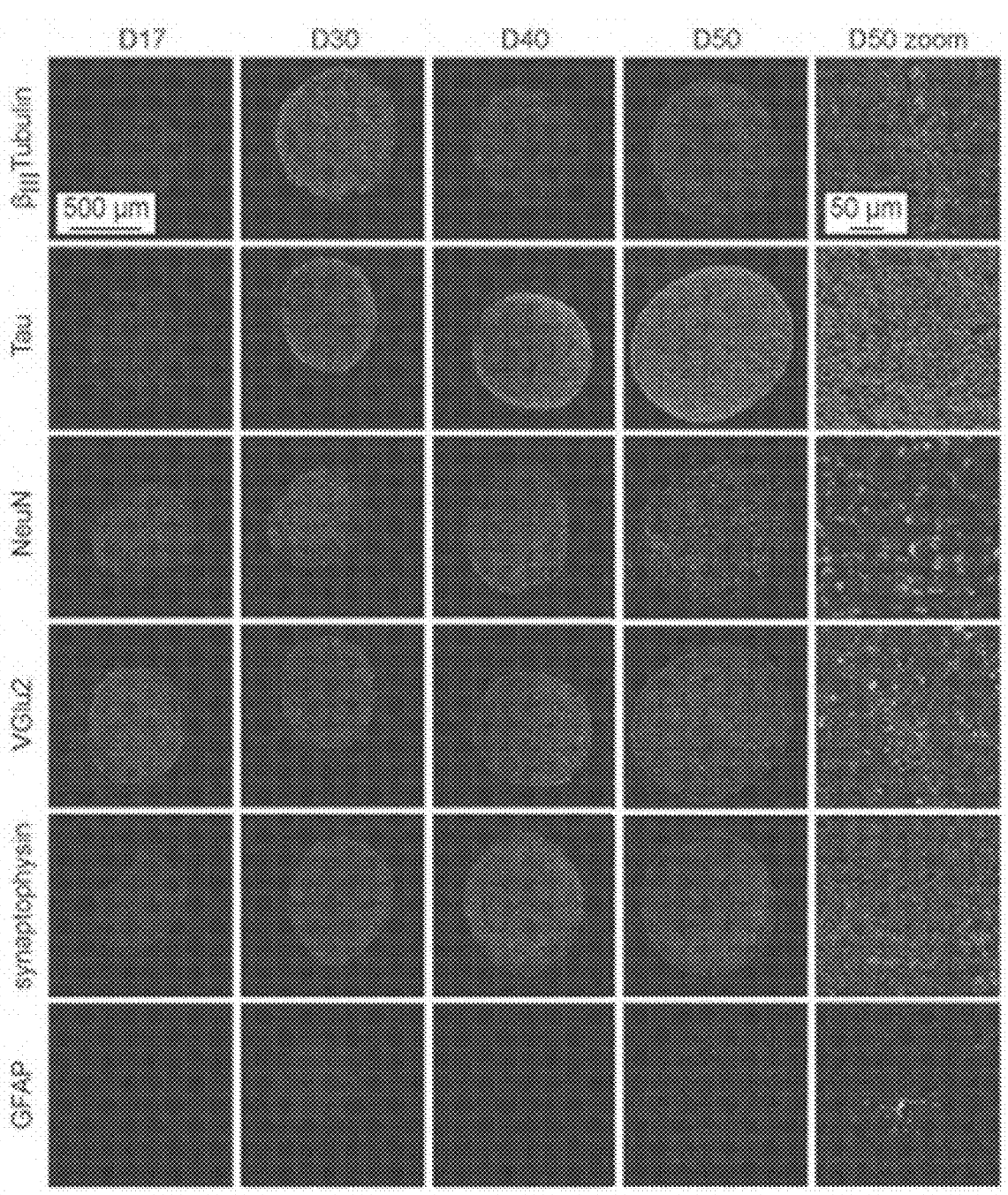

FIG. 20 shows an assessment of early maturation in sectioned organoids with immunostaining for $\beta_{III}$ Tubulin, Tau, NeuN, VGlut2, synaptophysin, and GFAP at days 17, 30, 40, and 50 of culture.

Figure 21A:
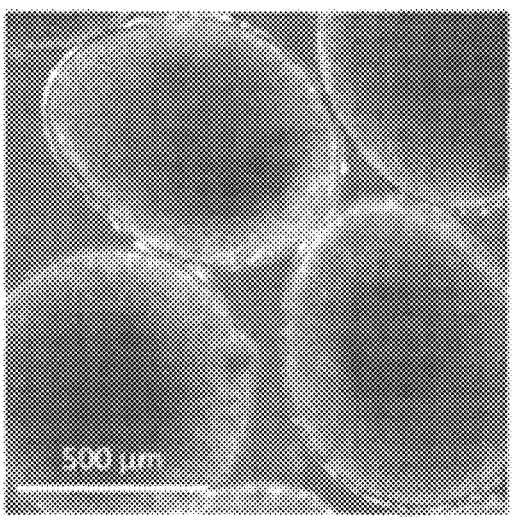
Figure 21B:
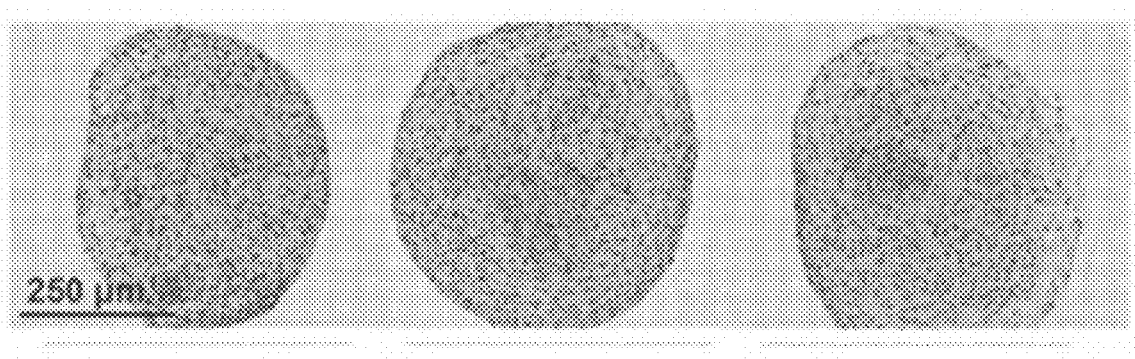
Figure 21C:
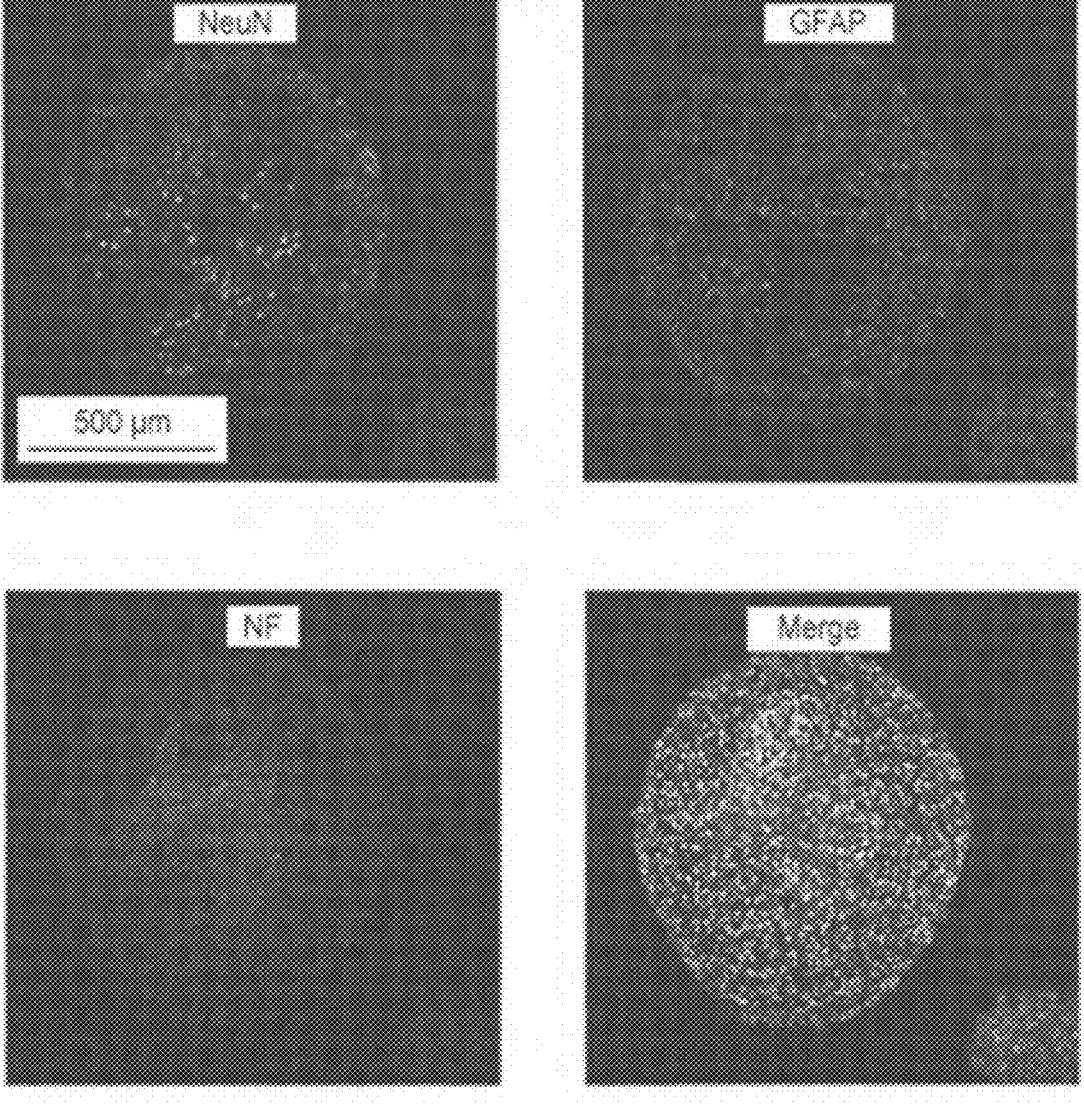
Figure 21D:
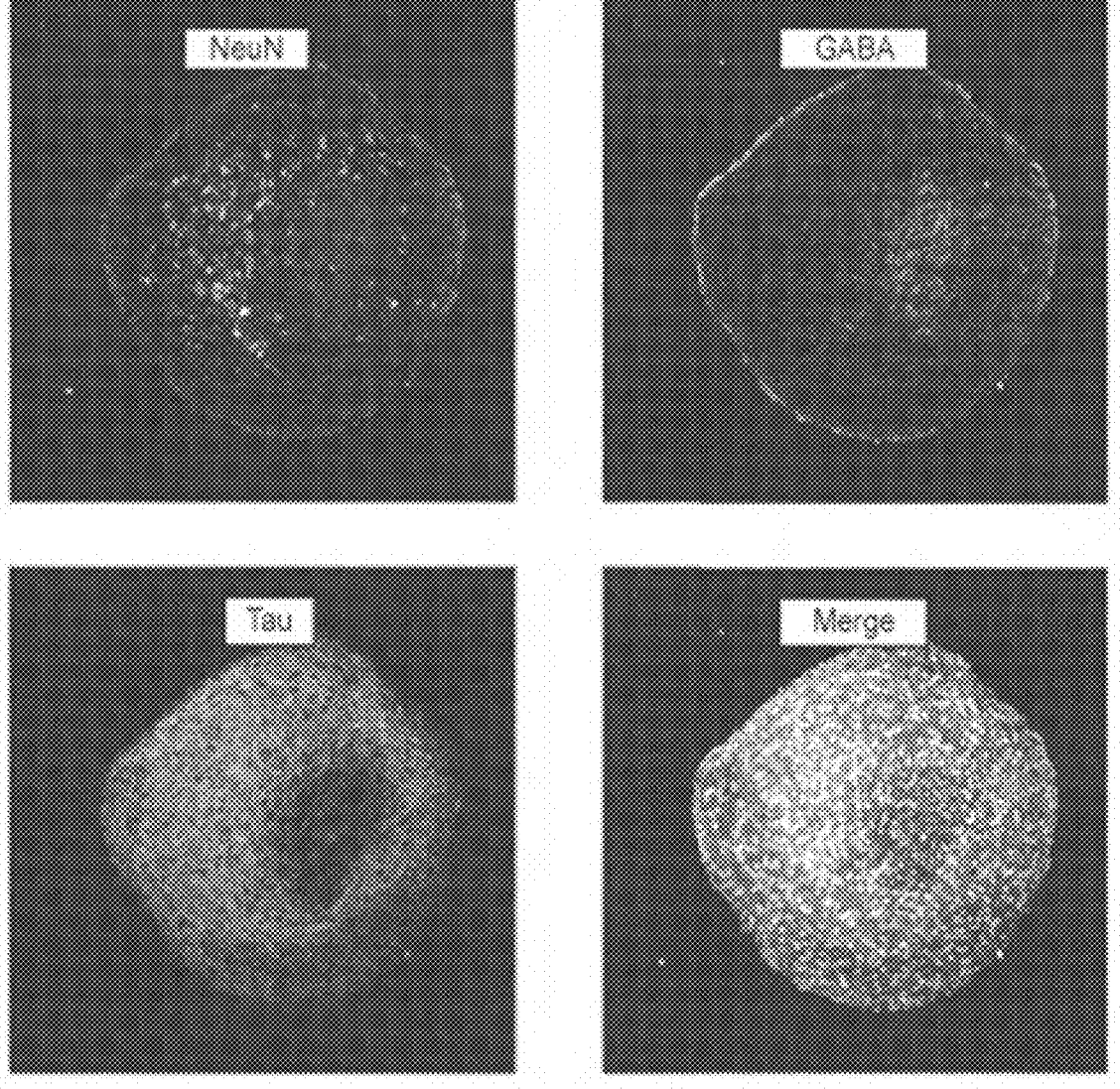
Figure 21E:
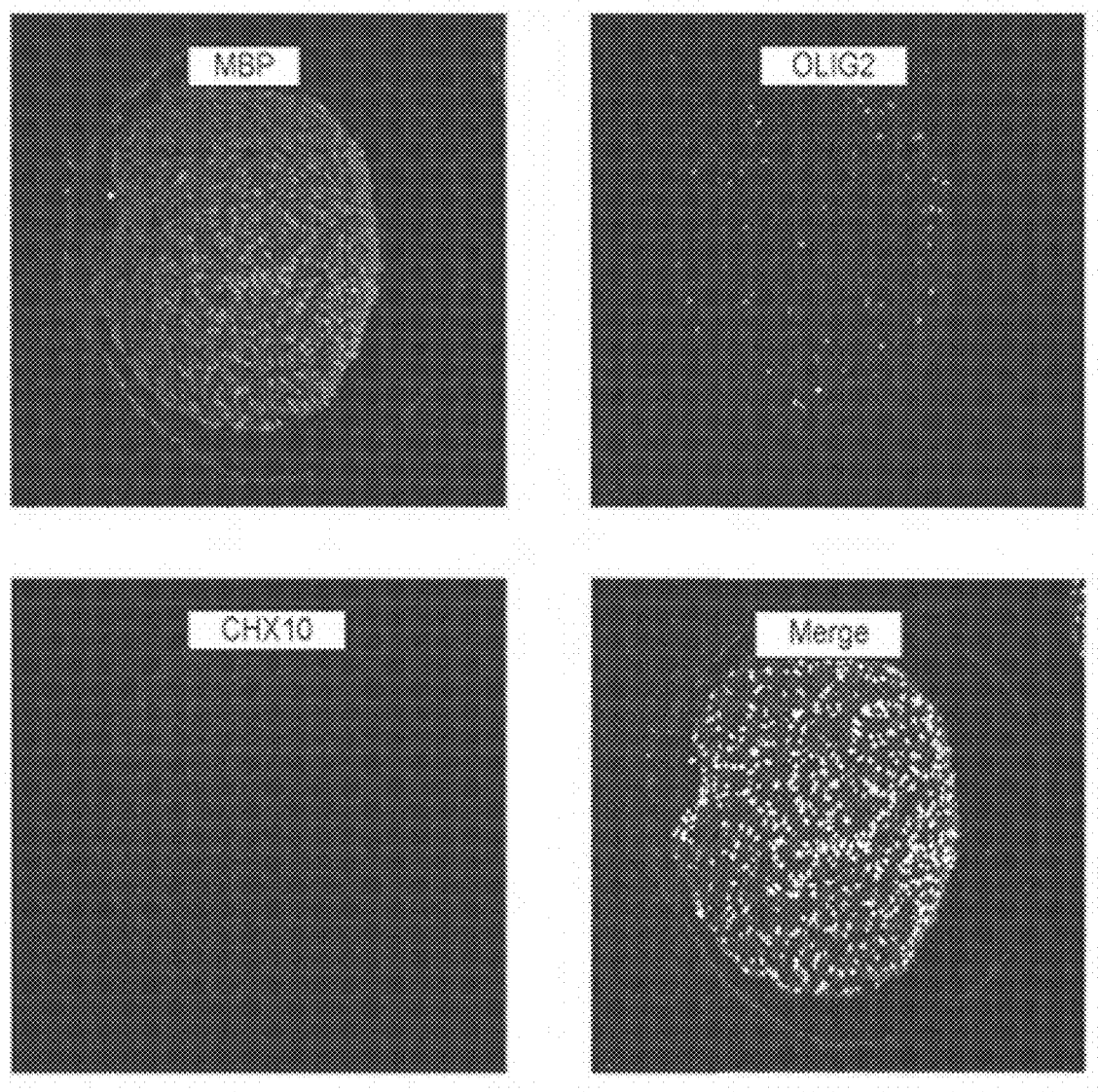

FIGS. 21A-21G show an assessment of maturation markers in 100 day old organoids. FIG. 21A shows phase contrast image at 100 days. FIG. 21B shows H&E of sectioned organoids. FIG. 21C shows immunostaining for NeuN, GFAP, and Neurofilament (NF). FIG. 21D shows immunostaining for NeuN, GABA, and Tau. FIG. 21E shows immunostaining for myelin basic protein (MBP), OLIG2, and CHX10. FIG. 21F shows immunostaining for VGLUT2, FIG. 21G shows immunostaining for synaptophysin.

FIGS. 22A-22F show synchronous $Ca^{2+}$ fluctuations in the organoids throughout maturation. FIG. 22A shows $Ca^{2+}$ transients in one organoid at day 42. FIG. 22B shows $Ca^{2+}$ transients of a field of organoids taken right out of the incubator (i) and the same region 2 minutes later (ii). FIG. 22C-22F show $Ca^{2+}$-transients of a field of organoids at day 63, 69, 82, and 92. Colored circles demarcate regions of interest (ROI).

Figure 23A:
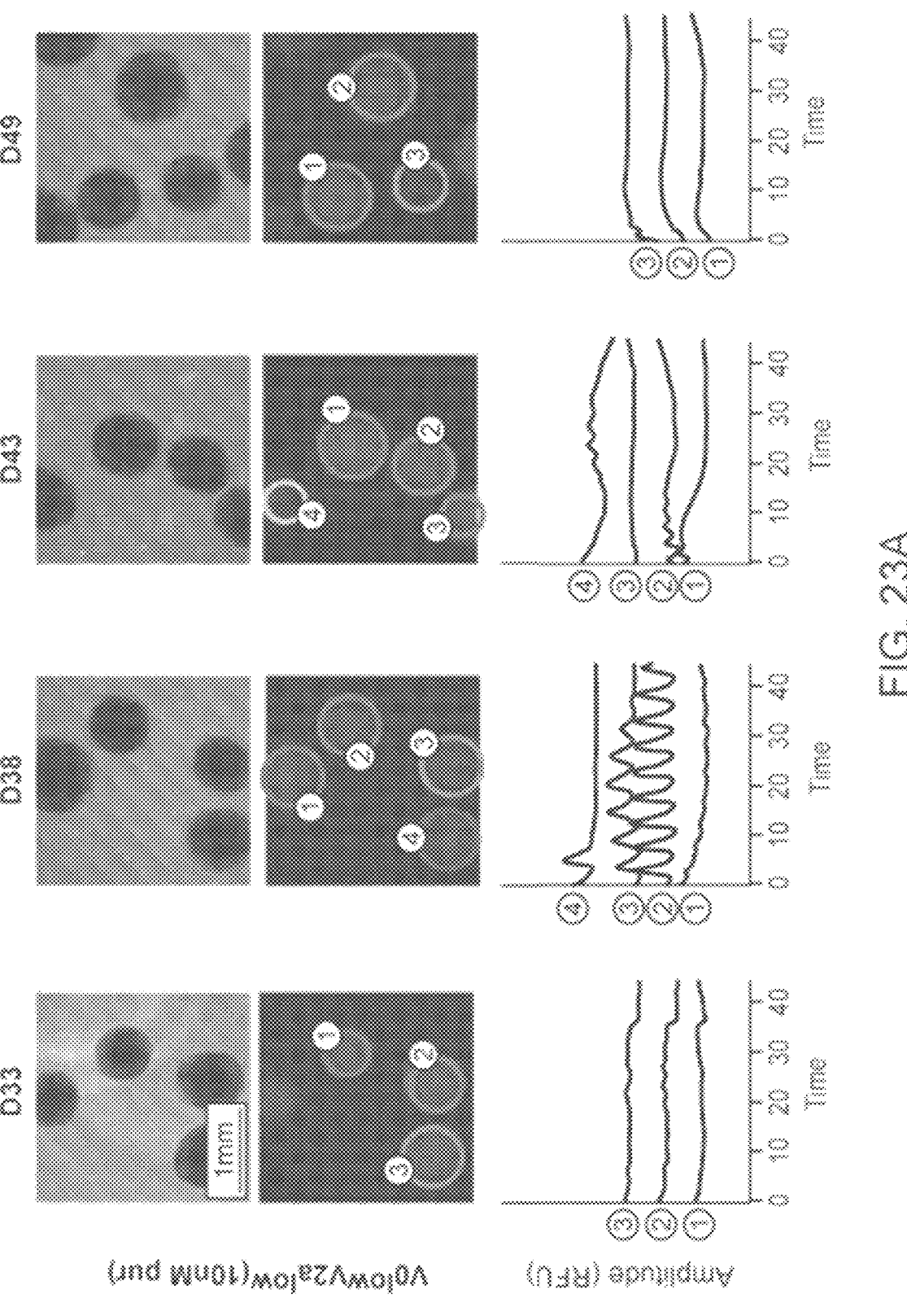
Figure 23B:
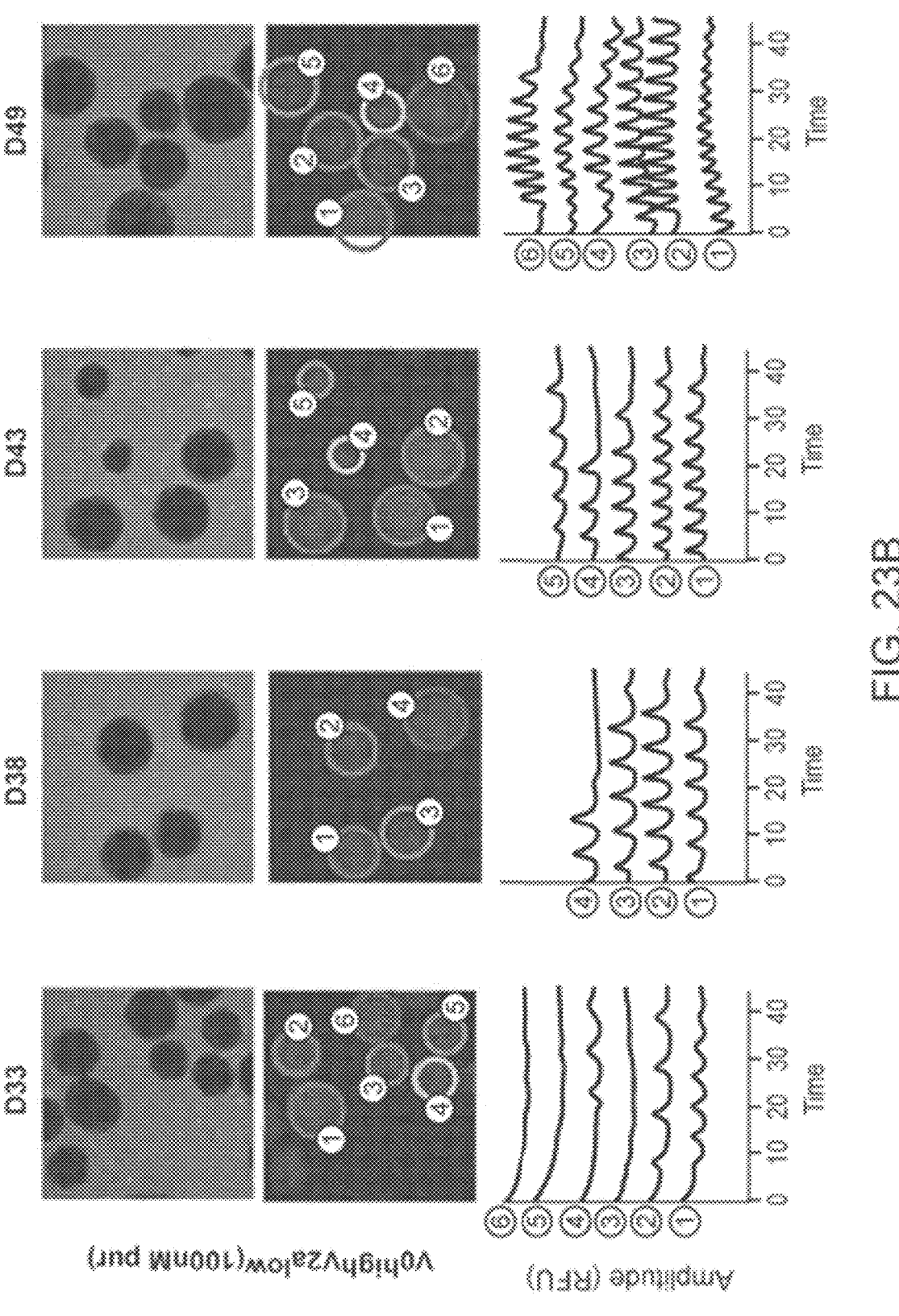
Figure 23C:
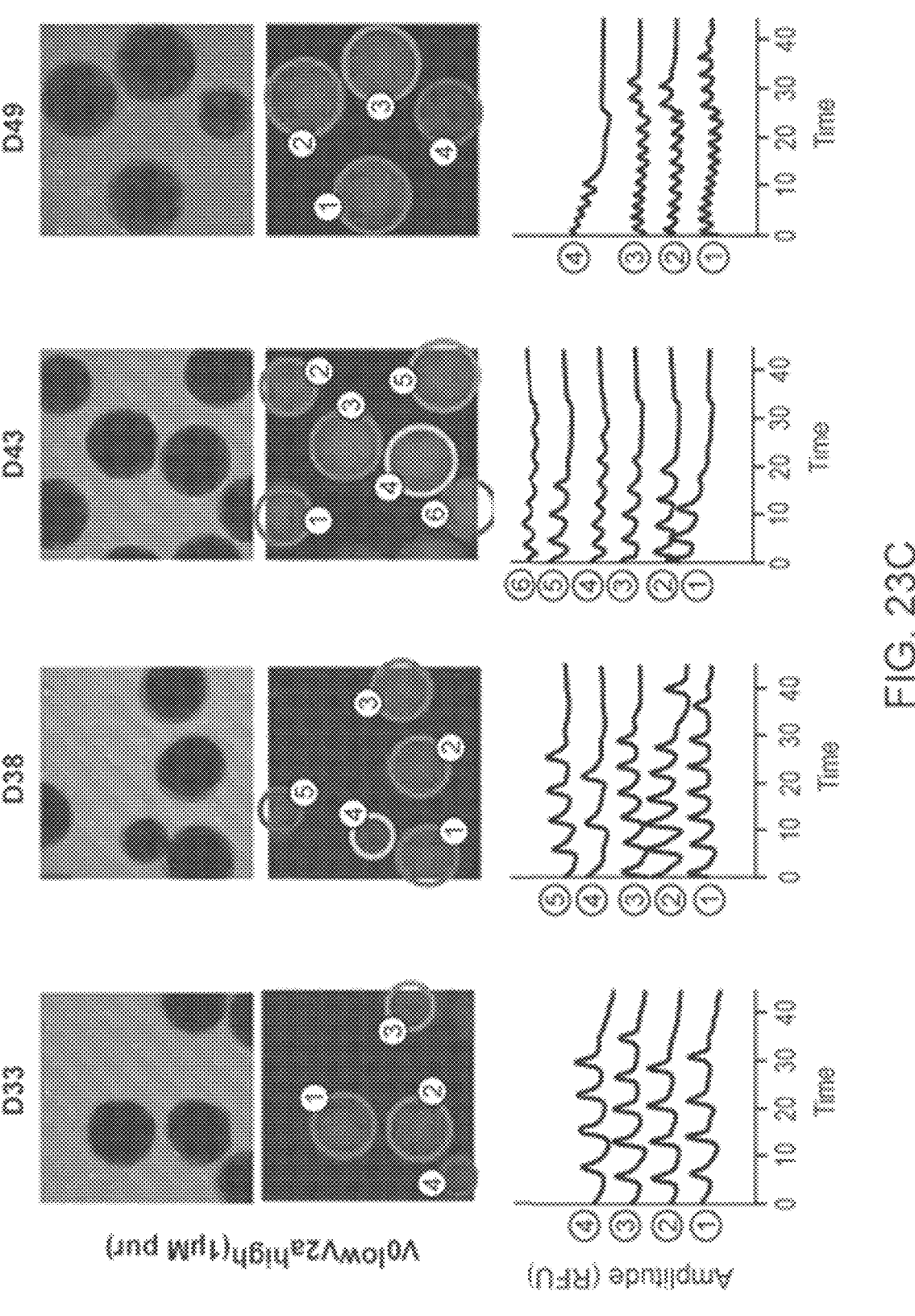

FIGS. 23A-23C show synchronous $Ca^{2+}$ fluctuations in the organoids are dependent on cellular composition. $Ca^{2+}$ transients of a field of organoids at day 33, 38, 43, and 49 in aggregates tested with (FIG. 23A) 10 nM, (FIG. 23B) 100 nM, or (FIG. 23C) 1 μM pur. Circles demarcate regions of interest (ROI).

Figure 24A:
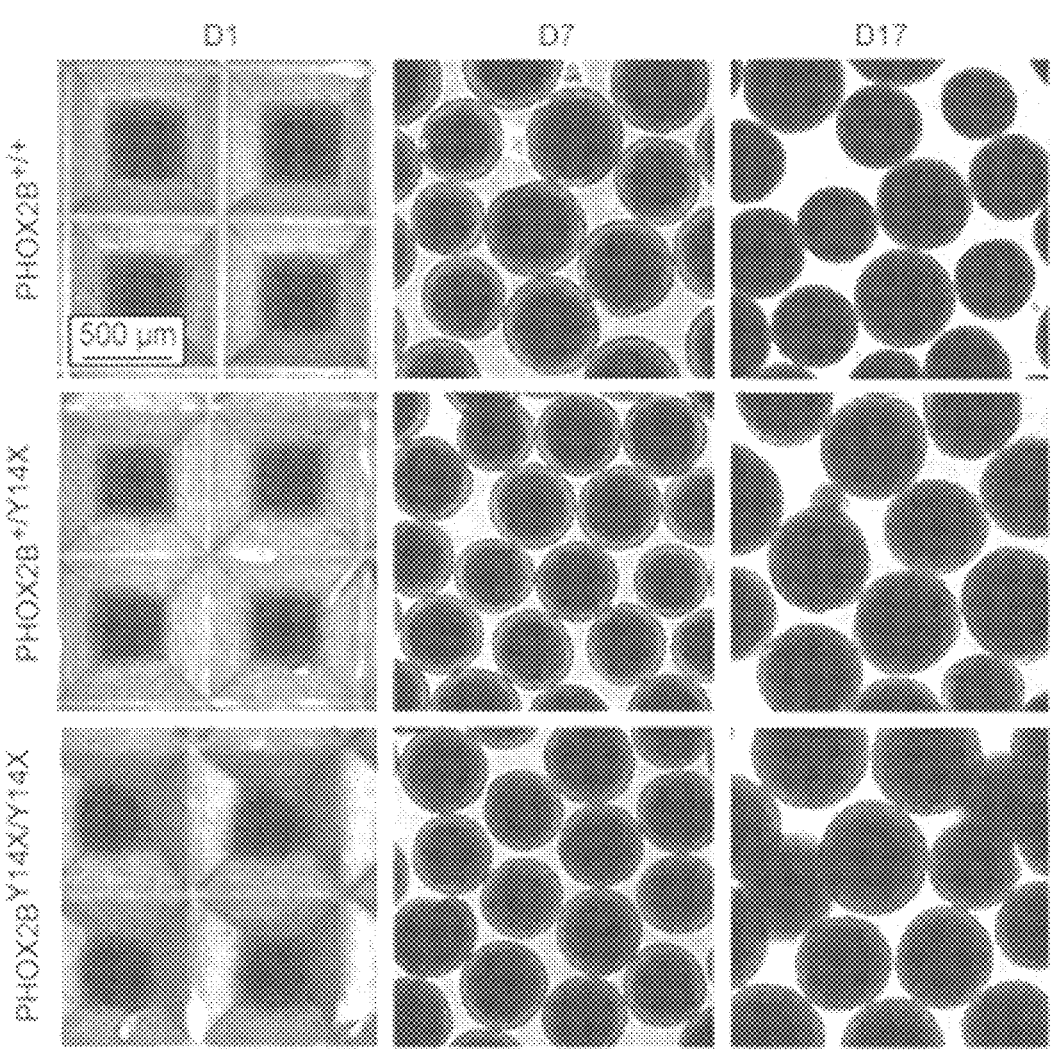
Figure 24B:
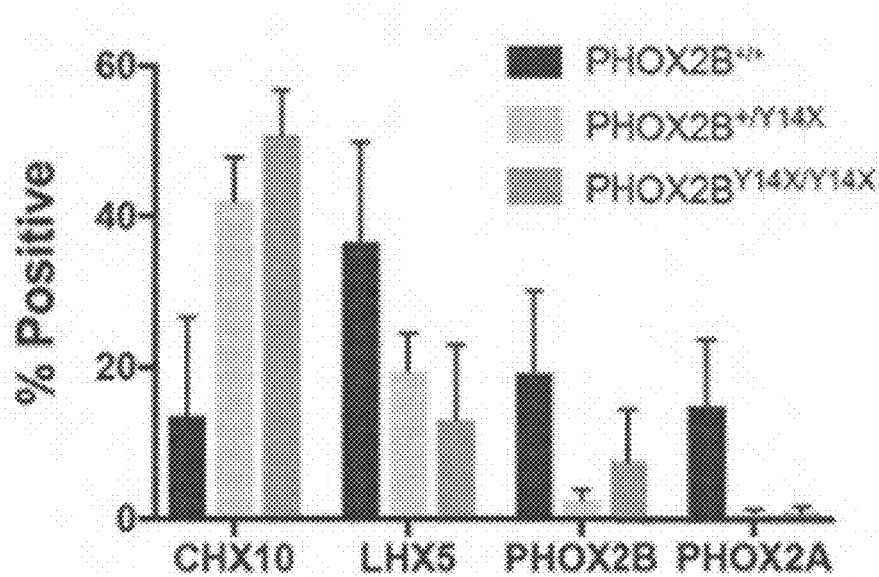
Figure 24C:
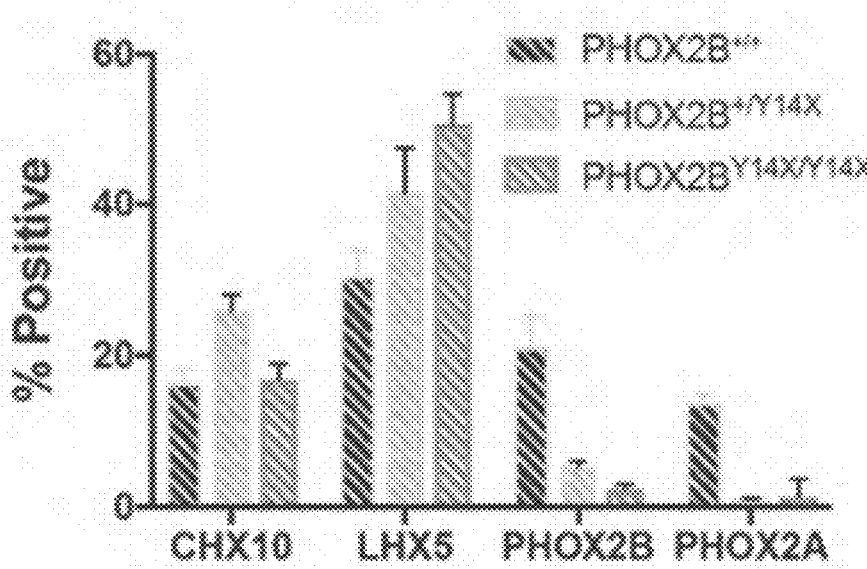
Figure 24D:
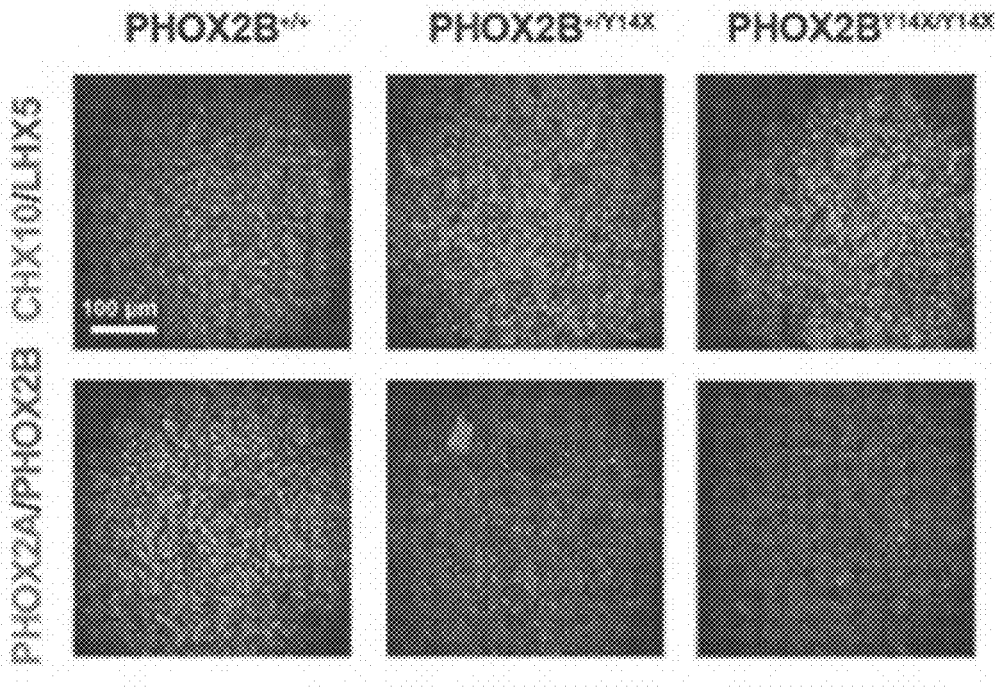

FIGS. 24A-24E show disease modeling in hindbrain organoids. FIG. 24A shows phase contrast images of organoids made from $PHOX2B^{+/+}$, $PHOX2B^{+/Y14X}$, and $PHOX2B^{Y14X/Y14X}$ cell lines. Flow cytometry analysis of CHX10, LHX5, PHOX2B, and PHOX2A from $PHOX2B^{+/+}$, $PHOX2B^{+/Y14X}$, and $PHOX2B^{Y14X/Y14X}$ cell lines in aggregate (FIG. 24B) and monolayer (FIG. 24C) culture. Immunostaining analysis of CHX10, LHX5, PHOX2B, and PHOX2A from $PHOX2B^{+/+}$, $PHOX2B^{+/YH4X}$, and $PHOX2B^{Y14X/Y14X}$ cell lines in aggregate (FIG. 24D) and monolayer (FIG. 24E) culture.

Figure 25A:
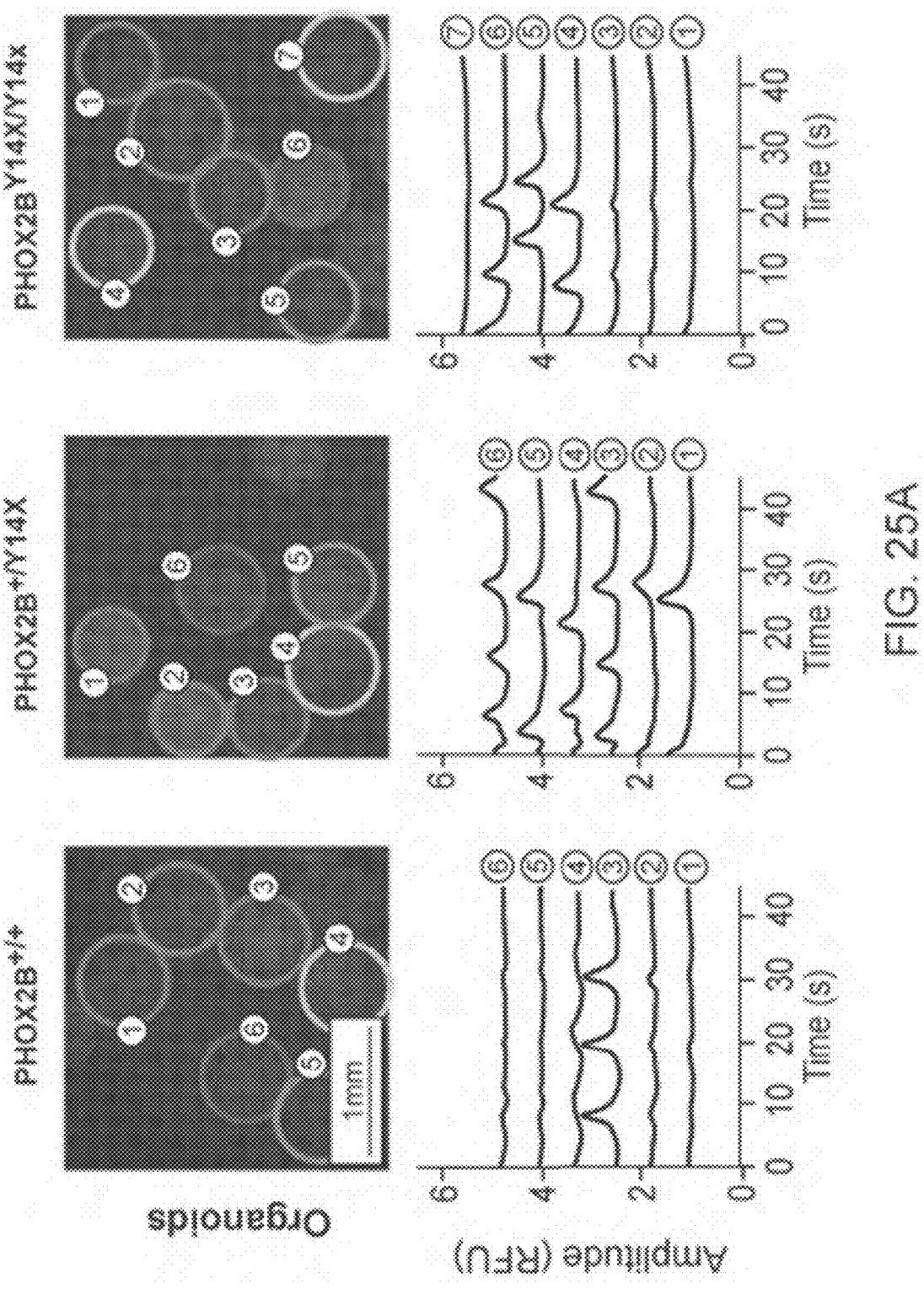
Figure 25B:
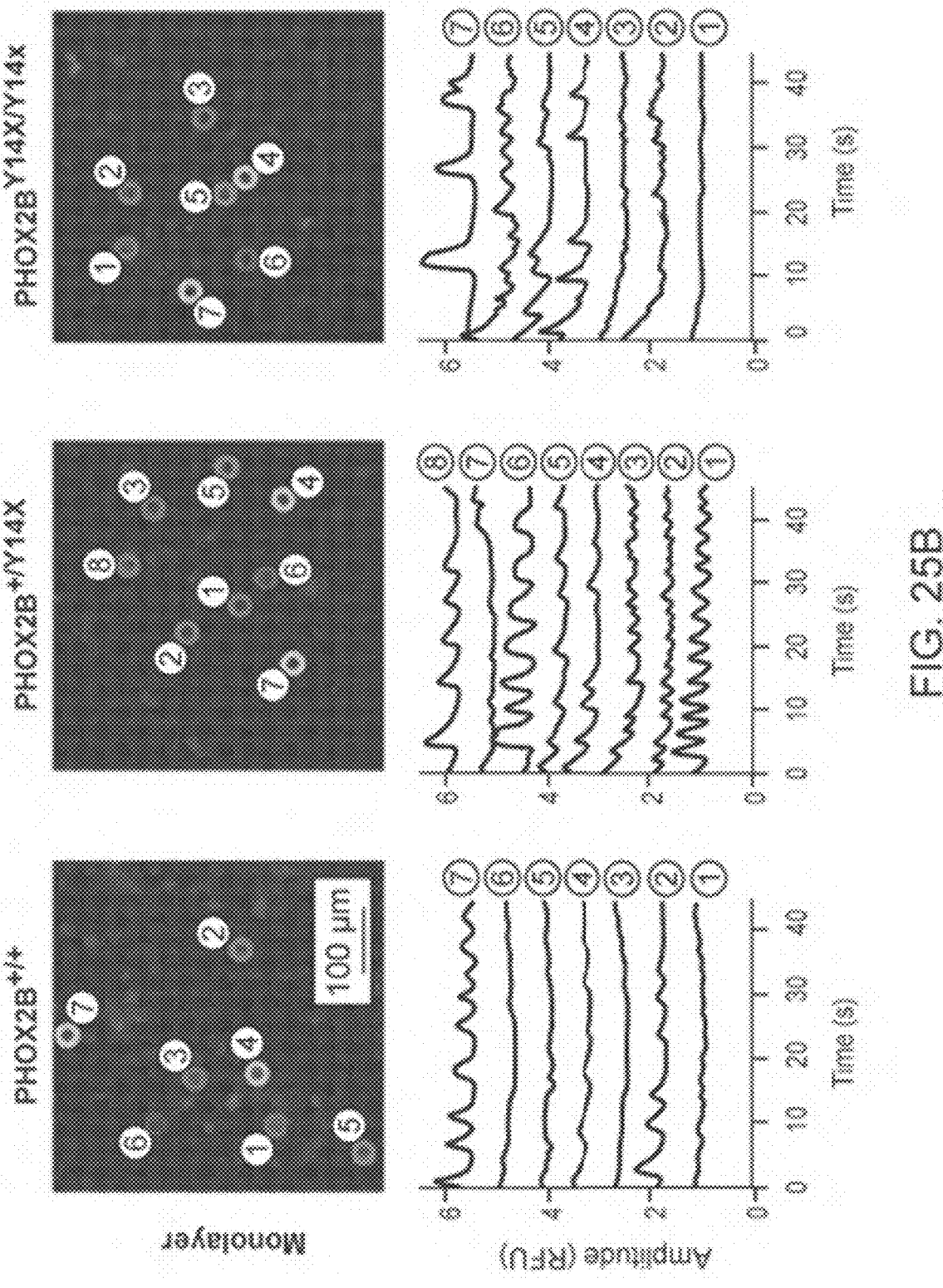

FIGS. 25A-25B show synchronous $Ca^{2+}$ fluctuations in PHOX2B mutant organoids. $Ca^{2+}$ transients of (FIG. 25A) organoids and (FIG. 25B) individual cells in monolayer at day 38 in $PHOX2B^{+/+}$, $PHOX2B^{+/Y14X}$, and $PHOX2B^{Y14X/Y14X}$ cell lines. Colored circles demarcate regions of interest (ROI).

DEFINITIONS

The term "about" as used herein when referring to a measurable value such as an amount, a length, and the like, is meant to encompass variations of ±20% or ±10%, more preferably ±5%, even more preferably ±1%, and still more preferably ±0.1% from the specified value.

The terms "decrease", "reduced", "reduction", "decrease", and "inhibit" are all used herein generally to mean a decrease by a statistically significant amount, including a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase", "enhance" or "activate" are all used herein to generally mean an increase by a statically significant amount, including an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "in vitro" as used herein describes an environment outside of a living body. The environment may be a tissue culture medium inside a flask, dish, or any other suitable container, or may be a body part, tissue, or tissue slice that is in the tissue culture medium.

"Differentiation" refers to a physiological and/or morphological change (e.g., change in gene and/or protein expression pattern, and/or morphology) that occurs in a cell that results in the cell assuming certain specialized functions, also called a cell fate. The change may be an irreversible change, where the differentiated cell loses the ability to assume a different cell fate. The change may be partial or substantially complete with respect to mature adult (e.g., somatic) cells. A partially changed cell may exhibit some of the physiological and/or morphological characteristics of the somatic cell, but may be missing others. A cell may be "committed" to a somatic cell fate when the cell shows at least a partial, substantially irreversible change toward the cell fate, and in some cases, may further develop more of the missing physiological and/or morphological characteristics of the somatic cell without having to provide any differentiation cues. In the case of neurons, in some instances, differentiation may not include axon guidance or other asymmetric developmental changes at the cellular level due to spatial cues acting on a single neuron. Thus, a mature neuron in vitro may not necessarily have neurite branching patterns that resemble the same neuron differentiated and developed in its in vivo context.

"Marker" as used herein, refers to a gene whose expression (RNA transcript expression or protein expression) level is specific to a cell fate, or to a progenitor cell for one or more cell fates. Exemplary neural markers include markers associated with the cortex, retina, cerebellum, brain stem, granular neurons, dopaminergic, and GABAergic neurons. Exemplary cerebellar markers include but are not limited to ATOH1, PAX6, SOX2, LHX2, and GRID2. Exemplary markers of dopaminergic neurons include but are not limited to tyrosine hydroxylase, vesicular monoamine transporter 2 (VMAT2), dopamine active transporter (DAT) and Dopamine receptor D2 (D2R). Exemplary cortical markers include, but are not limited to, doublecortin, NeuN, FOXP2, CNTN4, and TBR1. Exemplary granular neuron markers include, but are not limited to SOX2, NeuroD1, DCX, EMX2, FOXG1, and PROX1. Exemplary brain stem markers include, but are not limited to FGF8, INSM1, GATA2, ASCL1, GATA3. Exemplary spinal cord markers include, but are not limited to homeobox genes including but not limited to HOXA1, A2, A3, B4, A5, C8, or D13. Exemplary GABAergic markers include, but are not limited to NKCC1 or KCC2. Exemplary astrocytic markers include, but are not limited to GFAP. Exemplary oliogodendrocytic markers include, but are not limited to OLIG2 or MBP. Exemplary microglia markers include, but are not limited to AIF1 or CD4. Exemplary vascular markers include, but are not limited to NOS3.

"Morphogen" as used herein, refers to biological signaling molecules that provide spatial and/or temporal cues within a developing organism to direct appropriate differentiation and/or movement of cells for proper development.

"Organoid" as used herein, refers to an organized mass of cell types generated in vitro that mirrors at least to some degree the structure, marker expression, or function of a naturally occurring organ. Organoids may be derived from stem cells (e.g., embryonic stem cells, induced pluripotent stem cells, etc.).

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "stem cell" refers to an undifferentiated cell that can be induced to proliferate. The stem cell is capable of self-maintenance or self-renewal, meaning that with each cell division, at least one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type.

Stem cells include pluripotent stem cells, which can form cells of any of the body's tissue lineages: mesoderm, endoderm and ectoderm. Stem cells can be derived from any organism, including mammals, such as, but not limited to, rats, mice, rabbits, guinea pigs, goats, cows, horses, cats, dogs, non-human primates, and humans. In specific, non-limiting examples, the cells are human, non-human primate, or rodent stem cells. For example, stem cells can be selected from a human embryonic stem (ES) cell; a human inner cell mass (ICM)/epiblast cell; a human primitive ectoderm cell, a human primitive endoderm cell; a human primitive mesoderm cell; and a human primordial germ (EG) cell. Stem cells also include multipotent stem cells, which can form multiple cell lineages that constitute an entire tissue or tissues, such as but not limited to hematopoietic stem cells or neural precursor cells. Stem cells also include totipotent stem cells, which can form an entire organism. In some embodiments, the stem cell is a partially differentiated or differentiating cell. In some embodiments, the stem cell is an induced pluripotent stem cell (iPSC), which has been reprogrammed or de-differentiated.

"Human pluripotent stem cell (hPSC)" refers to a pluripotent stem cell (PSC) that is derived from a human tissue or cell (e.g., a human embryo, a human somatic cell, etc.).

"Expression" refers to detectable production of a gene product by a cell. The gene product may be a transcription product (i.e., RNA), which may be referred to as "gene expression", or the gene product may be a translation product of the transcription product (i.e., a protein), depending on the context.

"Culture" as used herein, refers to growing (i.e., causing to multiply by dividing), maintaining (i.e., keeping the cells alive and/or growing without differentiating) and/or differentiating one or more cells by providing the cells with a suitable environment. The cells may be provided with an in vitro environment (e.g., a suitable cell culture medium) that is conducive for survival, growth, and/or differentiation of the cells. An in vitro environment for growing, maintaining and/or differentiating mammalian cells may include a suitable temperature (e.g., about 37° C.) and a suitable atmosphere (e.g., about 5% CO2, humidified atmosphere) provided by, e.g., an incubator.

"Seed" as used herein, refers to initiating a culture of cells by providing an initial population of cells with a suitable culturing environment (e.g., adding cells to a cell culture medium). In some cases, the cells are initially free-floating and become attached to a cell culture substrate as the cells are cultured.

A "non-human animal model" as used herein may refer to a non-human animal that can be used as a surrogate host for transplanting and developing a cell derived by differentiating a human pluripotent stem cell (hPSC) (e.g., a hPSC-derived cell committed to a V2a interneuron, V0 interneuron, or chemosensing interneuron cell fate).

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an interneuron" includes a plurality of such interneurons and reference to "the organoid" includes reference to one or more organoids and equivalents thereof known to those skilled in the art, and so forth. It is further noted that the may be drafted to exclude any optional element. As such, this statement is intended to serve as antecedent basis for use of such exclusive terminology as "solely," "only" and the like in connection with the recitation of elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication. Further, the dates of publication provided may be different from the actual publication dates which may need to be independently confirmed.

DETAILED DESCRIPTION

As summarized above, provided herein are methods of generating hindbrain cells, including respiratory hindbrain cells, from pluripotent stem cells. Also provided are methods of generating a three-dimensional organoid comprising a population of hindbrain cells comprising a heterogeneous population of interneurons. In particular, methods of generating a heterogeneous population of interneurons comprising V2a interneurons, V0 interneurons, and chemosensing interneurons, or a combination thereof, from pluripotent stem cells (PSCs) and a three-dimensional organoid comprising such interneurons are provided.

Methods of Generating a Population of Hindbrain Cells

A method of the present disclosure may include culturing PSCs in vitro in a neural induction medium that includes a retinoic acid signaling pathway activator (e.g., a retinoic acid receptor agonist, such as retinoic acid), a sonic hedgehog (Shh) signaling pathway activator (e.g., a Smoothened agonist, such as purmorphamine); and a Notch signaling pathway inhibitor (e.g., a γ secretase inhibitor, such as N-[(3,5-difluorophenyl)acetyl]-L-alanyl-2-phenyl]glycine-1,1-dimethylethyl ester (DAPT)), in a manner sufficient to induce differentiation of the PSCs into CHX10-expressing (CHX10+) cells (e.g., CHX10+ V2a interneurons), LHX5-expressing (LHX5+) cells (e.g., LHX5+ V0 interneurons), PHOX2A-expressing (PHOX2A+) cells (e.g., PHOX2A+ chemosensing interneurons), PHOX2B-expressing (PHOX2B+) cells (e.g., PHOX2B+ chemosensing interneurons), or a combination thereof. For the purpose of this disclosure, "PSCs" is meant to include, unless indicated otherwise, PSCs that have at least partially differentiated into hindbrain progenitor cells, e.g., by culturing the population of PSCs in an early differentiation medium, as described herein.

The retinoic acid signaling pathway activator may be any suitable molecule (polypeptide, small molecule, nucleic acid, etc.) that activates the retinoic acid signaling pathway. The retinoic acid signaling pathway may be activated by using agonists of the retinoic acid receptor (RAR) such as retinoic acid. Retinoic acid acts by binding to the retinoic acid receptor (RAR), which is bound to DNA as a heterodimer with the retinoid X receptor (RXR) in regions called retinoic acid response elements (RAREs). Binding of the retinoic acid ligand to RAR alters the conformation of the RAR, which affects the binding of other proteins that either induce or repress transcription of nearby genes, for example of Hox genes. Retinoic acid signaling pathway activators include retinoic acid receptor agonists, such as retinoic acid, and derivatives thereof. Suitable retinoic acid signaling pathway activators include, without limitation, all-trans retinoic acid, synthetic retinoid ec23, Ch55, TTNPB, fenretinide, AC261066, adapalene, AC55649, AM80, AM580, BMS 753, and tazarotene.

The Shh signaling pathway activator may be any suitable molecule (polypeptide, small molecule, nucleic acid, etc.) that activates the Shh signaling pathway. Shh signals by interacting with a plasma membrane complex of Patched (Ptc) and Smoothened (Smo) that transduce the Shh signal into the cell. Ptc is considered to repress Shh signaling by binding to Smo in the cell membrane. In the presence of Shh ligand, this repression is relieved and Smo is able to signal. In vertebrates, the zinc finger proteins GN1, GN2 and GN3 are downstream mediators of Shh signaling and are involved in controlling the transcriptional response of target genes in a Shh dependent manner. Shh signaling pathway activators include Smoothened agonists. Suitable Smoothened agonists include, without limitation, SAG (9-Cyclohexyl-N-[4-(4-morpholinyl)phenyl]-2-(1-naphthalenyloxy)-9H-purin-6-amine); purmorphamine (9-Cyclohexyl-N-[4-(4-morpholinyl)phenyl]-2-(1-naphthalenyloxy)-9H-purin-6-amine); and 20(S)-hydroxycholesterol.

The Notch signaling pathway inhibitor may be any suitable molecule (polypeptide, small molecule, nucleic acid, etc.) that inhibits signaling mediated by activation of a Notch receptor. Ligand-induced activation of Notch results in cleavage at the S2 site by proteases of the ADAM family, releasing the extracellular domain. The remaining truncated transmembrane form of Notch is then subject to cleavage at two sites within the membrane S3 and S4, the targets of γ-secretase. Notch intracellular domain (ICD) translocates to the nucleus where it regulates transcription of Notch target genes. Notch signaling pathway inhibitors include inhibitors of Notch receptor activation, e.g., Notch receptor antagonists. In some cases, the inhibitor of Notch receptor activation is a γ-secretase inhibitor, including, but not limited to, N-[(3,5-difluorophenyl)acetyl]-L-alanyl-2-phenyl]glycine-1,1-dimethylethyl ester (DAPT); N-2((2S)-2-(3,5-difluoro-phenyl)-2-hydroxyethanoyl)-N1-((7S)-5-methyl-6-oxo-6,7-dihydro-5H-dibenzo[b,d] azepin-7-yl)-L-alaninamide (LY411575); L-685,458; BMS-299897; MK0752; and MRK-003. Other inhibitors of the Notch signaling pathway include, without limitation, anti-Notch antibodies and antigen-binding fragments thereof, as well as inhibitory nucleic acids (e.g., small interfering RNAs, antisense oligonucleotides, and morpholino oligos).

The neural induction medium may be any suitable media that promotes differentiation of PSCs into neuronal cell types. The neural induction medium may include a base medium and one or more supplements. Suitable base media include, without limitation, Dulbecco's Modified Eagle's Medium (DMEM), Ham's F12, KODMEM medium (Knockout Dulbecco's Modified Eagle's Medium), RPMI 1640 and MEM. Suitable supplements include, without limitation, N2 supplement, L-glutamine, heparin, non-essential amino acids, antibiotics (e.g., penicillin-streptomycin, ascorbic acid, and brain derived neurotrophic factor (BDNF). Other suitable media include NEUROBASAL™ medium (neural cell culture medium) and NSC™ (Neural Stem Cell culture media) from Life Technologies, PNGM™ (Primary Neuron Growth Medium) from Lonza, Neural Stem Cell basal medium from Millipore and STEMDIFF™ (pluripotent stem cell differentiation media) from StemCell Technologies.

In this paragraph, and throughout the specification, unless the context clearly indicates otherwise, reference to "a" or "the" retinoic acid signaling pathway activator is considered to include as an example thereof a retinoic acid receptor agonist, e.g., retinoic acid. The amount of the retinoic acid signaling pathway activator present in the neural induction medium may be an amount suitable to differentiate PSCs into V2a interneurons, V0 interneurons, and chemosensing interneurons, or a combination thereof. In some cases, the retinoic acid signaling pathway activator is added to the neural induction medium at a known concentration. In some cases, the retinoic acid signaling pathway activator is present in the neural induction medium at a concentration of about 20 nM or more, e.g., about 30 nM or more, about 40 nM or more, including about 50 nM or more, and in some cases of about 500 nM or less, e.g., about 400 nM or less, about 300 nM or less, including about 200 nM or less. In some cases, the retinoic acid signaling pathway activator is present in the neural induction medium at a concentration of from about 20 nM to about 500 nM, e.g., from about 30 nM to about 400 nM, from about 40 nM to about 300 nM, including from about 50 nM to about 200 nM. In some embodiments, the retinoic acid signaling pathway activator is present in the neural induction medium at a concentration of about 100 nM. In some embodiments, the concentration of the retinoic acid signaling pathway activator in the neural induction medium may be different at different times during the culturing.

In this paragraph, and throughout the specification, unless the context clearly indicates otherwise, reference to "a" or "the" Shh signaling pathway activator is considered to include as an example thereof a Smoothened agonist, e.g., purmorphamine. The amount of the Shh signaling pathway activator present in the neural induction medium may be an amount suitable to differentiate PSCs into V2a interneurons, V0 interneurons, and chemosensing interneurons, or a combination thereof. In some cases, the Shh signaling pathway activator is added to the neural induction medium at a known concentration. In some cases, the Shh signaling pathway activator is present in the neural induction medium at a concentration of about 20 nM or more, e.g., about 30 nM or more, about 40 nM or more, including about 50 nM or more, 100 nM or more, 500 nM or more, 1 μM or more, 5 μM or more, 10 μM or more, and in some cases of about 10 μM or less, e.g., about 10 μM or less, about 5 μM or less, about 1 μM or less, about 500 nM or less, about 400 nM or less, about 300 nM or less, about 250 nM or less, about 225 nM or less, about 200 nM or less, about 175 nM or less, including about 150 nM or less. In some cases, the Shh signaling pathway activator is present in the neural induction medium at a concentration of from about 20 nM to about 5 μM, e.g., from about 30 nM to about 400 nM, from about 30 nM to about 300 nM, from about 40 nM to about 250 nM, from about 40 nM to about 225 nM, from about 40 nM to about 200 nM, from about 50 nM to about 175 nM, from about 500 nM to about 2 μM, from about 750 nM to about 1 μM, including from about 50 nM to about 150 nM. In some embodiments, the Shh signaling pathway activator is present in the neural induction medium at a concentration of about 100 nM. In some embodiments, the Shh signaling pathway activator is present in the neural induction medium at a concentration of about 1 μM. In some embodiments, the concentration of the Shh signaling pathway activator in the neural induction medium may be different at different times during the culturing.

In this paragraph, and throughout the specification, unless the context clearly indicates otherwise, reference to "a" or "the" Notch signaling pathway inhibitor is considered to include as an example thereof a γ secretase inhibitor, e.g., DAPT. The amount of the Notch signaling pathway inhibitor present in the neural induction medium may be an amount suitable to differentiate PSCs into V2a interneurons, V0 interneurons, and chemosensing interneurons, or a combination thereof. In some cases, the Notch signaling pathway inhibitor is added to the neural induction medium at a known concentration. In some cases, the Notch signaling pathway inhibitor is present in the neural induction medium at a concentration of about 250 nM or more, e.g., about 350 nM or more, about 500 nM or more, about 750 nM or more, 900 nM or more, about 1 μM or more, 5 μM or more, about 10 UM or more, and in some cases, about 10 μM or less, e.g., about 5.0 μM or less, about 3.0 μM or less, including about 2.0 μM or less. In some cases, the Notch signaling pathway inhibitor is present in the neural induction medium at a concentration of from about 250 nM to about 10 μM, e.g., from about 350 nM to about 5.0 μM, from about 500 nM to about 5.0 μM, including from about 750 nM to about 3.0 μM. In some embodiments, the Notch signaling pathway inhibitor is present in the neural induction medium at a concentration of about 1 μM. In some embodiments, the concentration of the Notch signaling pathway inhibitor in the neural induction medium may be different at different times during the culturing.

Culturing the PSCs in a neural induction medium, according to methods of the present disclosure, may include using multiple neural induction media over the time course of differentiating the PSCs. Aspects of the culturing may include contacting a population of PSCs with a first neural induction medium that includes a retinoic acid signaling pathway activator for a first time period, then contacting the cells with a second neural induction medium that includes the retinoic acid signaling pathway activator, a Shh signaling pathway activator, and a Notch signaling pathway inhibitor for a second time period. Aspects of the culturing may include contacting a population of PSCs with a first neural induction medium that includes a retinoic acid signaling pathway activator but not a Shh signaling pathway activator for a first time period, then contacting the cells with a second neural induction medium that includes the retinoic acid signaling pathway activator and the Shh signaling pathway activator for a second time period, and then contacting the cells with a third neural induction medium that includes the retinoic acid signaling pathway activator, the Shh signaling pathway activator, and the Notch signaling pathway inhibitor. Aspects of the culturing may further include contacting a population of PSCs with a WNT signaling pathway activator.

In some embodiments, the Notch signaling pathway inhibitor is added to the neural induction medium after initiating the differentiation of PSCs using the retinoic acid signaling pathway activator. Thus, in some cases, the Notch signaling pathway inhibitor is not added to the first neural induction medium, and is added to the second neural induction medium together with the Shh signaling pathway activator. In other words, in some embodiments, culturing PSCs includes contacting a population of PSCs with a first neural induction medium that includes a retinoic acid signaling pathway activator but not a Shh signaling pathway activator or a Notch signaling pathway inhibitor for a first time period, then contacting the cells with a second neural induction medium that includes the retinoic acid signaling pathway activator, the Shh signaling pathway activator, and the Notch signaling pathway inhibitor for a second time period.

One or more of the neural induction media described herein may include a WNT signaling activator, e.g., a small molecule WNT signaling activator, such as a GSK3 inhibitor, such as a small molecule GSK3 inhibitor, e.g., CHIR99021 (6-[[2-[4-(2,4-Dichlorophenyl)-5-(5-methyl-1H-imidazol-2-yl)-2-pyrimidinyl]amino]ethyl]amino]-3-pyridinecarbonitrile). Additional WNT signaling activators which may be used in connection with the disclosed methods include: CHIR 99021 trihydrochloride (6-[2-[4-(2,4-Dichlorophenyl)-5-(5-methyl-1H-imidazol-2-yl)-2-pyrimidinyl]amino]ethyl]amino]-3-pyridinecarbonitrile trihydrochloride), WAY-316606 (5-(Phenylsulfonyl)-N-4-piperidinyl-2-(trifluoromethyl)benzene sulfonamide hydrochloride), (hetero) arylpyrimidines, IQ1 (2-[2-(4-Acetylphenyl)diazenyl]-2-(3,4-dihydro-3,3-dimethyl-1 (2H)-isoquinolinylidene) acetamide), QS11 ((2S)-2-[2-(Indan-5-yloxy)-9-(1,1'-biphenyl-4-yl)methyl]-9H-purin-6-ylamino]-3-phenyl-propan-1-ol), SB-216763 (3-(2,4-Dichlorophenyl)-4-(1-methyl-1H-indol-3-yl)-1H-pyrrole-2,5-dione), BIO (6-bromoindirubin-3'-oxime), LY2090314 (3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione), DCA (Sodium dichloroacetate), 2-amino-4-[3,4-(methylenedioxy)benzyl-amino]-6-(3-methoxyphenyl) pyrimidine. The WNT signaling activator may be present in any suitable concentration in the neural induction medium and may be introduced at any suitable time during the differentiation. For example, the WNT signaling activator may be present in the neural induction medium at a concentration of from about 0.1 μM to about 10 μM, e.g., from about 1 μM to about 5 μM, such as about 2 μM. Use of a WNT signaling activator may be of interest, for example, when it is desired to shift the rostral/caudal identity of the cell population, e.g., to increase the percentage of cells exhibiting a caudal phenotype. In addition, the introduction of a WNT signaling activator appears to increase the percentage of CHX10$^+$ cells, LHX5$^+$ cells, PHOX2A/B$^+$ cells, or a combination thereof, in the population.

In some embodiments, the Notch signaling pathway inhibitor is added to the neural induction medium after initiating the differentiation of the PSCs using the retinoic acid signaling pathway activator and the Shh signaling pathway activator. Thus, in some cases, the Notch signaling pathway inhibitor is not added to the first or the second neural induction media, and is added to the third neural induction medium. In some embodiments, the Notch signaling pathway inhibitor is added to the neural induction medium at the same time as the retinoic acid signaling pathway activator is added to the neural induction medium. Thus, in some cases, the Notch signaling pathway inhibitor is added to the first and the second neural induction media.

"Contacting" may refer to any suitable method of immersing and/or exposing a population of cells growing on a substrate, or in suspension, with the medium. In some cases, the contacting includes adding the medium to a compartment that includes the population of cells, and leaving the cells in the medium for the period of time. In some cases, the contacting includes continuously adding the medium to the compartment that includes the population of cells, e.g., as a flow of the medium over the cells.

The first time period, e.g., as set out in any embodiment set forth herein, and specifically those set forth above, may be about one day or more, e.g., about 2 days or more, including about 3 days or more, and in some cases, may be about 1 day, about 2 days, or about 3 days. The second time period, e.g., as set out in any embodiment set forth herein, and specifically those set forth above, may be about one day or more, e.g., about 2 days or more, about 3 days or more, about 4 days or more, about 5 days or more, about 6 days or more, about 7 days or more, about 8 days or more, about 9 days or more, including about 10 days or more, and in some cases, may be about 1 day, about 2 days, about 3 days, about 4 days, about 5 days, about 6 days, about 7 days, about 8 days, about 9 days, or about 10 days. The third time period, e.g., as set out in any embodiment set forth herein, and specifically those set forth above, may be about 5 days or more, e.g., about 6 days or more, including about 7 days or more, and in some cases, may be about 5 days, about 6 days, or about 7 days. In some embodiments, the first time period is about 2 days, the second time period is about 3 days, and the third time period is about 7 days.

The culturing in the neural induction medium (i.e., all of the one or more neural induction media) may take any suitable total number of days to differentiate the PSCs into the V2a interneurons, V0 interneurons, and chemosensing interneurons, or a combination thereof, according to the methods disclosed herein. In some cases, the PSCs are cultured in the neural induction medium for about 7 days or more, e.g., about 9 days or more, about 11 days or more, 13 days or more, 15 days or more, about 17 days or more, about 19 days or more, and in some cases, about 19 days or less, e.g., including about 19 days or less, about 17 days or less, about 16 days or less, about 15 days or less, about 14 days or less, about 13 days or less, or about 12 days or less. In some embodiments, the hPSCs are cultured in the neural induction medium for from about 7 days to about 13 days, e.g., from about 9 days to about 13 days, including about 11 days to about 13 days. In some embodiments, the PSCs are cultured in the neural induction medium for about 12 days.

Culturing the PSCs, according to aspects of the present disclosure, may further include any suitable methods for promoting differentiation of a population of PSCs into neural ectoderm progenitor cells (i.e., progenitor cells that can give rise to neuronal cell types and progenitors thereof, including progenitor cells that can give rise to spinal cord neuron progenitors). In general, this may involve inhibiting signaling of the Small Mothers Against Decapentaplegic (SMAD) signaling pathway in the PSCs. Thus, the present methods may include, in addition to the steps discussed previously herein, culturing PSCs in conditions sufficient to promote neural ectoderm differentiation of the PSCs, by adding one or more, e.g., two or more, SMAD signaling pathway inhibitor to the medium in which the PSCs are cultured. In some cases, the SMAD signaling pathway inhibitor(s) is/are added to the neural induction medium. In some embodiments, the neural induction medium (e.g., the first neural induction medium) includes the SMAD signaling pathway inhibitor(s) and the retinoic acid signaling pathway activator (e.g., a retinoic acid receptor agonist, such as retinoic acid), but not the Shh signaling pathway activator. In some embodiments, the method includes culturing the hPSCs in an early differentiation medium that includes the SMAD signaling pathway inhibitor(s), but does not include the retinoic acid signaling pathway activator, the Shh signaling pathway activator or the Notch signaling pathway inhibitor.

The early differentiation medium may be any suitable medium to promote differentiation of the PSCs into neural ectoderm progenitor cells. In some cases, the early differentiation medium is a serum-free defined medium for feeder-free culture of stem cells. The early differentiation medium may be mTeSR 1, KSR (Invitrogen), or xeno-free KSR (Invitrogen), StemPro (Invitrogen) and HEScGRO (Millipore), DMEM based media, and the like. The early differentiation medium may include an inhibitor of p160-Rho-associated coiled kinase (ROCK). The ROCK inhibitor may be any suitable inhibitor of the kinase, such as, but not limited to, Y-27632.

The SMAD signaling pathway inhibitor(s) may be any suitable molecule (polypeptide, small molecule, nucleic acid, etc.) that inhibits SMAD signaling pathways. In some cases, the SMAD signaling pathway inhibitor includes an inhibitor of activin receptor-like kinases (ALKs), such as, but not limited to, LDN193189, SB431542, or a combination thereof. In some embodiments, the SMAD signaling pathway inhibitors comprise LDN193189, dorsomophorine, or noggin, and SB431542.

The early differentiation medium may include a WNT signaling activator, e.g., a small molecule WNT signaling activator, such as a GSK3 inhibitor, such as a small molecule GSK3 inhibitor, e.g., CHIR99021 (6-[[2-[[4-(2,4-Dichlorophenyl)-5-(5-methyl-1H-imidazol-2-yl)-2-pyrimidinyl] amino]ethyl]amino]-3-pyridinecarbonitrile). This may be alternatively or in addition to its inclusion in the neural induction medium as described herein. Additional WNT signaling activators which may be used in connection with the disclosed methods include: CHIR 99021 trihydrochloride (6-[2-[4-(2,4-Dichlorophenyl)-5-(5-methyl-1H-imidazol-2-yl)-2-pyrimidinyl]amino]ethyl]amino]-3-pyridinecarbonitrile trihydrochloride), WAY-316606 (5-(Phenylsulfonyl)-N-4-piperidinyl-2-(trifluoromethyl) benzene sulfonamide hydrochloride), (hetero) arylpyrimidines, IQ1 (2-[2-(4-Acetylphenyl)diazenyl]-2-(3, 4-dihydro-3,3-dimethyl-1 (2H)-isoquinolinylidene) acet-amide), QS11 ((2S)-2-[2-(Indan-5-yloxy)-9-(1,1'-biphenyl-4-yl)methyl]-9H-purin-6-ylamino]-3-phenyl-propan-1-ol), SB-216763 (3-(2,4-Dichlorophenyl)-4-(1-methyl-1H-indol-3-yl)-1H-pyrrole-2,5-dione), BIO (6-bromoindirubin-3'-oxime), LY2090314 (3-(9-fluoro-2-(piperidine-1-carbonyl)-1, 2,3,4-tetrahydro-[1,4]diazepino[6,7,1-hi]indol-7-yl)-4-(imidazo[1,2-a]pyridin-3-yl)-1H-pyrrole-2,5-dione), DCA (Sodium dichloroacetate), 2-amino-4-[3,4-(methylenedioxy)benzyl-amino]-6-(3-methoxyphenyl) pyrimidine. The WNT signaling activator may be present in any suitable concentration in the early differentiation medium and may be introduced at any suitable time during the differentiation. For example, the WNT signaling activator may be present in the early differentiation medium at a concentration of from about 0.1 μM to about 10 μM, e.g., from about 1 μM to about 5 M, such as about 2 μM. Use of a WNT signaling activator may be of interest, for example, when it is desired to shift the rostral/caudal identity of the cell population, e.g., to increase the percentage of cells exhibiting a caudal phenotype. In addition, the introduction of a WNT signaling activator appears to increase the percentage of CHX10" cells in the population.

For example, a suitable early differentiation medium protocol may include seeding PSCs at a high density, e.g., about 100K cells/cm$^2$ to about 150K cells/cm$^2$, such as about 110K cells/cm$^2$ to about 130K cells/cm$^2$, such as about 120K cells/cm$^2$, in the presence of a WNT signaling activator, e.g., a WNT signaling activator as described herein, e.g., at a concentration as described herein. The early differentiation medium protocol may include a step of dissociating and replating the cells at a lower density, e.g., about 15K cells/cm$^2$ to about 30K cells/cm$^2$, such as about 25K cells/cm$^2$. The culturing protocol may then proceed as otherwise described herein. In some embodiments, replating the cells is performed in order to enrich for V2a interneurons.

Culturing in the PSCs in the early differentiation medium may be continued for any suitable amount of time to promote differentiation of a population of PSCs into neural ectoderm progenitor cells. In some cases, the PSCs are cultured in the early differentiation medium for about 4 to about 6 days, such as about 5 days.

The total time the PSCs are cultured in vitro (i.e., the total time in the early differentiation medium and one or more neural induction media) to generate a population of V2a interneurons may vary, depending on the length of time the cells are cultured in each medium. In some embodiments, the total time the PSCs are cultured in vitro is about 13 days or more, e.g., about 15 days or more, about 16 days or more, about 17 days or more, or about 19 days or more, and in some cases, about 25 days or less, e.g., about 23 days or less, about 21 days or less, about 19 days or less, about 18 days or less, or about 17 days or less. In some embodiments, the hPSCs are cultured in vitro in the early differentiation medium and one or more neural induction media for a total of from about 13 days to about 25 days, e.g., from about 15 days to about 23 days, from about 15 days to about 21 days, from about 15 days to about 19 days, including from about 16 days to about 18 days, wherein exposure to the early differentiation medium and the one or more neural induction media may be for sequential or co-extensive periods of time. In some embodiments, the hPSCs are cultured in the early differentiation medium and one or more neural induction media for about 17 days, wherein exposure to the early differentiation medium and the one or more neural induction media may be for sequential or co-extensive periods of time.

Culturing the PSCs, according to any of the methods of the present disclosure, may include seeding the culture (e.g., a cell culture substrate) with an initial population of PSCs. Thus, once seeded, the culturing of the PSCs to induce differentiation of V2a interneurons, V0 interneurons, che-
mosensing interneurons, or a combination thereof (including
promoting differentiation of the neural ectoderm progeni-
tors) may not involve dissociating the cells from the cell
culture substrate, once the cells are seeded and attached to
the cell culture substrate. The initial population of PSCs may
include any suitable number of PSCs to obtain a suitable
density of PSCs on the substrate. In some cases, the PSCs
are seeded on the cell culture substrate at a density of 5,000
cells/cm$^2$ or more, e.g., 10,000 cells/cm$^2$ or more, 15,000
cells/cm$^2$ or more, including 20,000 cells/cm$^2$ or more, and
in some cases, at a density of 120,000 cells/cm$^2$ or less, e.g.,
100,000 cells/cm$^2$ or less, 80,000 cells/cm$^2$ or less, 60,000
cells/cm$^2$ or less, 40,000 cells/cm$^2$ or less, including 30,000
cells/cm$^2$ or less. In some embodiments, the PSCs are seeded
on the cell culture substrate at a density of from 5,000
cells/cm$^2$ to 120,000 cells/cm$^2$, e.g., from 10,000 cells/cm$^2$
to 100,000 cells/cm$^2$, from 15,000 cells/cm$^2$ to 60,000 cells/
cm$^2$, including from 20,000 cells/cm$^2$ to 30,000 cells/cm$^2$,
e.g., about 25,000 cells/cm$^2$.

A further aspect of the present disclosure includes an in
vitro method for inducing maturation of the V2a interneu-
rons, V0 interneurons, chemosensing interneurons, or a
combination thereof, generated from hPSCs in the neural
induction medium (e.g., the population of CHX10+V2a
interneurons after culturing in the last of multiple neural
induction media, as described above), by reseeding cells of
the population of cells that includes the V2a interneurons,
V0 interneurons, chemosensing interneurons, or a combina-
tion thereof, onto another substrate (e.g., a neural maturation
substrate), and culturing the seeded cells in a neural matu-
ration medium. The reseeding may include dissociating the
cells from the substrate (i.e., the neural induction substrate)
on which the PSCs were differentiated by exposure to the
neural induction medium, using any suitable method. The
cells may be dissociated, by, without limitation, enzymatic
and/or mechanical dissociation methods.

The population of cells that includes the V2a interneu-
rons, V0 interneurons, chemosensing interneurons, or a
combination thereof, derived from PSCs may be reseeded at
any suitable density. In some embodiments, the cells are
reseeded at a density of about 50,000 cells/cm$^2$ to about
150,000 cells/cm$^2$, such as at about 100,000 cells/cm$^2$.

The maturation process may also include culturing the
reseeded cells in the neural induction medium that includes
the retinoic acid signaling pathway activator (e.g., a retinoic
acid receptor agonist, such as retinoic acid), the Shh signal-
ing pathway activator (e.g., a Smoothened agonist, such as
purmorphamine); and the Notch signaling pathway inhibitor
(e.g., a γ secretase inhibitor, such as DAPT), as well as a
ROCK inhibitor, such as Y-27632, for a time period before
culturing in the neural maturation medium. Thus, in some
cases, methods of the present disclosure includes, after
generating a population of cells that include V2a interneu-
rons, V0 interneurons, and chemosensing interneurons, or a
combination thereof, from PSCs in the neural induction
medium, reseeding the population of cells onto a substrate,
contacting the reseeded cells with a neural induction
medium with the retinoic acid signaling pathway activator,
the Shh signaling pathway activator, the Notch signaling
pathway inhibitor, and the ROCK inhibitor, and followed by
contacting with the neural maturation medium. The reseeded
cells may be left in the neural induction medium for any
suitable length of time, and in some cases may be in the
neural induction medium for about 2 to 4 days, such as about
3 days. The cells may be in the neural maturation medium
for any suitable length of time to induce maturation of the V2a interneurons, V0 interneurons, chemosensing interneu-
rons, or a combination thereof, and in some cases may be in
the neural induction medium for about 20 days or more, e.g.,
about 25 days or more, about 30 days or more, about 40 days
or more, about 50 days or more, about 60 days or more,
including about 100 days or more.

The neural maturation medium may be any suitable
medium for promoting maturation of the V2a interneurons,
V0 interneurons, and chemosensing interneurons, or a com-
bination thereof. Suitable media include, without limitation,
NEUROBASAL™ medium (neural cell culture medium)
and NSC™ (Neural Stem Cell culture media) from Life
Technologies, PNGM™ (Primary Neuron Growth Medium)
from Lonza, Neural Stem Cell basal medium from Millipore
and STEMDIFF™ (pluripotent stem cell differentiation
media) from StemCell Technologies. The neural maturation
medium may be supplemented with any suitable supple-
ments, such as, without limitation, B27 supplement, and
neuronal growth factors. Suitable growth factors include,
without limitation, BDNF, glial cell line-derived neuro-
trophic factor (GDNF), ciliary neurotrophic factor (CNTF),
and insulin-like growth factor (IGF).

The PSCs may be cultured in vitro using any suitable cell
culture substrate for differentiating PSCs into V2a interneu-
rons, V0 interneurons, chemosensing interneurons, or a
combination thereof. In some cases, the substrate is a
substantially flat, two-dimensional substrate, e.g., a surface
of a culture flask. The substrate may be of any suitable
material for culturing cells, e.g., plastic, such as polystyrene;
glass; etc. Alternatively, any suitable three-dimensional sub-
strate, such as a hydrogel, porous scaffold, etc., may be used.
In some embodiments, the substrate is coated with a suitable
coating material for promoting PSC differentiation into V2a
interneurons, V0 interneurons, chemosensing interneurons,
or a combination thereof. In some cases, the substrate is
coated with extracellular matrix components, such as, but
not limited to, Matrigel®, fibronectin, laminin. In some
cases, the substrate may include a coating of, without
limitation, polyornithine, poly-lysine, purified collagen,
gelatin, fibronectin, tenascin, vitronectin, entactin, heparin
sulfate proteoglycans, poly glycolytic acid (PGA), poly
lactic acid (PLA), and poly lactic-glycolic acid (PLGA). The
PSCs may be cultured in adherent or suspension cell culture.
For example, in some embodiments the PSCs may be
cultured as an adherent monolayer. The PSCs may also be
cultured as 3-D cell aggregates in a suitable cell culture
suspension, e.g., in the absence of a scaffold material.

PSCs can be derived from any organism, including mam-
mals, such as, but not limited to, rats, mice, rabbits, guinea
pigs, goats, cows, horses, cats, dogs, non-human primates,
and humans. In specific, non-limiting examples, the cells are
human, non-human primate, or rodent stem cells. Pluripo-
tent stem cells can differentiate into cells of any of the
body's tissue lineages including mesoderm, endoderm and
ectoderm.

In some embodiments, the PSCs are human PSCs (hP-
SCs). The hPSCs may be any suitable hPSCs for use in
methods of the present disclosure. In some cases, the hPSCs
are human embryonic stem cells (ESCs). Suitable human
ESCs include, but are not limited to, any of a variety of
available human ES lines, e.g., BG01 (hESBGN-01), BG02
(hESBGN-02), BG03 (hESBGN-03) (BresaGen, Inc.; Ath-
ens, Ga.); SA01 (Sahlgrenska 1), SA02 (Sahlgrenska 2)
(Cellartis AB; Goeteborg, Sweden); ES01 (HES-1), ES01
(HES-2), ES03 (HES-3), ES04 (HES-4), ES05 (HES-5),
ES06 (HES-6) (ES Cell International; Singapore); UC01
(HSF-1), UC06 (HSF-6) (University of California, San Francisco; San Francisco, Calif.); WA01 (H1), WA07 (H7), WA09 (H9), WA09/Oct4D10 (H9-hOct4-pGZ), WA13 (H13), WA14 (H14) (Wisconsin Alumni Research Foundation; WARF; Madison, Wis.). Cell line designations are given as the National Institutes of Health (NIH) code, followed in parentheses by the provider code. Embodiments of interest include any method as otherwise described herein for use in connection with H7 ESCs or H1 ESCs.

In some cases, the PSCs are induced pluripotent stem (iPS) cells, which are a pluripotent stem cell induced from a somatic cell, e.g., a differentiated somatic cell. The iPS cells are capable of self-renewal and differentiation into cell fate-committed stem cells, including neural stem cells, as well as various types of mature cells. Such iPS cells can be generated from somatic cells, including skin fibroblasts, using any suitable method. For example, iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and Klf4. In some embodiments, somatic cells are genetically modified with one or more expression constructs comprising nucleotide sequences encoding Oct-4, Sox2, Nanog, and LIN28. Suitable protein transduction methods may also be utilized, e.g., as an alternative to nucleic acid and/or virally based methods. Suitable iPS cells include human iPS cells such as WTC iPSC and WTB iPSC. Embodiments of interest include any method as otherwise described herein for use in connection with WTC iPSC and WTB iPSC.

PSC-Derived Interneurons

The population of cells generated by the present methods includes cells that express at least one marker specific for V2a interneurons, V0 interneurons, and chemosensing interneurons, or a combination thereof, and may be distinguished from other interneurons or undifferentiated PSCs based on the expression levels of one or more genes (i.e., based on one or more markers). The "interneuron" as used in the context of PSC-derived cells in vitro (e.g. V2a interneuron, V0 interneuron, and chemosensing interneuron), is meant to include substantially mature interneurons as well as partially differentiated cells committed to each specific interneuron cell fate. The expression level of a gene on average across a population of cells may be measured by, e.g., measuring RNA transcript level in a sample containing nucleic acid isolated from the population of cells using, e.g., real time quantitative polymerase chain reaction (RT-qPCR). The expression level of a gene at single cell resolution may be measured by, e.g., measuring the level of the protein encoded by the gene in individual cells, such as by contacting a detectable antibody specific to the protein encoded by the gene (e.g., a primary antibody that is specific to the protein encoded by the gene and that is detectable when bound by a detectably labeled secondary antibody specific to the primary antibody) with permeabilized cells from a population of cells, followed by flow cytometry. Alternatively, the expression level of a gene at single cell resolution in cells of a tissue slice or on a slide may be measured by immunohistochemistry.

"V2a interneurons" refer to a subtype of glutamatergic (i.e., excitatory) interneurons that are found in the spinal cord and hindbrain. V2a interneurons may be distinguished from other interneurons and motoneurons in the spinal cord (and share the same progenitor cells) based on higher expression of V2a-specific markers, such as CHX10 or SOX14, relative to these other neurons. Thus, a V2a interneuron generated by methods of the present disclosure may be identified by an elevated protein or gene expression level of CHX10 in a cell (i.e., a CHX10+ cell) differentiated from an hPSC. V2a interneurons may also have higher expression of other markers, such as FOXN4 and LHX3, that are also highly expressed in one or more neuronal subtypes that share the same progenitors. In some embodiments, gene expression in the population of hindbrain cells including the heterogeneous population of interneurons is increased, compared to the population of hPSCs, for V2a interneurons and for one or more genes selected from: CHX10, SOX14, and IRX3.

CHX10 (also known as VSX2; Gene ID: 338917) can be used as a marker for cells committed to the V2a interneuron cell fate. Thus, in some embodiments, V2a interneurons generated from hPSCs according to methods of the present disclosure express CHX10 at a level higher than the level of expression of CHX10 in undifferentiated hPSCs from which the V2a interneurons were derived, or compared to non-V2a interneuron cells (e.g., motoneurons or other interneurons) that can be derived from the same progenitor cells as the V2a interneurons. Individual V2a interneuron generated from hPSCs may be identified, e.g., using flow cytometry, based on elevated CHX10 expression among the population of cells cultured according to methods of the present disclosure, and may be referred to as a "CHX10+ cell". In some embodiments, the population of cells that include V2a interneurons generated from culturing hPSCs according to methods of the present disclosure may have an at least 10 fold higher, e.g., at least 50 fold higher, at least 100 fold higher, at least 500 fold higher, including at least 1,000 fold higher measured level of CHX10 expression compared to the undifferentiated hPSCs from which the V2a interneurons were derived, or compared to non-V2a interneuron cells (e.g., motoneurons or other interneurons) that can be derived from the same progenitor cells as the V2a interneurons.

SOX14 (Gene ID: 8403) may be a marker for cells committed to the V2a interneuron cell fate. Thus, in some embodiments, V2a interneurons generated from hPSCs according to methods of the present disclosure express SOX14 at a level higher than the level of expression of SOX14 in undifferentiated hPSCs from which the V2a interneurons were derived, or compared to non-V2a interneuron cells (e.g., motoneurons or other interneurons) that can be derived from the same progenitor cells as the V2a interneurons. Individual V2a interneuron generated from hPSCs may be identified, e.g., using flow cytometry, based on elevated SOX14 expression among the population of cells cultured according to methods of the present disclosure, and may be referred to as a "SOX14+ cell". In some embodiments, the population of cells that include V2a interneurons generated from culturing hPSCs according to methods of the present disclosure may have an at least 5 fold higher, e.g., at least 10 fold higher, at least 50 fold higher, at least 100 fold higher, including at least 1,000 fold higher measured level of expression of SOX14 protein or RNA transcript compared to a population of undifferentiated hPSCs from which the V2a interneurons were derived, or compared to a population of non-V2a interneuron cells (e.g., motoneurons or other interneurons) that can be derived from the same progenitor cells as the V2a interneurons.

FOXN4 (Gene ID: 121643) may be a marker for spinal progenitor cells that can give rise to cells committed to the V2a interneuron cell fate. Thus, in some embodiments, V2a interneurons generated from hPSCs according to methods of the present disclosure express FOXN4 at a level higher than the level of expression of FOXN4 in undifferentiated hPSCs from which the V2a interneurons were derived, or compared to cells that do not share the same spinal progenitor cells. Individual V2a interneuron generated from hPSCs may be identified, e.g., using flow cytometry, based on elevated FOXN4 expression among the population of cells cultured according to methods of the present disclosure, and may be referred to as a "FOXN4+ cell". In some embodiments, the population of cells that include V2a interneurons generated from hPSCs according to methods of the present disclosure may have an at least 5 fold higher, e.g., at least 10 fold higher, at least 50 fold higher, including at least 100 fold higher measured level of FOXN4 expression compared to the undifferentiated hPSCs from which the V2a interneurons were derived.

LHX3 (Gene ID: 8022) can be used as a marker for spinal progenitor cells that can give rise to cells committed to the V2a interneuron cell fate. Thus, in some embodiments, V2a interneurons generated from hPSCs according to methods of the present disclosure express LHX3 at a level higher than the level of expression of LHX3 in undifferentiated hPSCs from which the V2a interneurons were derived, or compared to non-V2a interneuron cells (e.g., motoneurons or other interneurons) that can be derived from the same progenitor cells as the V2a interneurons. Individual V2a interneuron generated from hPSCs may be identified, e.g., using flow cytometry, based on elevated LHX3 expression among the population of cells cultured according to methods of the present disclosure, and may be referred to as a "LHX3+ cell". In some embodiments, the population of cells that include V2a interneurons generated from hPSCs, according to methods of the present disclosure, may have at least 5 fold higher, e.g., at least 10 fold higher, at least 50 fold higher, including at least 100 fold higher measured level of expression of LHX3 protein or RNA transcript compared to the undifferentiated hPSCs from which the V2a interneurons were derived.

GATA3 (Gene ID: 2625) can be used as a marker for cells differentiated from spinal progenitor cells of V2a interneurons, but that are committed to a non-V2a interneuron cell fate, e.g., committed to a V2b interneuron cell fate. In some cases, the population of cells that include V2a interneurons generated from hPSCs, according to methods of the present disclosure, may have 10 fold or less, e.g., 5 fold or less, 4 fold or less, 3 fold or less, including 2 fold or less increase in the measured level of expression of GATA3 protein or RNA transcript compared to the undifferentiated hPSCs from which the V2a interneurons were derived.

HB9 (also known as MNX1; Gene ID: 3110) may be a marker for cells committed to a non-V2a interneuron cell fate, e.g., committed to a spinal cord motoneuron cell fate. In some cases, the population of cells that include V2a interneurons generated from hPSCs according to methods of the present disclosure may have 10 fold or less, e.g., 5 fold or less, 4 fold or less, 3 fold or less, including 2 fold or less increase in the measured level of expression of HB9 protein or RNA transcript compared to the undifferentiated hPSCs from which the V2a interneurons were derived.

"V0 interneurons" refer to a subtype of commissural interneurons that are found in the spinal cord and hindbrain. V0 interneurons may be distinguished from other interneurons and motoneurons in the spinal cord (and share the same progenitor cells) based on higher expression of V0-specific markers, such as LHX5 or PAX2, relative to these other neurons. Thus, a V0 interneuron generated by methods of the present disclosure may be identified by an elevated protein or gene expression level of LHX5 in a cell (i.e., a LHX5+ cell) differentiated from an hPSC. V0 interneurons may also have higher expression of other markers, such as EVX1 and EVX2, that are also highly expressed in one or more neuronal subtypes that share the same progenitors. In some embodiments, gene expression in the population of hindbrain cells including the heterogeneous population of interneurons is increased, compared to the population of hPSCs, for V0 interneurons and for one or more genes selected from: LHX5, PAX2, MAB21L2, EVX1, and EVX2.

LHX5 (Gene ID: 64211) can be used as a marker for cells committed to the V0 interneuron cell fate. Thus, in some embodiments, V0 interneurons generated from hPSCs according to methods of the present disclosure express LHX5 at a level higher than the level of expression of LHX5 in undifferentiated hPSCs from which the V0 interneurons were derived, or compared to non-V0 interneuron cells (e.g., motoneurons or other interneurons) that can be derived from the same progenitor cells as the V0 interneurons. Individual V0 interneurons generated from hPSCs may be identified, e.g., using flow cytometry, based on elevated LHX5 expression among the population of cells cultured according to methods of the present disclosure, and may be referred to as a "LHX5+ cell". In some embodiments, the population of cells that include V0 interneurons generated from culturing hPSCs according to methods of the present disclosure may have an at least 5 fold higher, e.g., at least 10 fold higher, at least 50 fold higher, at least 100 fold higher, including at least 1,000 fold higher measured level of expression of LHX5 protein or RNA transcript compared to a population of undifferentiated hPSCs from which the V0 interneurons were derived, or compared to a population of non-V0 interneuron cells (e.g., motoneurons or other interneurons) that can be derived from the same progenitor cells as the V0 interneurons.

"Chemosensing interneurons" refer to a subtype of interneurons that are found in the hindbrain. Chemosensing interneurons may be distinguished from other interneurons and motoneurons in the spinal cord (and share the same progenitor cells) based on higher expression of chemosensing-specific markers, such as PHOX2A or PHOX2B, relative to these other neurons. Thus, a chemosensing interneuron generated by methods of the present disclosure may be identified by an elevated protein or gene expression level of PHOX2A/B in a cell (i.e., a PHOX2A/B+ cell) differentiated from an hPSC. Chemosensing interneurons may also have higher expression of other markers, such as ADCYAP1, that is also highly expressed in one or more neuronal subtypes that share the same progenitors. In some embodiments, gene expression in the population of hindbrain cells including the heterogeneous population of interneurons is increased, compared to the population of hPSCs, for chemosensing interneurons and for one or more genes selected from: PHOX2A, PHOX2B, and ADCYAP1.

PHOX2A (Gene ID: 401) can be used as a marker for cells committed to the chemosensing interneuron cell fate. Thus, in some embodiments, chemosensing interneurons generated from hPSCs according to methods of the present disclosure express PHOX2A at a level higher than the level of expression of PHOX2A in undifferentiated hPSCs from which the chemosensing interneurons were derived, or compared to non-chemosensing interneuron cells (e.g., motoneurons or other interneurons) that can be derived from the same progenitor cells as the chemosensing interneurons. Individual chemosensing interneurons generated from hPSCs may be identified, e.g., using flow cytometry, based on elevated PHOX2A expression among the population of cells cultured according to methods of the present disclosure, and may be referred to as a "PHOX2A+ cell". In some embodiments, the population of cells that include chemosensing interneurons generated from culturing hPSCs according to methods of the present disclosure may have an at least 5 fold higher, e.g., at least 10 fold higher, at least 50 fold higher, at least 100 fold higher, including at least 1,000 fold higher measured level of expression of PHOX2A protein or RNA transcript compared to a population of undifferentiated hPSCs from which the chemosensing interneurons were derived, or compared to a population of non-chemosensing interneuron cells (e.g., motoneurons or other interneurons) that can be derived from the same progenitor cells as the chemosensing interneurons.

PHOX2B (Gene ID: 8929) can be used as a marker for cells committed to the chemosensing interneuron cell fate. Thus, in some embodiments, chemosensing interneurons generated from hPSCs according to methods of the present PHOX2B express PHOX2B at a level higher than the level of expression of PHOX2A in undifferentiated hPSCs from which the chemosensing interneurons were derived, or compared to non-chemosensing interneuron cells (e.g., motoneurons or other interneurons) that can be derived from the same progenitor cells as the chemosensing interneurons. Individual chemosensing interneurons generated from hPSCs may be identified, e.g., using flow cytometry, based on elevated PHOX2B expression among the population of cells cultured according to methods of the present disclosure, and may be referred to as a "PHOX2B+ cell". In some embodiments, the population of cells that include chemosensing interneurons generated from culturing hPSCs according to methods of the present disclosure may have an at least 5 fold higher, e.g., at least 10 fold higher, at least 50 fold higher, at least 100 fold higher, including at least 1,000 fold higher measured level of expression of PHOX2B protein or RNA transcript compared to a population of undifferentiated hPSCs from which the chemosensing interneurons were derived, or compared to a population of non-chemosensing interneuron cells (e.g., motoneurons or other interneurons) that can be derived from the same progenitor cells as the chemosensing interneurons.

In some cases, the increase in the measured level of expression of V2a interneurons, V0 interneurons, and chemosensing interneurons, or a combination thereof, markers in a population of cells including V2a interneurons, V0 interneurons, and chemosensing interneurons, or a combination thereof, generated according to methods of the present disclosure, when compared to the undifferentiated hPSCs from which the V2a interneurons, V0 interneurons, and chemosensing interneurons, or a combination thereof, are derived, is at least 5 fold higher, e.g., at least 10 fold higher, at least 20 fold higher, at least 50 fold higher, at least 100 fold higher, at least 500 fold higher, including at least 1,000 fold higher than the increase in the measured level of expression of markers that are not specific to V2a interneurons (e.g., makers for spinal progenitor cells of the V2a interneurons, or for non-V2a descendants of the spinal progenitor cells), V0 interneurons, and chemosensing interneurons, or a combination thereof.

V2a interneuron-specific markers of interest include, e.g., CHX10 and SOX14. Non-V2a interneuron-specific markers of interest include GATA3, HB9 and PAX6 (Gene ID: 5080). V0 interneuron-specific markers of interest include, e.g., LHX5, PAX2, EVX1 and EVX2. Chemosensing interneuron-specific markers of interest include, e.g., PHOX2A and PHOX2B.

In some cases, the increase in level of expression of neuronal markers in a population of cells that include V2a interneurons, V0 interneurons, and chemosensing interneurons, or a combination thereof, generated according to methods of the present disclosure, when compared to the undifferentiated hPSCs from which the V2a interneurons, V0 interneurons, and chemosensing interneurons, or a combination thereof, are derived, is at least 5 fold higher, e.g., at least 10 fold higher, at least 20 fold higher, including at least 50 fold higher, than the increase in expression of non-neuronal markers (e.g., markers for glial or retinal cell types).

Neuronal markers of interest include NF and βIII tubulin. Glial markers of interest include PDFGRA (Gene ID: 5156), CSPG4 (Gene ID: 1464), SOX10 (Gene ID: 6663) and GFAP (Gene ID: 2670). Retinal markers of interest include THY1 (Gene ID: 7070), IRBP (also known as RBP3; Gene ID: 5949) and CRX (Gene ID: 1406).

The present disclosure provides efficient methods of generating V2a interneurons, V0 interneurons, and chemosensing interneurons, or a combination thereof, from hPSCs. Thus, in some embodiments, about 10% or more, e.g., about 20% or more, about 30% or more, about 40% or more, including about 50% or more of the cells after culturing in the neural induction medium (e.g., after culturing in the last of multiple neural induction media, as described further below), according to methods of the present disclosure are CHX10+ cells, LHX5+ cells, PHOX2A+ cells and/or PHOX2B+ cells. In some embodiments, the percentage of CHX10+ cells, LHX5+ cells, PHOX2A+ cells and/or PHOX2B+ cells among the cells after culturing in the neural induction medium (e.g., after culturing in the last of multiple neural induction media, as described further below), according to methods of the present disclosure is from about 10% to about 60%, e.g., from about 20% to about 55%, including from about 25 to about 50%. In some cases, the average number of CHX10+ cells, LHX5+ cells, PHOX2A+ cells and/or PHOX2B+ cells generated per input hPSC cell is about 5 or more, e.g., about 7 or more, about 10 or more, about 12 or more, including about 15 or more. In some embodiments, the average number of CHX10+ cells, LHX5+ cells, PHOX2A+ cells and/or PHOX2B+ cells generated per input hPSC cell is from about 5 to about 25, e.g., from about 7 to about 20, including from about 10 to about 15.

In some embodiments, at least 10%, e.g., at least 20%, at least 30%, at least 40%, including at least 50%, of the population of hindbrain cells including the heterogeneous population of interneurons are CHX10+ V2a interneurons. In exemplary embodiments, 20% to 40% of the population of hindbrain cells including the heterogeneous population of interneurons are CHX10+ V2a interneurons. In some embodiments, at least 10%, e.g., at least 20%, at least 30%, at least 40%, including at least 50%, of the population of hindbrain cells including the heterogeneous population of interneurons are LHX5+ V0 interneurons. In exemplary embodiments, 10% to 60% of the population of hindbrain cells including the heterogeneous population of interneurons are LHX5+ V0 interneurons. In other embodiments, 20% to 40% of the population of hindbrain cells including the heterogeneous population of interneurons are LHX5+ V0 interneurons. In some embodiments, at least 10%, e.g., at least 20%, at least 30%, at least 40%, including at least 50%, of the population of hindbrain cells including the heterogeneous population of interneurons are PHOX2A+ chemosensing interneurons and/or PHOX2B+ chemosensing interneurons. In exemplary embodiments, 10% to 60% of the population of hindbrain cells including the heterogeneous population of interneurons are PHOX2A+ chemosensing interneurons and/or PHOX2B+ chemosensing interneurons.

In some embodiments, about 30% or more, e.g., about 35% or more, about 40% or more, including about 45% or more of the cells after culturing in the neural induction medium (e.g., after culturing in the last of multiple neural induction media, as described further below), according to methods of the present disclosure are LHX3+ cells. In some embodiments, the percentage of LHX3+ cells among the cells after culturing in the neural induction medium (e.g., after culturing in the last of multiple neural induction media, as described further below), according to methods of the present disclosure is from about 30% to about 60%, e.g., from about 40% to about 55%, including from about 45 to about 55%.

Also provided herein are V2a interneurons that are CHX10+ cells, e.g., cells committed to the V2a interneuron cell fate, V0 interneurons that are LHX5+ cells, e.g., cells committed to the V0 interneuron cell fate, or chemosensing interneurons that are PHOX2A/B+ cells, e.g., cells committed to the chemosensing interneuron cell fate, all derived from the hPSCs in vitro, and further cultured under suitable conditions, as described below, to exhibit functional properties of mature neurons. The mature V2a interneurons, V0 interneurons, chemosensing interneurons, or a combination thereof, may exhibit any number of properties that are indicative of neurons. The neuronal properties include, e.g., electrophysiological activity, expression of neuron-related genes, extension of neurites, and localization of synaptic markers to neurites. Electrophysiologically active cells may be electrically excitable, and may include spontaneous electrophysiological activity, e.g., as measured by calcium imaging using a calcium indicator, or induced electrophysiological activity, e.g., as measured by action potential firing induced by injection of current through the cell using an electrode.

V2a interneurons, V0 interneurons, and chemosensing interneurons, or a combination thereof, may further reduce expression of CHX10, LHX5, and/or PHOX2A/B over time while being cultured in a neural maturation medium. Thus, in some embodiments, a population of cells containing mature V2a interneurons, V0 interneurons, and chemosensing interneurons, or a combination thereof, has lower expression of CHX10, LHX5, and/or PHOX2A/B (e.g., lower percentage of CHX10+ cells, LHX5+ cells, and/or PHOX2A/B+ cells) than a population of cells containing V2a interneurons, V0 interneurons, and chemosensing interneurons, or a combination thereof, derived from hPSCs at the end of culturing in a neural induction medium.

In some cases, mature V2a interneurons, V0 interneurons, or chemosensing interneurons, fire action potentials in response to a current injection (e.g., a current injection of 20 pA) at a maximum rate of about 1.0/second(s) or more, e.g., about 2.0/s or more, 3.0/s or more, 5.0/s or more, 10/s or more, including 15/s or more.

In some cases, both a specific marker (e.g. CHX10, LHX5, and PHOX2A/B) and a gene related to neurons may be expressed by V2a interneurons, V0 interneurons, and chemosensing interneurons, or a combination thereof, as they mature. Suitable neuron-related genes may include, e.g., the vesicular glutamate transporter (e.g., VGlut1) and NeuN (also known as Rbfox3). Mature V2a interneurons expressing CHX10 may not express genes related to GABA release.

Synaptic markers of interest may include, e.g., a postsynaptic marker, such as GRIP1, or a presynaptic marker, such as synaptophysin.

Methods of Generating a Three-Dimensional Organoid

Hindbrain-like organoids can be produced by culturing PSCs in a neural induction medium in a three-dimensional (3D) culture system. In some embodiments, a population of PSCs is treated in vitro with a WNT signaling pathway activator and cultured in a neural induction medium comprising a RA signaling pathway activator, a Shh signaling pathway activator, and a Notch signaling pathway inhibitor (e.g., DAPT) in a 3D culture system as described herein, wherein a three-dimensional organoid is generated comprising a heterogeneous population of interneurons comprising V2a interneurons, V0 interneurons, and chemosensing interneurons.

In some embodiments, the PSCs are first treated with a WNT signaling pathway activator and initially cultured in a monolayer prior to transfer to the 3D culture system for differentiation and aggregation into an organoid. For example, the PSCs may be cultured with the WNT signaling pathway activator (e.g., CHIR99021) for any suitable length of time, and in some cases may be cultured in a monolayer culture for about 1 to 7 days, such as about 1, about 2, about 3, about 4, about 5, about 6, or about 7 days prior to transfer to the 3D culture system for differentiation in a neural induction medium.

In some embodiments, prior to differentiation in the neural induction medium, the PSCs are partially differentiated into hindbrain progenitor cells, e.g., by culturing the population of PSCs in an early differentiation medium that includes a ROCK inhibitor, but does not include the RA signaling pathway activator, Shh signaling pathway activator, or Notch signaling pathway inhibitor. The PSCs may be further differentiated in an early differentiation medium that also includes one or more SMAD signaling pathway inhibitors (e.g., LDN193189 and SB431542) in addition to the ROCK inhibitor. For example, the PSCs may be cultured with a WNT signaling pathway activator (e.g., CHIR99021), a ROCK inhibitor, and SMAD signaling pathway inhibitors (e.g., LDN193189 and SB431542) in a 3D culture system for any suitable length of time to allow partial differentiation and aggregation into organoids, and in some cases may be cultured for about 5 to about 9 days, such as about 5, about 6, about 7, about 8, or about 9 days prior to differentiation in a neural induction medium.

In some embodiments, the PSCs are subsequently cultured in a neural induction medium comprising a RA signaling pathway activator, Shh signaling pathway activator, and Notch signaling pathway inhibitor. For example, the PSCs may be cultured in one or more neural induction media, as described herein, for any suitable length of time sufficient to allow differentiation into hindbrain-like cells, including CHX10+ cells (e.g., CHX10+ V2a interneurons), SOX14+ cells (e.g., SOX14+ V2a interneurons), IRX3+ cells (e.g., IRX3+ V2a interneurons), LHX5+ cells (e.g., LHX5+ V0 interneurons), PAX2+ cells (e.g., PAX2+ V0 interneurons), MAB21L2+ cells (e.g., MAB21L2+ V0 interneurons), PHOX2A+ cells (e.g., PHOX2A+ chemosensing interneurons), PHOX2B+ cells (e.g., PHOX2B+ chemosensing interneurons), ADCYAP1+ cells (e.g., ADCYAP1+ chemosensing interneurons), or a combination thereof, and in some cases may be cultured for about 15 to about 20 days, such as about 15, about 16, about 17, about 18, about 19, or about 20 days in the neural induction media.

The size of the organoids and the relative proportions of the V2a and V0 interneurons produced can be controlled by varying the concentration of the Shh signaling pathway activator in the neural induction media. For example, organoids produced by differentiation in a neural induction medium having the Shh signaling pathway activator, purmorphamine (pur), at a concentration ranging from about 10 nm to about 100 nm are smaller in size than organoids produced by differentiation in a neural induction medium having higher concentrations of pur, such as 1 μM pur. At 1 μM pur, lower percentages of LHX5 (3.1%) and higher percentages of CHX10 (23.3%, V0$^{low}$V2a$^{high}$) positive cells are produced, whereas at 100 nM pur, higher percentages of LHX5 (36.5%) and lower percentages of CHX10 (3.5%, V0$^{high}$V2a$^{low}$) positive cells are produced.

After differentiation in the neural induction media, the organoids may be subsequently transferred to a neural maturation medium supplemented with growth factors. The neural maturation medium may be any suitable medium for promoting maturation of the V2a interneurons, V0 interneurons, and chemosensing interneurons, or a combination thereof. Suitable media include, without limitation, NEUROBASAL™ medium (neural cell culture medium) and NSC™ (Neural Stem Cell culture media) from Life Technologies, PNGM™ (Primary Neuron Growth Medium) from Lonza, Neural Stem Cell basal medium from Millipore and STEMDIFF™ (pluripotent stem cell differentiation media) from StemCell Technologies. The neural maturation medium may be supplemented with any suitable supplements, such as, without limitation, B27 supplement, and neuronal growth factors. Suitable growth factors include, without limitation, BDNF, glial cell line-derived neurotrophic factor (GDNF), ciliary neurotrophic factor (CNTF), and insulin-like growth factor (IGF).

The organoids may be cultured in the neural maturation medium for any suitable length of time to induce maturation of the V2a interneurons, V0 interneurons, chemosensing interneurons, or a combination thereof, and in some cases may be in the neural induction medium for about 20 days or more, e.g., about 25 days or more, about 30 days or more, about 40 days or more, about 50 days or more, about 60 days or more, including about 100 days or more.

The PSCs may be cultured using any suitable three-dimensional substrate that promotes aggregation of the cells into organoids, such as a hydrogel, porous scaffold, etc. (see, e.g., Example 2 describing the production of organoids using pyramidal inserts). In some embodiments, the substrate is coated with a suitable coating material for promoting PSC differentiation into V2a interneurons, V0 interneurons, chemosensing interneurons, or a combination thereof. In some cases, the substrate is coated with extracellular matrix components, such as, but not limited to, Matrigel®, fibronectin, laminin. In some cases, the substrate may include a coating of, without limitation, polyornithine, poly-lysine, purified collagen, gelatin, fibronectin, tenascin, vitronectin, entactin, heparin sulfate proteoglycans, poly glycolytic acid (PGA), poly lactic acid (PLA), and poly lactic-glycolic acid (PLGA). The PSCs may also be cultured as 3-D cell aggregates in a suitable cell culture suspension, e.g., in the absence of a scaffold material. In some embodiments the PSCs are first cultured as an adherent monolayer in the presence of a WNT signaling pathway activator prior to culturing in a 3D culture system (i.e., pretreated with a WNT signaling pathway activator before aggregating cells into an organoid and treatment with neural induction media).

In some embodiments, an isolated three-dimensional organoid, generated according to the methods described herein, is provided. The three-dimensional organoid may have a diameter from about 100 μm to about 2000 μm, e.g., from about 200 μm to about 1000 μm, from about 300 μm to about 1500 μm, or from about 400 to about 2000 μm. In some embodiments, the three-dimensional organoid ranges from about 500 μm to about 700 μm in diameter. The three-dimensional organoid may have a size of about 100 μm to 10 mm in its longest dimension, or any size, shape or volume. The three-dimensional organoid may be provided in the form of a globular body, e.g. as an aggregate of cells as described above, which may be approximately spherical or any given shape depending on the characteristics of the 3D culture system. As differentiation progresses, the organoids may become less spherical, which may reflect morphogenic changes associated with differentiation. The three-dimensional organoid may also be provided as a tissue slice.

The organoids produced by the methods described herein have at least some features of the hindbrain, including neuronal cell populations important for controlling respiration such as V2a interneurons, V0 interneurons, and chemosensing interneurons. In addition, the mature organoids may comprise cells expressing one or more mature neuronal markers such as, but not limited to, NeuN (a marker of mature neurons), glial fibrillary acidic protein (GFAP, a marker of astrocytes), Tau (a marker of mature filaments), vesicular glutamate transporter 2 (VGlut2, a marker of glutamatergic neurons), synaptophysin (a pre-synaptic marker), and OLIG2 (a marker of oligodendrocytes). The organoids may also display synchronous, periodic Ca$^{2+}$ transients as they mature consistent with the normal role of the hindbrain interneurons in respiratory rhythm generation. In addition, the organoids described herein may form neural rosettes that resemble the neural tube that normally forms during neural development (see Example 2). Such hindbrain-like organoids can be used, for example, to model the neural circuits that control respiratory rhythm generation and are useful for screening therapeutics that affect hindbrain function.

Methods of Generating a Heterogeneous Population of Interneurons from hPSC Cells Also provided herein is a method of producing a non-human animal model of a population of hindbrain cells including a heterogeneous population of interneurons such as human V2a interneurons, V0 interneurons, and chemosensing interneurons, or a combination thereof, e.g., an in vivo model for human interneuron growth and development. The method may include transplanting a population of cells that includes, for example, V2a, V0, and/or chemosensing interneurons (i.e., CHX10+SOX14+IRX3+ (V2a), LHX5+PAX2+MAB21L2+ (V0), and/or PHOX2A+PHOX2B+ADCYAP1+ (chemosensing) cells that were cultured in the neural induction medium, but not reseeded and cultured in the neural maturation medium) into a non-human animal. The population of cells may be transplanted into any suitable location within the host animal, and in some cases, may be transplanted into one or more spinal segments of the spinal cord. In each spinal segment, the population of cells may be transplanted at one or more different sites. In some cases, the population of cells is transplanted into the ventral horn of the spinal cord, where V2a interneurons, V0 interneurons, and chemosensing interneurons from the host animal are normally found. The transplanted cells may develop in the host environment to acquire one or more properties of mature V2a interneurons, V0 interneurons, and chemosensing interneurons, or a combination thereof.

The number of cells transplanted into the spinal cord may be any suitable number, and may be, e.g., 10$^2$ cells/transplantation site to 10$^6$ cells/transplantation site, such as 5.0× 10$^2$ cells/transplantation site to 5.0×10$^5$ cells/transplantation site, $5.0 \times 10^3$ cells/transplantation site to $5.0 \times 10^5$ cells/transplantation site, or $5.0 \times 10^4$ cells/transplantation site to $5.0 \times 10^5$ cells/transplantation site, including about $1.25 \times 10^5$ cells/transplantation site.

The non-human animal may be any suitable animal, and may be a mammal. The mammal may be any suitable mammal, and may be, but is not limited to, a rodent (e.g., mouse, rat, etc.) a lagomorph (e.g., a rabbit, etc.), a feline (e.g., cat, etc.), a canine (e.g., dog, etc.), an ungulate (e.g., a pig, a cow, a horse, etc.), monkey, or a non-human primate, etc.

Also provided herein are non-human animal models that include the V2a interneurons, V0 interneurons, and chemosensing interneurons, or a mature form thereof, derived from hPSCs according to methods of the present disclosure. The non-human animal model may be a host animal chosen from any suitable non-human animal, as described above. In some embodiments, the V2a interneurons, V0 interneurons, and chemosensing interneurons, or the mature form thereof, are in the spinal cord, e.g., the ventral horn of the spinal cord, of the host animal.

The mature form of the V2a interneuron, V0 interneuron, and/or chemosensing interneuron in the host animal may exhibit one or more properties associated with a mature V2a interneuron. In some cases, the mature V2a interneuron, V0 interneuron, and/or chemosensing interneuron, expresses NeuN and/or VGlut2 at a higher level than a background level of expression, e.g., as assessed by immunohistochemistry. In some embodiments, the mature form the V2a interneuron, V0 interneuron, and/or chemosensing interneuron in the host has neurites (e.g., axons and/or dendrites) that extend along the rostral-caudal axis of the spinal cord. The length of the neurite along the rostral-caudal axis of the spinal cord may vary depending on, e.g., the extent of maturation of the V2a interneuron, V0 interneuron, and/or chemosensing interneuron, the site of transplantation of the V2a interneuron, V0 interneuron, and/or chemosensing interneuron, the time elapsed after transplantation, etc. In some cases, the neurite extends for 3 mm or more, e.g., 4 mm or more, including 5 mm or more, along the rostral-caudal axis of the spinal cord. The neurite may contain one or more functional synapses along its length. In some cases, the neurite includes one or more pre- and/or postsynaptic structures. In some cases, the presynaptic structure is associated with (e.g., juxtaposed with) a host neuron.

Utility

The present methods and PSC-derived interneurons, organoids, and animal models find use in many applications where it is desirable to understand aspects of the development and function of human V2a interneurons, V0 interneurons, and/or chemosensing interneurons, and to use human V2a interneurons, V0 interneurons, and/or chemosensing interneurons for regenerative cell therapies to treat central nervous system (CNS) diseases or injuries.

In some cases, non-human animal models may be used to study how to transplant human V2a interneurons, V0 interneurons, and/or chemosensing interneurons into the central nervous system in order to provide mature V2a interneurons, V0 interneurons, and/or chemosensing interneurons that synapse onto postsynaptic host targets and receive synaptic input from presynaptic host neurons, and thereby establish a functional relay between the presynaptic host neuron and the postsynaptic host neuron.

In some cases, human V2a interneurons, V0 interneurons, and/or chemosensing interneurons derived from hPSCs (e.g., hESCs or iPSCs) according to the present disclosure, may be transplanted into a damaged central nervous system of a patient, where maturation of the V2a interneurons, V0 interneurons, and/or chemosensing interneurons in the patient central nervous system may repair nerve damage and may restore at least some of the neurological defects associated with the damaged central nervous system.

In some cases, an isolated three-dimensional organoid may be used as a disease model for research and development. For example, an organoid may be used in screening therapeutics for treating a central nervous system disease or respiratory disease. In some embodiments, the organoid genome comprises a mutation associated with a central nervous system disease or respiratory disease. The organoid genome may be heterozygous or homozygous for the mutation. In one embodiment, an isolated three-dimensional organoid comprises a mutation associated with congenital central hypoventilation syndrome (CCHS). The organoid genome may comprise, for example, a PHOX2B mutation including without limitation, a polyalanine expansion or Y14X mutation. Such organoid disease models can be used to assess how disease phenotypes affect respiratory output and to test new drug therapies for treating respiratory distress.

In some cases, an isolated three-dimensional organoid may be used in research to achieve a better understanding of the interactions and functions of hindbrain cells. For example, an organoid may be used to track neural connectivity, investigate the roles of V2a interneurons, V0 interneurons, and/or chemosensing interneurons, and/or other hindbrain cells in controlling respiration, particularly respiratory rhythm.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-78 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A method of generating a three-dimensional organoid comprising a population of hindbrain cells comprising a heterogeneous population of interneurons, the method comprising:
   treating a population of mammalian pluripotent stem cells (PSCs) in vitro with a Wingless-Int (WNT) signaling pathway activator; and
   culturing the population of PSCs in a neural induction medium comprising:
      a retinoic acid signaling pathway activator;
      a sonic hedgehog (Shh) signaling pathway activator; and
      a Notch signaling pathway inhibitor;
   wherein the culturing results in generation of the population of hindbrain cells comprising the heterogeneous population of interneurons, wherein the heterogeneous population of interneurons comprises V2a interneurons, V0 interneurons, chemosensing interneurons, or a combination thereof, and generation of the three-dimensional organoid.

2. The method of 1, wherein the retinoic acid signaling pathway activator comprises a retinoic acid receptor agonist.

3. The method of 2, wherein the retinoic acid receptor agonist comprises retinoic acid, or a derivative thereof.

4. The method of any one of 1 to 3, wherein the Shh signaling pathway activator comprises a Smoothened agonist.

5. The method of 4, wherein the Smoothened agonist is purmorphamine, or a derivative thereof.

6. The method of any one of 1 to 5, wherein the Notch signaling pathway inhibitor comprises an inhibitor of Notch receptor activation.

7. The method of 6, wherein the inhibitor of Notch receptor activation is a Notch receptor antagonist.

8. The method of 6, wherein the inhibitor of Notch receptor activation comprises a γ-secretase inhibitor.

9. The method of 8, wherein the γ-secretase inhibitor is N-[(3,5-difluorophenyl)acetyl]-L-alanyl-2-phenyl]glycine-1,1-dimethylethyl ester (DAPT).

10. The method of any one of 1 to 9, wherein the retinoic acid signaling pathway activator is present in the neural induction medium at a concentration of from about 1 nM to about 2 μM.

11. The method of 10, wherein the retinoic acid signaling pathway activator is present in the neural induction medium at a concentration of from about 10 nM to about 1 μM.

12. The method of 11, wherein the retinoic acid signaling pathway activator is present in the neural induction medium at a concentration of about 100 nM.

13. The method of any one of 1 to 12, wherein the Shh signaling pathway activator is present in the neural induction medium at a concentration in the range of about 1 nM to about 2 μM.

14. The method of 13, wherein the Shh signaling pathway activator is present in the neural induction medium at a concentration of from about 10 nM to about 30 nM.

15. The method of 13, wherein the Shh signaling pathway activator is present in the neural induction medium at a concentration of from about 30 nM to about 100 nM.

16. The method of 13, wherein the Shh signaling pathway activator is present in the neural induction medium at a concentration of about 100 nM.

17. The method of 16, wherein the heterogeneous population of interneurons is enriched for V0 interneurons.

18. The method of 16 or 17, wherein the heterogeneous population of interneurons is enriched for PHOX2A+ and PHOX2B+ chemosensing interneurons.

19. The method of 13, wherein the Shh signaling pathway activator is present in the neural induction medium at a concentration of about 1 μM.

20. The method of 19, wherein the heterogeneous population of interneurons is enriched for V2a interneurons.

21. The method of any one of 1 to 20, wherein the Notch signaling pathway inhibitor is present in the neural induction medium at a concentration of about 250 nM to about 10 μM.

22. The method of 21, wherein the Notch signaling pathway inhibitor is present in the neural induction medium at a concentration of about 500 nM to about 5 μM.

23. The method of 22, wherein the Notch signaling pathway inhibitor is present in the neural induction medium at a concentration of about 1 μM.

24. The method of any one of 1 to 23, wherein the neural induction medium comprises one or more SMAD signaling pathway inhibitors.

25. The method of 24, wherein the one or more SMAD signaling pathway inhibitors are selected from Noggin, dorsomorphin, LDN193189, SB431542, or a combination thereof.

26. The method of any one of 1 to 25 wherein the WNT signaling pathway activator is a GSK3 inhibitor.

27. The method of 26, wherein the GSK3 inhibitor is CHIR99021.

28. The method of any one of 1 to 27, wherein the WNT signaling pathway activator is selected from the group consisting of CHIR99021, WAY-316606, IQ1, QS11, SB-216763, BIO, and DCA.

29. The method of any one of 1 to 28, wherein said culturing the population of PSCs in the neural induction medium is performed on a three-dimensional substrate.

30. The method of any one of 1 to 29, wherein said culturing the population of PSCs in the neural induction medium is performed in a pyramidal mold.

31. The method of any one of 1 to 30, wherein the culturing comprises contacting the population of PSCs, in order, with:
a WNT signaling pathway activator;
a first neural induction medium comprising the retinoic acid signaling pathway activator; and
a second neural induction medium comprising the retinoic acid signaling pathway activator, the Shh signaling pathway activator, and the Notch signaling pathway inhibitor,
under conditions sufficient to generate the population of hindbrain cells comprising the heterogeneous population of interneurons, wherein the heterogeneous population of interneurons comprises V2a interneurons, V0 interneurons, chemosensing interneurons, or a combination thereof.

32. The method of 31, wherein the culturing further comprises contacting the population of PSCs with a third neural induction medium comprising the retinoic acid signaling pathway activator, the Shh signaling pathway activator, and the Notch signaling pathway inhibitor.

33. The method of 31 or 32, wherein the first neural induction medium further comprises the Notch signaling pathway inhibitor.

34. The method of any one of 31 to 33, wherein contacting the population of PSCs with the second neural induction medium is performed about two days after contacting with the first neural induction medium.

35. The method of any one of 31 to 34, wherein the population of PSCs is cultured for a period of 7 to 13 days after contacting with the first neural induction medium.

36. The method of any one of 31 to 35, wherein the first neural induction medium further comprises one or more SMAD signaling pathway inhibitors.

37. The method of any one of 31 to 36, wherein the second neural induction medium and the third neural induction medium do not comprise the one or more SMAD signaling pathway inhibitors.

38. The method of any one of 31 to 37, wherein the first neural induction medium further comprises one or more SMAD signaling pathway inhibitors.

39. The method of any one of 31 to 38, further comprising contacting the population of PSCs with a ROCK inhibitor and one or more SMAD signaling pathway inhibitors prior to the first neural induction medium.

40. The method of any one of 37 to 39, wherein the one or more SMAD signaling pathway inhibitors is selected from Noggin, dorsomorphin, LDN193189, SB431542, or a combination thereof.

41. The method of any one of 1 to 40, wherein the population of PSCs is cultured on a cell culture substrate comprising a coating of extracellular matrix components.

42. The method of 41, wherein the cell culture substrate comprises a coating of Matrigel.

43. The method of any one of 1 to 42, wherein the culturing comprises seeding the population of PSCs on a cell culture substrate at a density of about 100,000 cells/cm$^2$ to about 200,000 cells/cm$^2$.

44. The method of any one of 1 to 43, wherein the PSCs comprise embryonic stem cells (ESCs) or induced pluripotent stem cells (iPSCs).

45. The method of any one of 1 to 44, wherein the PSCs are human PSCs (hPSCs).

46. The method of 45, wherein the hPSCs are selected from the group consisting of H7 ESCs, H1 ESCs, WTC iPSCs, and WTB iPSCs.

47. The method of any one of 1 to 46, wherein at least 10%, at least 20%, at least 30%, at least 40%, or at least 50% of the population of hindbrain cells comprising the heterogeneous population of interneurons are CHX10+ V2a interneurons.

48. The method of any one of 1 to 47, wherein 20% to 40% of the population of hindbrain cells comprising the heterogeneous population of interneurons are CHX10+ V2a interneurons.

49. The method of any one of 1 to 48, wherein at least 10%, at least 20%, at least 30%, at least 40%, or at least 50% of the population of hindbrain cells comprising the heterogeneous population of interneurons are LHX5+ V0 interneurons.

50. The method of any one of 1 to 49, wherein 10% to 60% of the population of hindbrain cells comprising the heterogeneous population of interneurons are LHX5+ V0 interneurons.

51. The method of 50, wherein 20% to 40% of the population of hindbrain cells comprising the heterogeneous population of interneurons are LHX5+ V0 interneurons.

52. The method of any one of 1 to 51, wherein at least 10%, at least 20%, at least 30%, at least 40%, or at least 50% of the population of hindbrain cells comprising the heterogeneous population of interneurons are PHOX2A+ chemosensing interneurons or PHOX2B+ chemosensing interneurons.

53. The method of any one of 1 to 52, wherein 10% to 60% of the population of hindbrain cells comprising the heterogeneous population of interneurons are PHOX2A+ chemosensing interneurons or PHOX2B+ chemosensing interneurons.

54. The method of any one of 1 to 53, wherein gene expression in the population of hindbrain cells comprising the heterogeneous population of interneurons is increased, compared to the population of PSCs, for one or more genes selected from: PHOX2A, PHOX2B, ADCYAP1, CHX10, SOX14, IRX3, LHX5, PAX2, MAB21L2, SOX21, EVX1, and EVX2.

55. The method of 54, wherein gene expression in the chemosensing interneurons is increased compared to the population of PSCs for one or more genes selected from: PHOX2A, PHOX2B, and ADCYAP1.

56. The method of 54, wherein gene expression in the V2a interneurons is increased compared to the population of PSCs for one or more genes selected from: CHX10, SOX14, and IRX3.

57. The method of 54, wherein gene expression in the V0 interneurons is increased compared to the population of PSCs for one or more genes selected from: LHX5, PAX2, MAB21L2, EVX1, and EVX2.

58. The method of any one of 1 to 57, further comprising:
    reseeding at least some of the population of hindbrain cells comprising the heterogeneous population of interneurons onto a neural maturation substrate; and
    culturing the seeded population of hindbrain cells comprising the heterogeneous population of interneurons in a neural maturation medium, thereby generating a mature population of hindbrain cells comprising the heterogeneous population of interneurons.

59. The method of 58, wherein the heterogeneous population of interneurons of the mature population is electrically excitable.

60. The method of any one of 1 to 59, wherein the neural induction medium further comprises a ROCK inhibitor.

61. The method of any one of 1 to 60, wherein the population of hindbrain cells is a population of respiratory hindbrain cells.

62. The method of any one of 1 to 61, wherein the three-dimensional organoid comprises a diameter of about 100 μm to about 1000 μm.

63. The method of 62, wherein the three-dimensional organoid comprises a diameter of about 500 μm to about 700 μm.

64. A non-human animal model of hindbrain development, comprising a population of hindbrain cells comprising a heterogeneous population of interneurons produced according to the methods of any one of 1 to 63.

65. The non-human animal model of 64, wherein the animal model is a mammal.

66. The non-human animal model of 65, wherein the mammal is a rodent or primate.

67. An isolated three-dimensional organoid generated according to the methods of any one of 1 to 63.

68. The isolated three-dimensional organoid of 67, wherein the isolated three-dimensional organoid comprises a neural rosette.

69. The isolated three-dimensional organoid of 67 or 68, wherein the isolated three-dimensional organoid comprises V0 interneurons, V2a interneurons, and chemosensing neurons.

70. The isolated three-dimensional organoid of any one of 67 to 69, wherein the isolated three-dimensional organoid comprises more V0 interneurons than V2a interneurons.

71. The isolated three-dimensional organoid of any one of 67 to 69, wherein the isolated three-dimensional organoid comprises more V2a interneurons than V0 interneurons.

72. The isolated three-dimensional organoid of any one of 67 to 71, wherein the isolated three-dimensional organoid exhibits synchronous, periodic Ca$^{2+}$ transients.

73. The isolated three-dimensional organoid of any one of 67 to 72, wherein the isolated three-dimensional organoid genome comprises a mutation associated with congenital central hypoventilation syndrome (CCHS).

74. The isolated three-dimensional organoid of 73, wherein the mutation is in a PHOX2B gene.

75. The isolated three-dimensional organoid of 74, wherein the PHOX2B mutation is a polyalanine expansion.

76. The isolated three-dimensional organoid of 74, wherein the PHOX2B mutation is a Y14X mutation.

77. The isolated three-dimensional organoid of any one of 74 to 76, wherein the isolated three-dimensional organoid genome is heterozygous or homozygous for the mutation in the PHOX2B gene.

78. The isolated three-dimensional organoid of any one of 67 to 77, wherein the three-dimensional organoid comprises a diameter of about 100 μm to about 1000 μm.

79. The isolated three-dimensional organoid of 78, wherein the three-dimensional organoid comprises a diameter of about 500 μm to about 700 μm.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Co-Emergence of Respiratory Hindbrain Populations

Introduction

V2a interneurons can be induced from human pluripotent stem cells (Butts, McCreedy et al. 2017), however, the rostral-caudal identity and function of hPSC-derived V2a interneurons remains to be determined. Additionally, differentiation of V2a interneurons from hPSCs resulted in a heterogeneous population of cells including broad classes of committed neurons, neural progenitors, and glial populations. The specific neuronal cell types in the CHX10⁻ fraction of the cultures have not been identified. The following study demonstrates that hPSC-derived V2a interneurons have a phenotype similar to endogenous V2a interneurons present in the medial reticular formation (mRF) of the hindbrain, which are involved in respiratory control. Additionally, other hindbrain populations have been identified in the heterogeneous hPSC-derived culture including chemosensing neurons and V0 interneurons, which are also critical to the control of respiration. This study demonstrates how a combination of signals delivered in vitro can recapitulate developmental processes to specify a regional identity, in this case the hindbrain, and result in the co-emergence of multiple functionally related cell types.

The hindbrain, which is comprised of the medulla, pons, and cerebellum, is involved in coordination of many autonomic functions including respiration and heart rate. The neural tube gives rise to the hindbrain structures in response to sonic hedgehog (Shh), retinoic acid (RA), and WNT signaling (Ericson, Rashbass et al. 1997, Glover, Renaud et al. 2006, Elkouby and Frank 2010). Similar to the spinal cord, a ventrodorsal gradient of Shh patterns distinct progenitor domains of motor neuron and interneuron populations (Gray 2008). RA signaling and WNT activation specify the rostrocaudal identity of the hindbrain, marked by HOX 1-4 and rhombomere 3-7 expression (Gaunt, Krumlauf et al. 1989, Marshall, Nonchev et al. 1992, Krumlauf, Marshall et al. 1993, White, Nie et al. 2007). While these signaling events set up the transcription program to determine cell fate, the neural populations migrate and organize into clusters of neurons called nuclei that interact to perform a specific function including respiration in the medulla (Alheid, Gray et al. 2002).

Specific regions of the medulla have been identified to play a role in different phases of the respiration cycle. The Ventral Respiratory Column (VRC) is located in the ventrolateral medulla and contains important respiratory nuclei including the retrotrapezoid nucleus/prefacial respiratory group (RTN/pFRG) and preBötzinger complex (pre BötC) (Ezure, Manabe et al. 1988, Ellenberger and Feldman 1990). The neurons contained within these structures been classified by transcription factor expression during development and by neurotransmitter type as the neurons mature. The absence of these neurons through genetic manipulations demonstrates disruptions to and even absence of respiration. Here, the RTN/pFRG and pre BötC, the structures where the chemosensing and V0 interneurons reside, will be further described (Gray, Hayes et al. 2010).

The medial RTN/pFRG, located at the most rostral position of the VRC, is the connection between the environment and rate of respiration through chemosensing neurons (Mulkey, Stornetta et al. 2004, Stornetta, Moreira et al. 2006). This structure is composed primarily of cells that express the Phox2B transcription factor in the dorsal half of the neural tube and migrate to the ventral lateral medulla to the VRC (Sieber, Storm et al. 2007, Hernandez-Miranda and Birchmeier 2015). The Phox2B neurons mature into a glutamatergic phenotype that sense the partial pressure of $CO_2$ ($pCO_2$) in the blood stream through proton receptors (Wang, Shi et al. 2013). Phox2B$^{-/-}$ die in utero due to the absence of respiration while Phox2B$^{-/-}$ mice are born yet have early respiratory defects (Dauger, Pattyn et al. 2003). In addition, the RTN/pFRG, including the Phox2B$^{+}$ chemosensing population, transduce environmental information about $pCO_2$ to adjacent respiratory regions including the pre BötC (Bochorishvili, Stornetta et al. 2012).

The pre BötC, considered the main rhythm generator of respiration, is composed of cells that developmentally express the p0 transcription factor, Dbx1 (Smith, Ellenberger et al. 1991, Bouvier, Thoby-Brisson et al. 2010, Gray, Hayes et al. 2010). These cells then mature in to a variety of excitatory and inhibitory neurons including excitatory V0$_v$ interneurons (Gray 2008). The rhythm generating cells in the pre BötC have been identified to be glutamatergic, commissural, and express the neurokinin 1 receptor (NKIR) (Greer, Smith et al. 1991, Funk, Smith et al. 1993, Gray, Rekling et al. 1999, Wang, Stornetta et al. 2001). A recent single cell RNA sequencing analysis of Dbx1-expressing cells isolated from the pre BötC of P0 mice elucidated the transcriptional signature of V0$_v$ interneurons including expression of Lhx5, Pax2, and HoxA4 (Hayes, Kottick et al. 2017). Knockout of genes involved in the development of the pre BötC including Dbx1, Mafb, and Pbx3 results in severe respiratory deficits, reiterating its importance in control of respiration (Blanchi, Kelly et al. 2003, Rhee, Arata et al. 2004, Gray, Hayes et al. 2010). While the pre BötC receives input from the chemosensing neurons in the RTN/pFRG, it has also been demonstrated to receive input from medullary V2a interneurons (Crone, Viemari et al. 2012).

V2a interneurons do not reside in the VRC, however, they have been identified in the mRF of the medulla, adjacent to the pre BötC. Similar to the spinal cord, V2a interneurons in the mRF are glutamatergic and express CHX10. However, these medullary V2a interneurons have extensions to the pre BötC (Crone, Viemari et al. 2012). Complete ablation of medullary V2a interneurons results in embryonic death, and while partial ablation permits postnatal survival of mice, irregular breathing patterns in these newborn mice implicate the importance of this population in regulating respiration (Crone, Viemari et al. 2012).

While there are many cells involved in the control of respiration, V2a interneurons, V0 interneurons, and chemo-sensing neurons are important phenotypes in responding to environmental changes and generating the respiratory rhythm. These three cell types all arise from the developing neural tube in response to exposure to the same milieu of signaling molecules including Shh, RA, and WNT activation (Ericson, Rashbass et al. 1997, Glover, Renaud et al. 2006, Elkouby and Frank 2010). These cells migrate and mature into interconnected nuclei critical to respiratory control. In the following study, hPCS were exposed to a combination of morphogens similar to those present during development of these respiratory phenotypes, which has resulted in the co-emergence of V2a interneurons, V0 interneurons, and chemosensing neurons. When engineering a tissue composed of many cell types from hPSCs, the individual cell types are differentiated separately then merged together. This study takes a unique approach to co-emerge multiple neuronal populations from one set of signaling molecules in a way that is more similar to native development. To our knowledge, this is the first description of these respiratory populations from hPSCs and one of the few reports of co-emergent differentiation systems. The concept of co-emergence explored in this study can be applied to other directed differentiation systems for any lineage that developmentally results in multiple subtypes.

Materials and Methods

Human Pluripotent Stem Cell Culture hPSCs-WTC and WTB iPSCs (generously donated by Bruce Conklin)—were grown to 70% confluence and passaged using Accutase (Accutase, San Diego, CA) to dissociate to single cells (incubated at 37° C. for 5 minutes). Dissociated cells were replated on Matrigel-coated cultureware (hESC-qualified for ESCs and growth factor reduced for iPSCs) at a density of 10,000 cells per cm$^2$ with 10 μM ROCK inhibitor (Y-27632, Selleckchem, Houston, TX) in mTeSR (StemCell Technologies, Vancouver, Canada). All work with human ESC and iPSC lines have been approved by the University of California—San Francisco Human Gamete, Embryo and Stem Cell Research (GESCR) Committee.

V2a Interneuron Differentiation hPSCs were seeded in mTeSR supplemented with 10 μM ROCK inhibitor and dual SMAD inhibitors 0.2 μM LDN193189 and 10 μM SB431542 (StemGent, Cambridge, MA) at 5,000-100,000 cells/cm$^2$ onto 24-well plates coated with Matrigel. On day 3, medium was changed to m TeSR supplemented with dual SMAD inhibitors only. On day 5, the base medium was switched to neural induction medium (DMEM F: 12 (Corning, Corning, NY), N2 supplement (Life Technologies, Carlsbad, CA), L-Glutamine (VWR), 2 μg/ml heparin (Sigma Aldrich, St. Louis, MO), non-essential amino acids (Mediatech INC, Manassas, VA), penicillin-streptomycin (VWR) supplemented with fresh 0.4 ug/ml ascorbic acid (Sigma Aldrich) and 10 ng/ml brain derived neurotrophin factor (BDNF, R&D Systems, Minneapolis, MN)) supplemented with dual SMAD inhibitors and 10 nM-10 μM retinoic acid (Sigma Aldrich). On day 7, dual SMAD inhibition was ceased and 10 nM-10 μM retinoic acid, 10 nM-10 μM pur (EMD Millipore, Darmstast, Germany) and 1 μM N—[N-(3,5-difluorophenacetyl)-L-alanyl]-S-phenylglycine t-butyl ester (DAPT) were added to the neural induction medium. Medium was changed every 2-3 days throughout the differentiation, with fresh supplements added each time for up to 17 days.

Dissociation of V2a Interneuron Cultures

V2a interneuron cultures were dissociated by incubating each 24-well with 1 ml Accutase. Cultures were incubated for 45 minutes total with a trituration every 15 minutes. At the end of the incubation period, the dissociated cells were washed with PBS and centrifuged at 200×g for 5 minutes to pellet the cells.

Enrichment with Replating

The day 17 cultures were replated by first dissociating the cultures as described above. The pelleted cells were resuspended in NIM supplemented with 0.4 μg/ml AA, 10 ng/ml BDNF, 100 nM RA, 100 nM pur, 1 μM DAPT and with 1 μM or 10 μM ROCK inhibitor and plated onto a fresh Matrigel-coated 24-well plate. While the exact cell density was not calculated, the total contents of one dissociated 24-well was replated back onto one 24-well. Cultures were incubated at 37° C. for 3 days before analysis.

WNT Treatment

To examine pretreatment effects of WNT, hiPSCs were plated onto a Matrigel-coated 24-well plate at 125,000 cells/cm$^2$ in mTeSR supplemented with 10 μM ROCK inhibitor and 2 μM CHIR99021. Two days later, the cell layers were dissociated with Accutase and the differentiation was performed as described above with the addition of 2 μM CHIR99021. The CHIR99021 treatment was continued until day 7.

Single Cell RNA Sequencing

At Day 17 of culture, cells were dissociated with Accutase. Approximately 8,000 cells were prepared for single cell analysis through droplet encapsulation by the Chromium Controller and library preparation with the Chromium Single Cell 3' v2 Library and Gel Bead Kit (10× Genomics, San Francisco, CA). cDNA was sheared using a Covaris S2 sonicator and 12 PCR cycles were run during cDNA amplification. Libraries were sequenced on a HiSeq 4000 (Illumina, San Diego, CA). Sequences were demultiplexed and aligned to human reference genome GRCh38 using the default settings of 10×Genomics *Cellranger* v 1.2. Genes were annotated using Ensembl version 70 (Dobin, Davis et al. 2013). After *Cellranger* filtering, >85 million valid reads remained with >70% mapping to the transcriptome. Downstream analysis was performed using Seurat (Macosko, Basu et al. 2015, Satija, Farrell et al. 2015) and cells not expressing between 200 and 6000 unique genes were removed. A subset of high-variance genes was determined using Seurat's "Mean VarPlot" function (expression cutoff of ≥0.0125; dispersion cutoff of ≥0.50) and used to group cells into clusters (principal components 1-15; cluster resolution parameter=0.6) (van der Maaten LJP 2008). The top 20 differentially expressed genes for each cluster were plotted in the heatmap.

US 12,577,530 B2

39

Flow Cytometry

At day 17 of differentiation, cells were completely dissociated as described in 3.3.3 and stained with the Transcription Factor Buffer Set, which includes a fixation/permeabilization (FP) and wash/permeabilization (WP) buffer (BD Biosciences, Franklin Lakes, NJ). Dissociated samples were first fixed for 45 minutes at 4° C. in the FP buffer followed by a 20-minute block with WP buffer containing 5% normal donkey serum (NDS, Jackson Laboratory, Bay Harbor, ME). Primary antibodies against CHX10, LHX5, PHOX2A, and PHOX2B (Table 1) and the proper matching species isotype control were added into WP buffer containing 2% NDS and incubated at 4° C. for 45 minutes. After two washes with WP buffer, secondary antibodies donkey anti-mouse IgG, ALEXA FLUOR™ 488 (a fluorescent compound; Life Technologies), at a dilution of 1:200, were added to WP buffer and incubated at 4° C. for 45 minutes. After two washes with WP buffer, samples were passed through a 35-µm filter before assessing with a BD ACCURI™ C6 (BD) cytometer (minimum 10,000 events). Cytometry analysis was performed using FlowJo V10 (Flowjo, Ashland, OR).

TABLE 1

Antibodies used for flow cytometry and immunostaining

| Antibody Target | Species | Vendor | Cat. Number | Application | Dilution |
|---|---|---|---|---|---|
| CHX10 | mouse | Santa Cruz | sc-374151 | Flow and ICC | 1 to 1000 |
| LHX5 | goat | R&D | AF6290 | Flow and ICC | 1 to 250 |
| PHOX2A | mouse | Santa Cruz | 81978 | Flow and ICC | 1 to 250 |
| PHOX2B | mouse | Santa Cruz | 376997 | Flow | 1 to 500 |
| PHOX2B | goat | R&D | AF4940 | ICC | 1 to 250 |
| Mouse IgG1 Isotype Control | mouse | R&D | MAB002 | Flow | Matched protein concentration |
| Normal Goat IgG Control | goat | R&D | AB-108-C | Flow | Matched protein concentration |

In Vitro Immunocytochemistry and Imaging

Samples were fixed using 4% paraformaldehyde (VWR) for 30 minutes and permeabilized using 0.1% Triton-X in PBS for 15 minutes at 4° C. before blocking for 1 hour at 4° C. with PBS containing 5% NDS. Primary antibodies (Table 1) were diluted in PBS containing 2% NDS and incubated overnight. Samples were washed three times with PBS for 15 minutes at room temperature before incubating with secondary antibodies (Life Technologies) diluted in PBS containing 2% NDS. Hoechst was added at 1:1000 to the samples for 10 minutes then washed and imaged using a Zeiss Axio Observer inverted wide-field microscope equipped with an Apotome structured light attachment. An average intensity projection was performed on Z-stack images to create a single two-dimensional image spanning the entire thickness of the observed field. Images were cropped using Photoshop.

Statistical Analysis

Statistical analysis was performed using Prism 6 software. The mean and #standard deviation were calculated for a minimum of three biological replicates for all data unless otherwise noted. Unpaired t-tests were performed when comparing two groups. One-way analysis of variance (ANOVA) followed by appropriate post hoc pairwise comparisons Tukey's tests were used when three or more groups were specified. Specific statistical analysis is mentioned within the corresponding figure legend. Variances were confirmed to not differ significantly with the Brown-Forsythe test. In all comparisons, significance was defined as $p \leq 0.05$.

Results

V2a Interneuron Enrichment Through Replating and WNT Activation

Figure 1A:
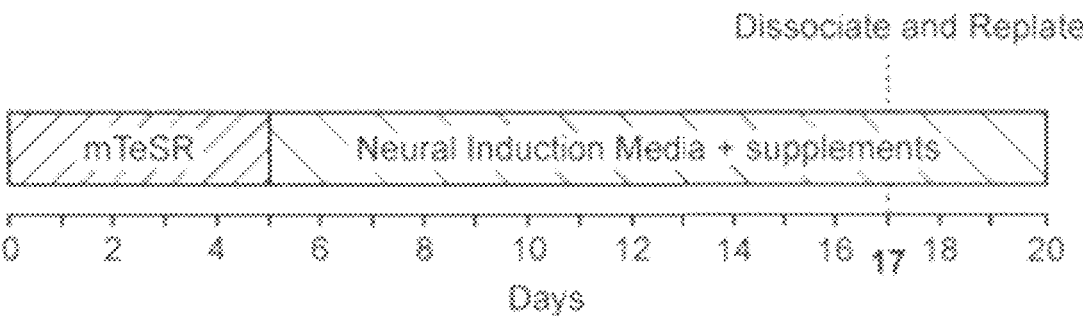
FIGS. 1A-1C show that replating enhances the V2a interneuron population.
Figure 1B:
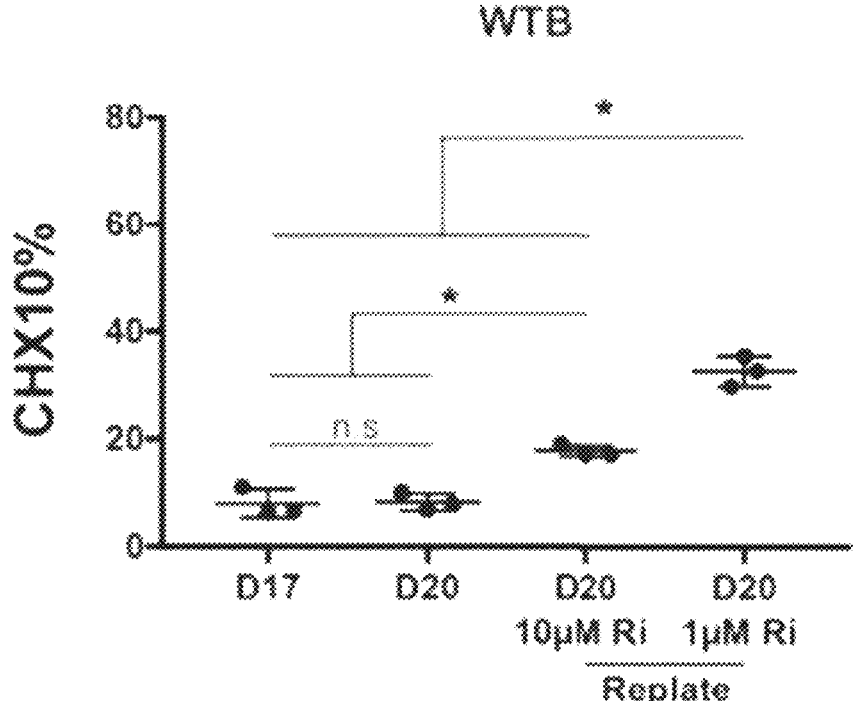
Figure 1C:
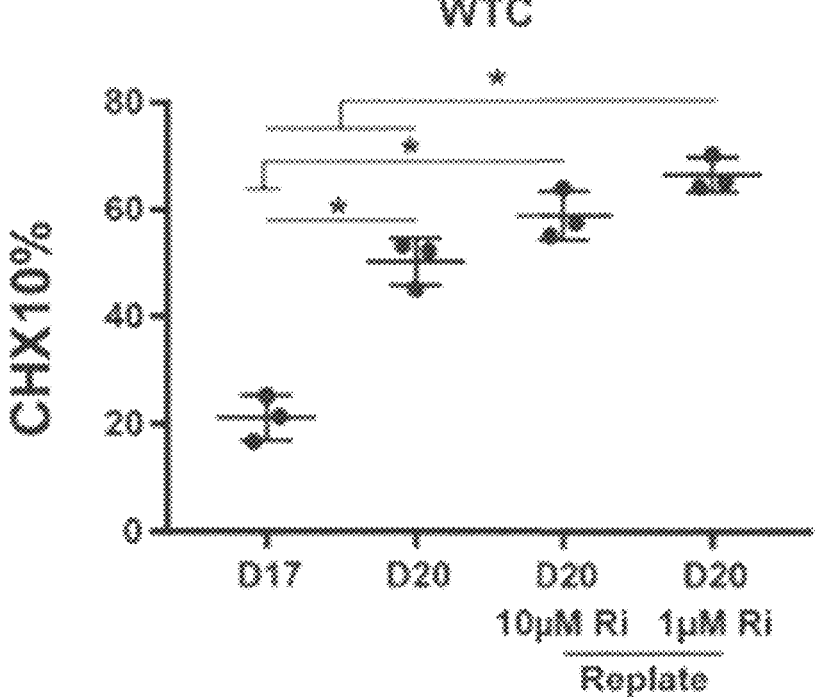

While Butts et al described a defined protocol to obtain V2a interneurons, identified through expression of the CHX10 transcription factor, the percentages consistently obtained from the protocol (~20%) left room for improvement. V2a interneuron cultures were dissociated and replated at day 17 in the presence of either 1 or 10 µM ROCK inhibitor and cultured for an additional 3 days (FIG. 1A). In two different cells lines (WTB and WTC iPSCs), replating enriched the CHX10% over cultures differentiated for 17 days (FIGS. 1B-1C). Culturing for an additional 3 days (Day 20) without replating increased the percentage of CHX10+ cells with the WTC cell line but not with the WTB indicating there are some differences in optimal culture duration between the two cell lines. The disparity between culture duration could be caused by differing growth rates between the cell lines causing confluency to be reached at different time points, which would effect endogenous signaling and rate of differentiation. This may suggest that a range of termination time points should first be tested for each cell line. However, with both cell lines, replating with 1 µM ROCK inhibitor enriched the CHX10 percentage over D20 time-matched controls implicating that replating step will enrich the CHX10 population regardless of baseline levels. However, It appears that the fold-increase of the enrichment is dependent on baseline differentiation levels. The CHX10 percentage was enriched ~3-fold and ~1.5-fold in the WTB and WTC10 cell lines, respectively. Therefore, if the baseline levels of CHX10 are low, replating can be performed to further enrich the V2a interneuron population.

Figure 2A:
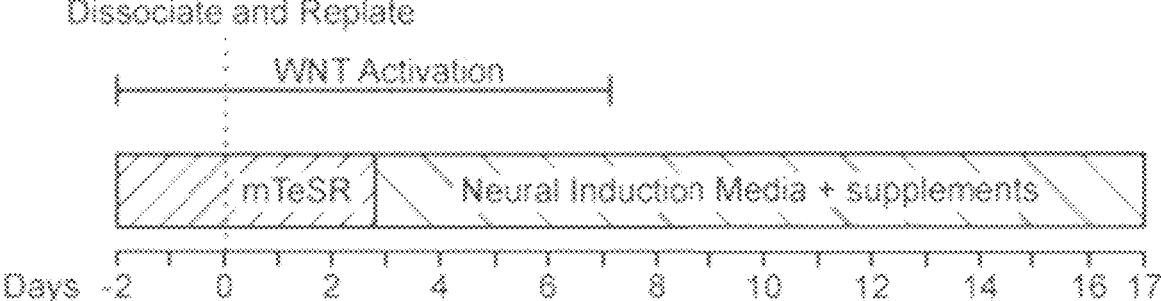
FIGS. 2A-2C show that early WNT activation enhances the V2a population.
Figure 2B:
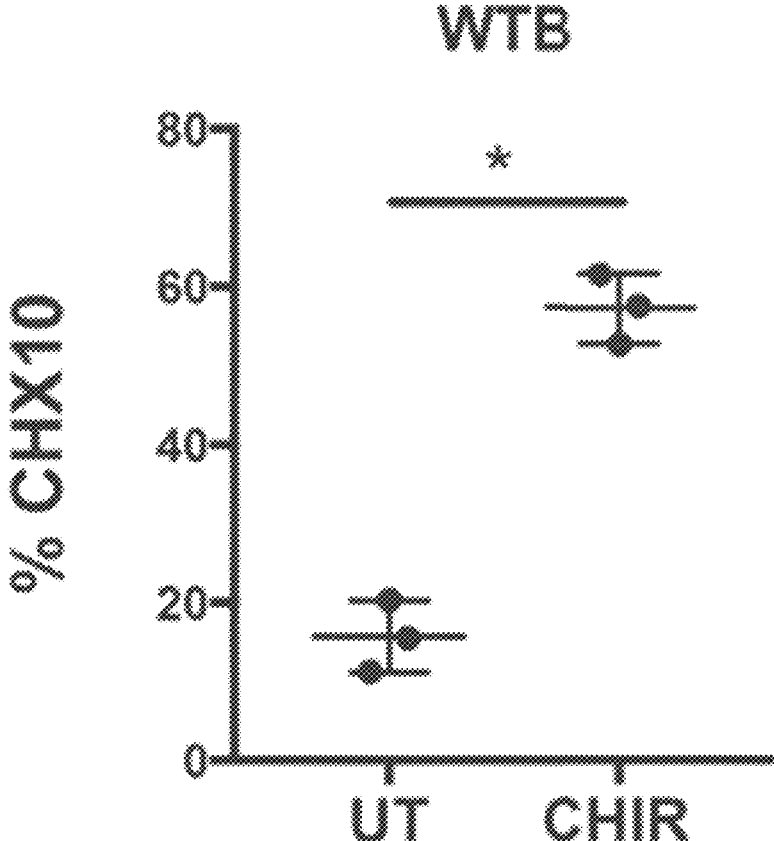
Figure 2C:
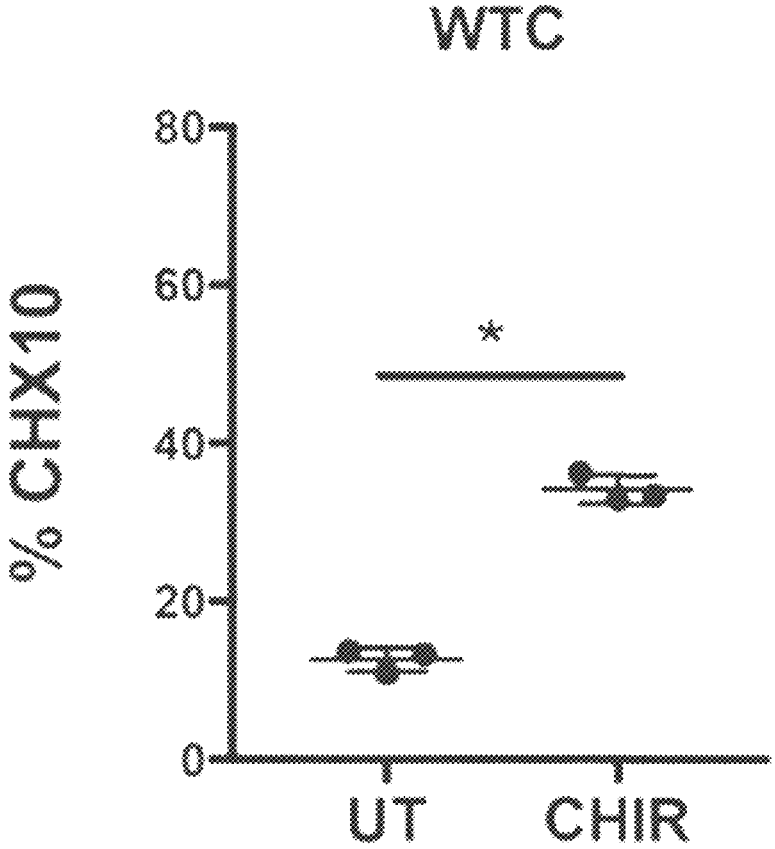

Activation of the WNT signaling pathway has been demonstrated to promote neural induction and caudalization (Elkouby and Frank 2010, Li, Sun et al. 2011, Maury, Come et al. 2015). Activation of the WNT pathway using the small molecule CHIR 99021 has been added into motor neuron differentiation protocols not only to caudalize the population but also increase the efficiency of differentiation (Du, Chen et al. 2015, Shimojo, Onodera et al. 2015). To test WNT activation in our differentiation, hiPSCs were plated at a high density in mTeSR supplemented with CHIR 99021 for two days. The cells were then dissociated and replated to begin the differentiation as previously described but CHIR 99021 was supplemented in the media for the first 7 days of the protocol (FIG. 2A). CHX10 percentage was increased when CHIR 99021 was added into the differentiation compared to the untreated (UT) controls in both WTB and WTC hPSCs (FIGS. 2B-2C). However, the effectiveness of the fold-change increase appeared to be cell line specific. Reports have demonstrated the response of hPSC cell lines to CHIR 99021 may depend on the concentration (Lippmann, Williams et al. 2015). Since this study only tested one concentration of CHIR 99021, it is possible that a higher concentration of CHIR may need to be used with the WTC cell line. These data support that the addition of WNT signaling could be used to enhance the V2a phenotype in the differentiation by either increasing the efficiency of neuralization or by defining a rostocaudal region that promotes V2a specification.

Characterization of Heterogeneous V2a Interneuron Cultures

Figure 3A:
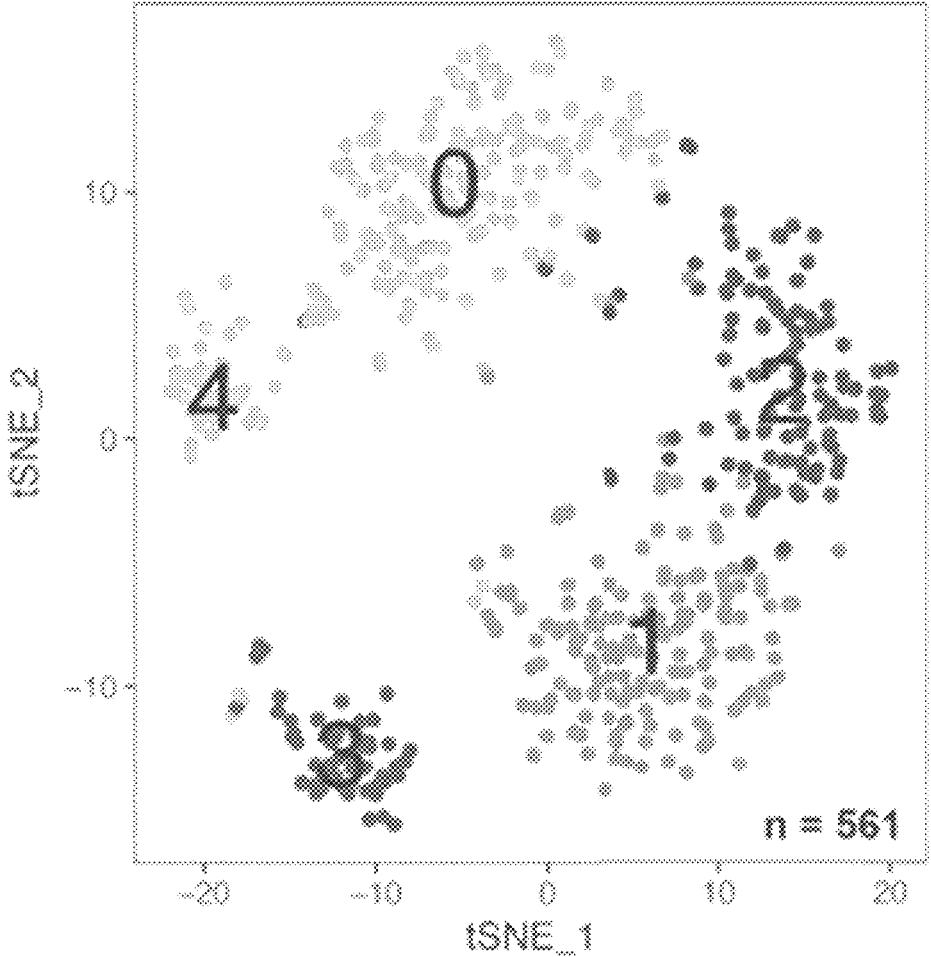
FIGS. 3A-3D show single cell RNA sequencing of replated differentiation.
Figure 3B:
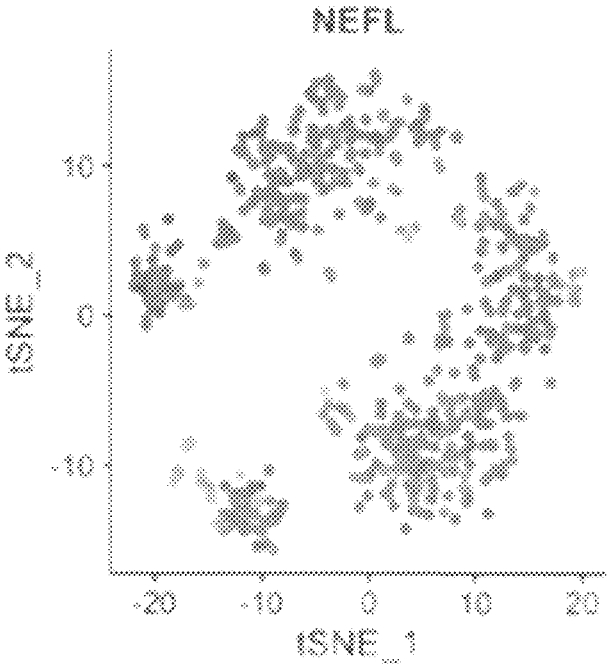
Figure 3C:
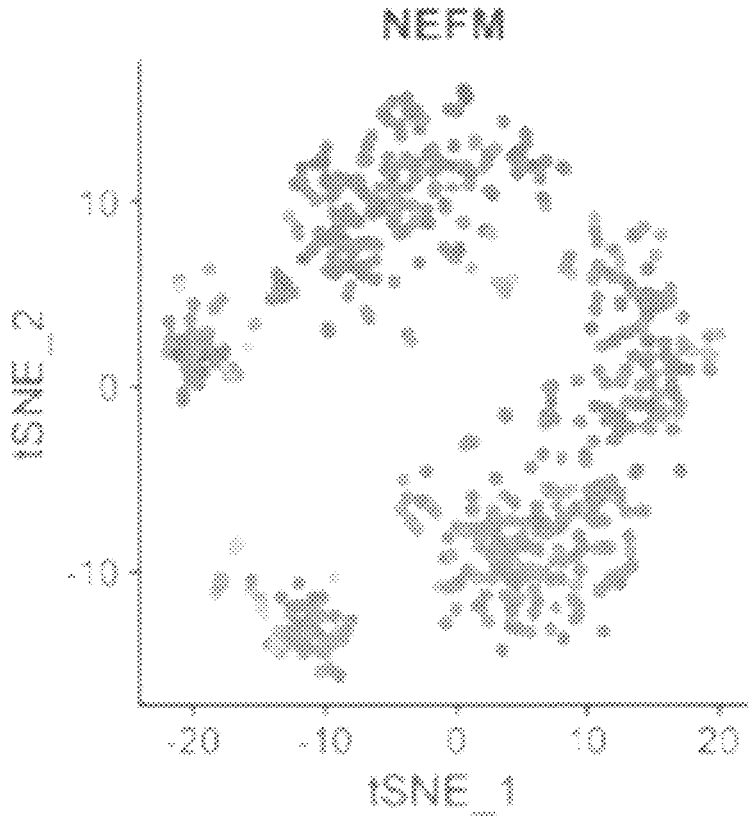
Figure 3D:
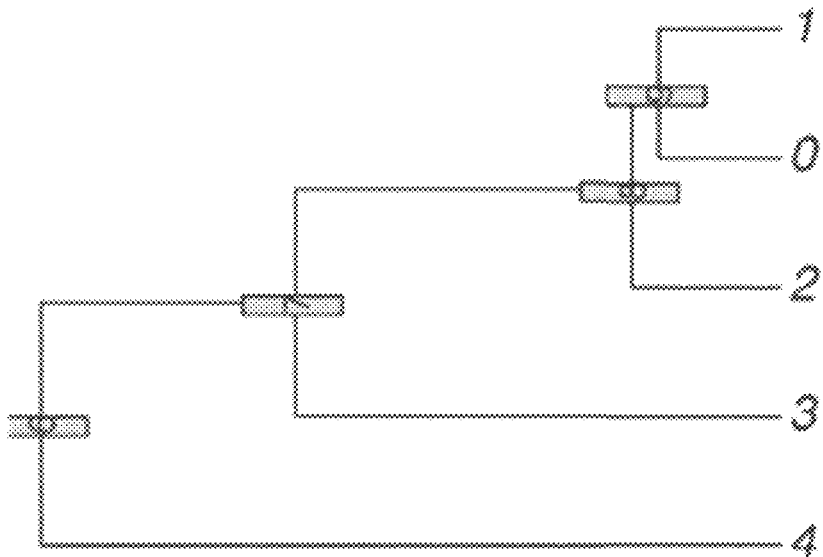
Figure 4:
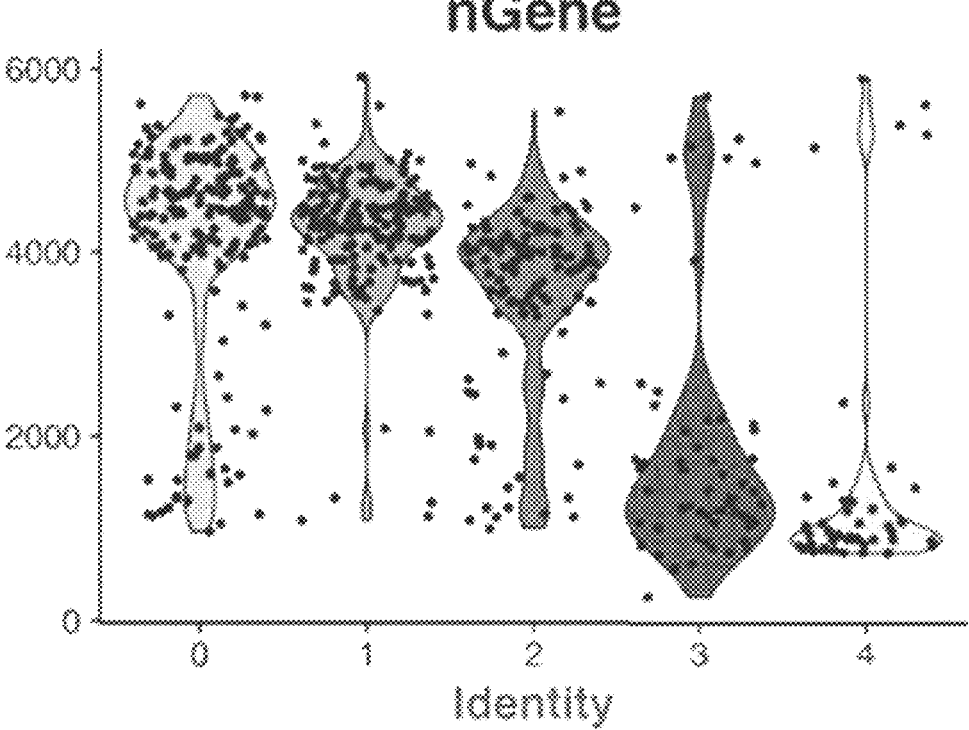
FIG. 4 shows an imbalanced gene count between clusters. Clusters 3 and 4 have lower numbers of genes per cell making cluster identification difficult.

Single cell RNAseq was performed on the enriched V2a interneuron cultures that were replated for 3 days with 1 µM ROCK inhibitor. For this data set, 561 cells were captured at 102,361 reads per cell and 4,138 genes per cell. Using 15 principle components and a resolution of 0.6, the tSNE plot revealed 5 distinct clusters that represented the heterogeneous population (FIG. 3A). The population appeared to be mainly neuronal as revealed through expression of neurofilament light and medium (NEFL, NEFM) (FIG. 3B-C). Dendrogram classification revealed that clusters 0, 1 and 2 are closely related while clusters 3 and 4 have more differences (FIG. 3D). Interestingly, when the number of genes per cell was plotted as a function of cluster (FIG. 4), it was clear that cells in clusters 3 and 4 had fewer genes per cell (~1000) compared to clusters 0 to 2 (>4,000) meaning lower abundance genes such as transcription factors were not being sequenced making identification of neural subtype identity difficult. This disparity may be an artifact of library preparation or sequencing. For additional analysis, these two clusters could be filtered out.

Figure 5A:
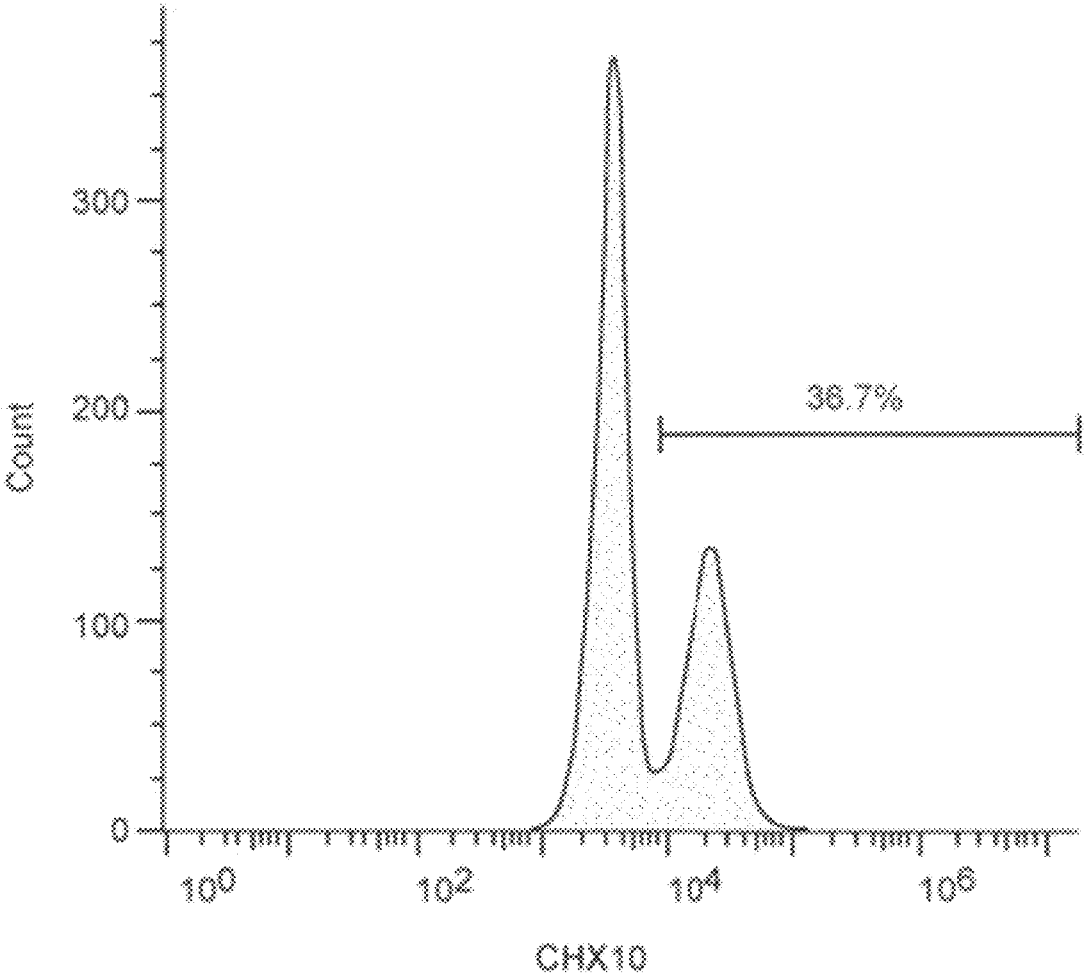
FIGS. 5A-5E show identification of V2a interneuron population.
Figure 5B:
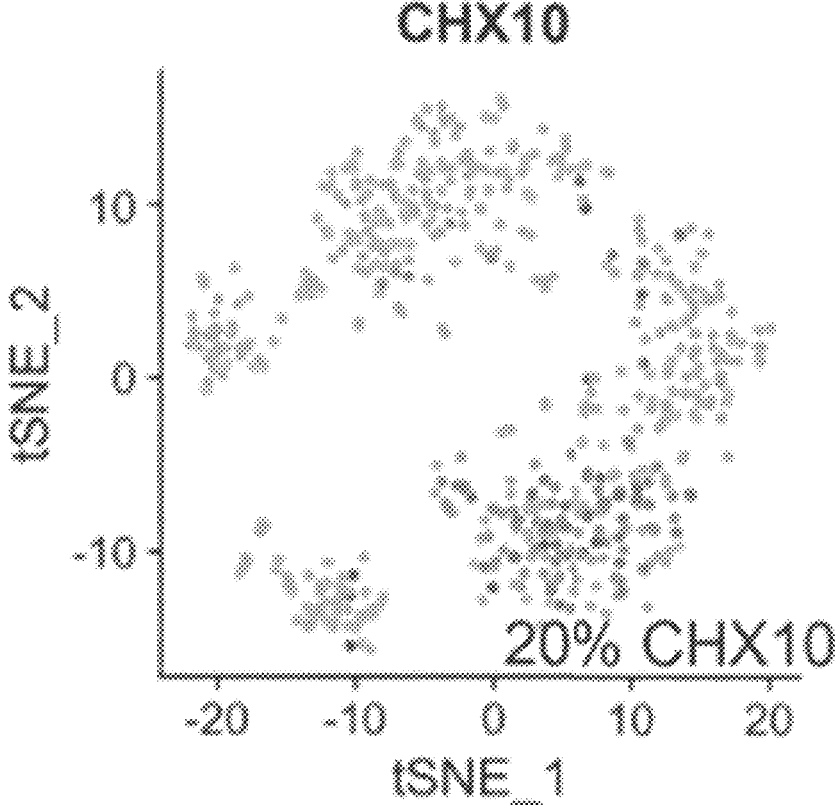
Figure 5C:
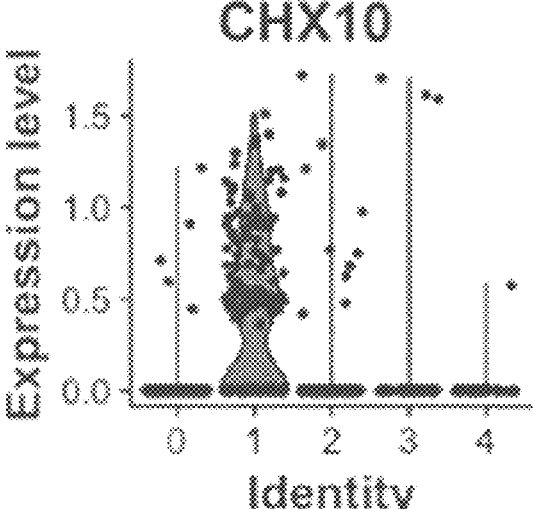
Figure 5D:
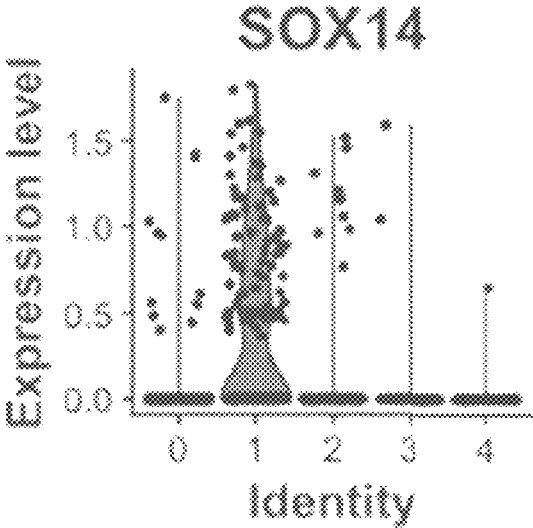
Figure 5E:
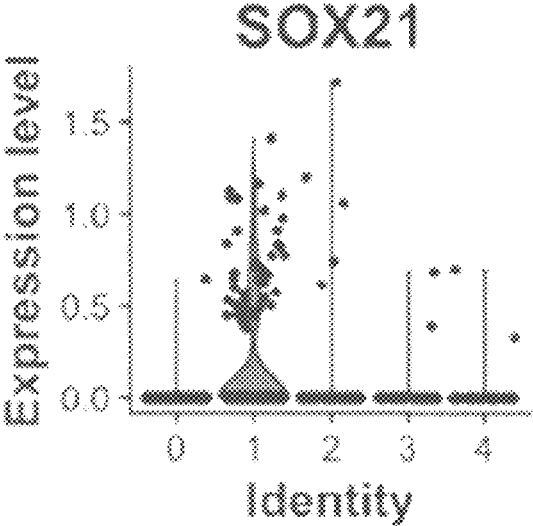

The V2a interneuron analyzed in the single cell analysis was approximately 36% CHX10+ via flow cytometry (FIG. 5A). Approximately 20% percent of cells were detected to express ('HX10 by single cell analysis and these cells were primarily contained within cluster 1 (FIG. 5B). Additional transcription factors that mark V2a interneurons including SOX14 and SOX21 were detected and contained within cluster 1 (FIGS. 5C-5E) reinforcing that cluster 1 represents the V2a interneurons in the cultures.

Figure 6:
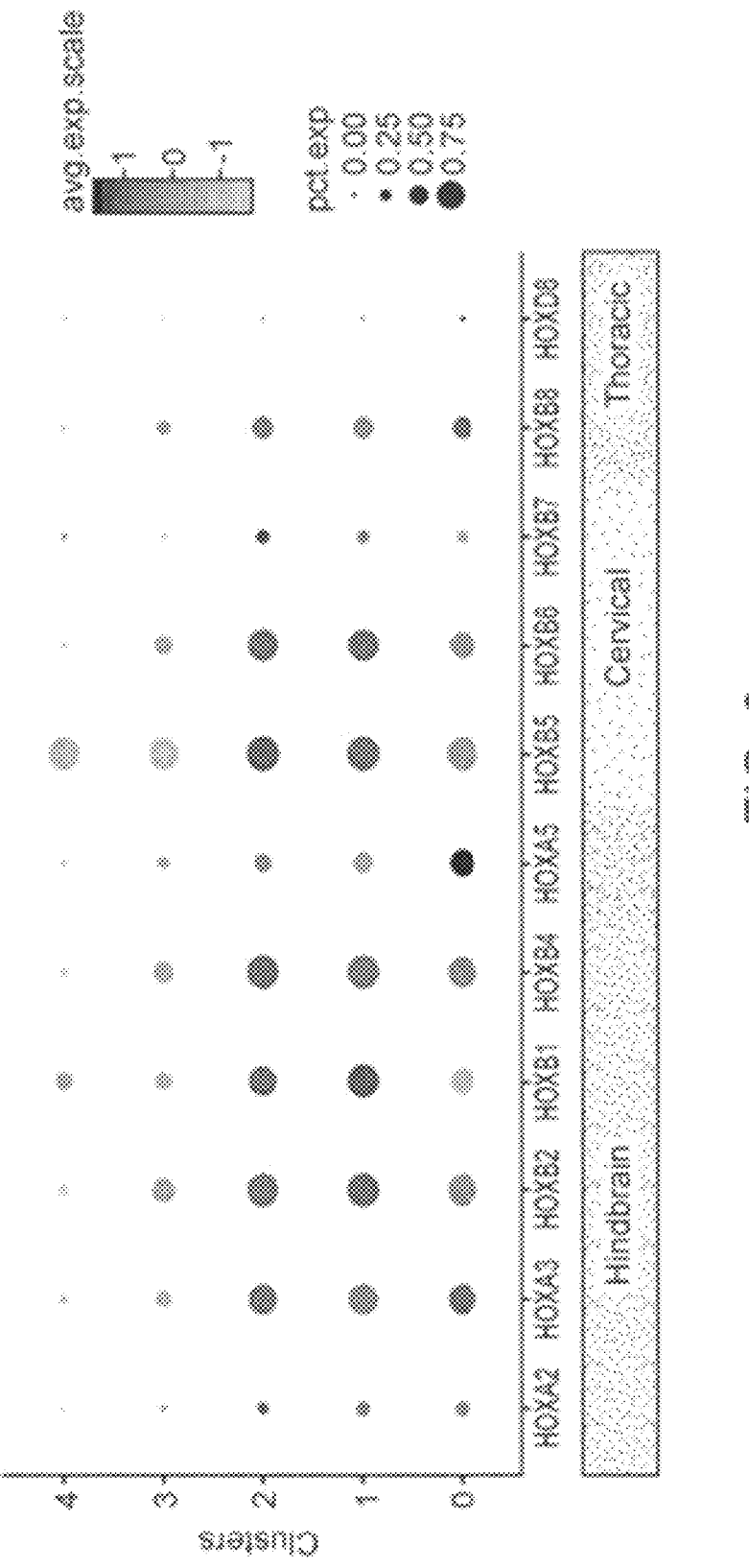
FIG. 6 shows a HOX expression profile. Expression level of various HOX genes in each cluster. The size of the dot correlates to the number of cells within the cluster that express the gene. The color of the dot correlates to the relative expression level.

Physiologically, V2a interneurons are found throughout the rostral-caudal axis of the brainstem and spinal cord (Crone, Quinlan et al. 2008, Zhong, Droho et al. 2010, Crone, Viemari et al. 2012, Azim, Jiang et al. 2014) To identify the regional identity of the differentiated cultures, expression of a range of HOX markers from the hindbrain to the sacral region was analyzed. HOX genes present in the hindbrain (HOXA2, HOXA3, HOXB2, HOXB1 and HOXB4) and cervical regions (HOXA5, HOXB5, HOXB6, HOXB7, and HOXB8) were detected in clusters 0 to 3 (FIG. 6). The midbrain gene (OTX2) and Hox genes for thoracic/lumbar regions (HOXB9, HOXB10, HOXB11) were not detected. This HOX profile indicates the cultures have expression patterns of a hindbrain/high cervical regional identity.

Identification of Hindbrain Neuronal Populations

Figure 7:
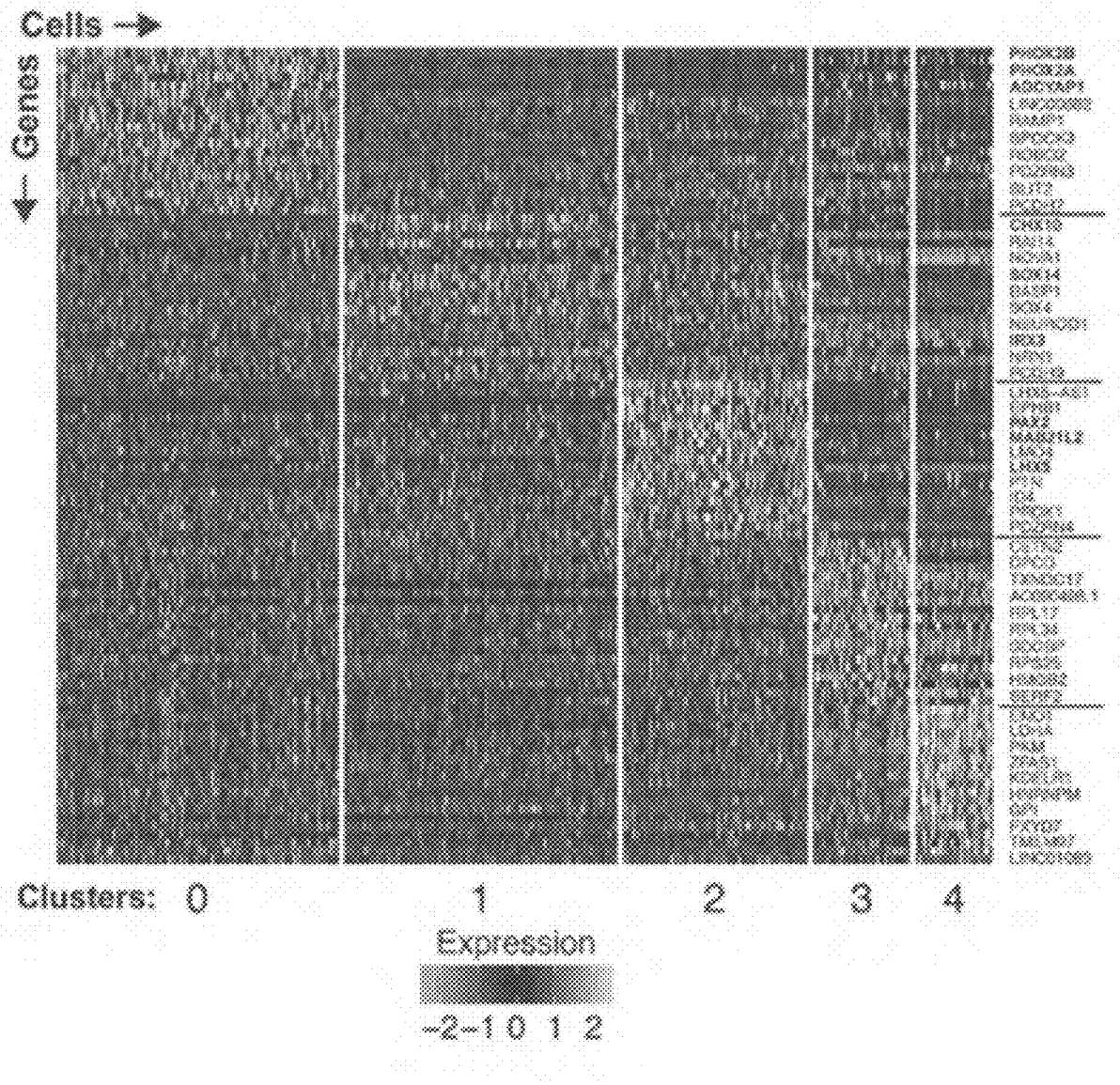
FIG. 7 shows a heatmap of genes that define each cluster. A heatmap is shown of the top 20 expressed genes for each cluster. Expression values are normalized for each gene. The top 10 genes are listed for each cluster. Genes found in respiratory hindbrain populations are bolded.
Figure 8A:
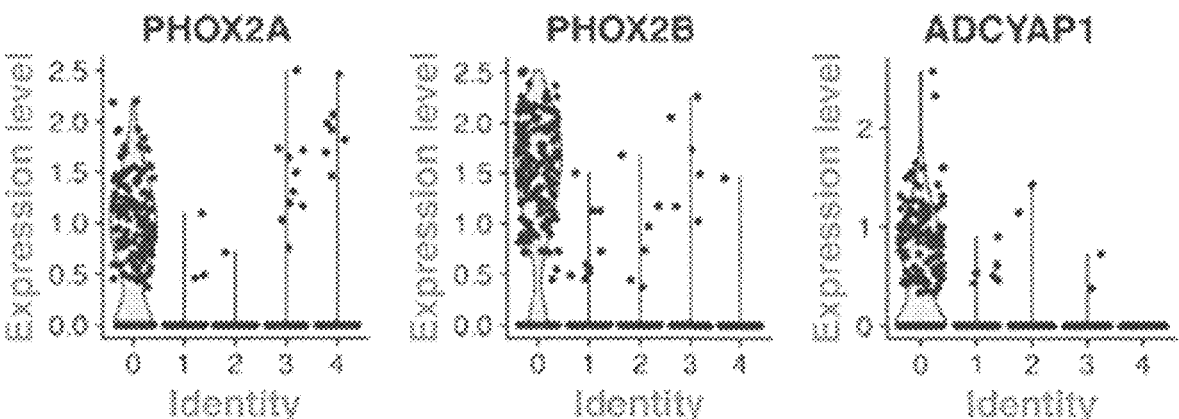
FIGS. 8A-8C show that clusters contain populations involved with respiratory control. Violin plots of genes from the top 10 genes that are expressed in (FIG. 8A) chemosensing neurons, (FIG. 8B) V2a interneurons, and (FIG. 8C) V0 interneurons.
Figure 8B:
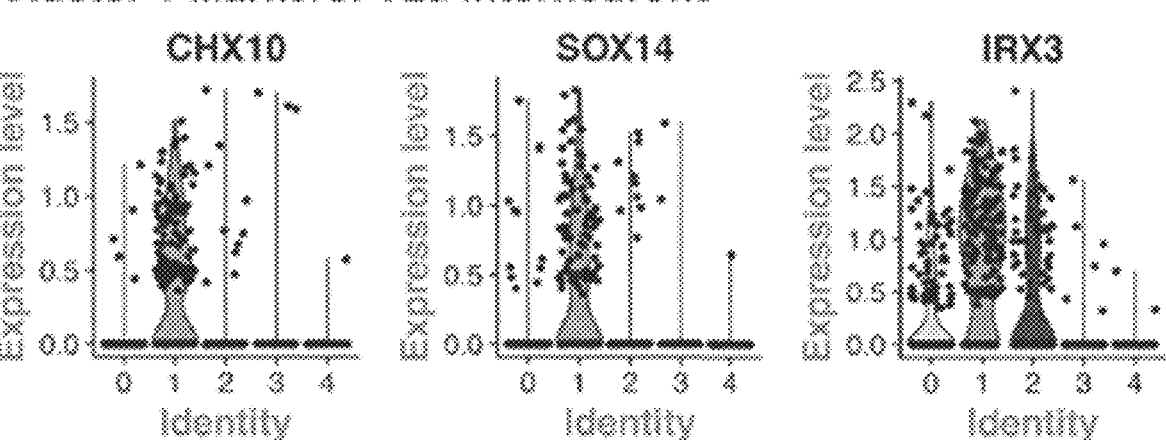
Figure 8C:
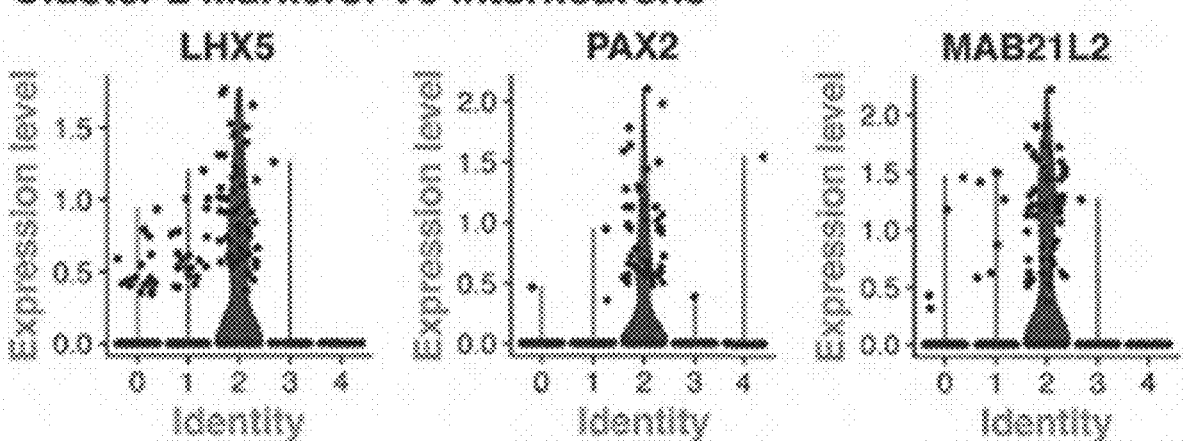
Figure 9A:
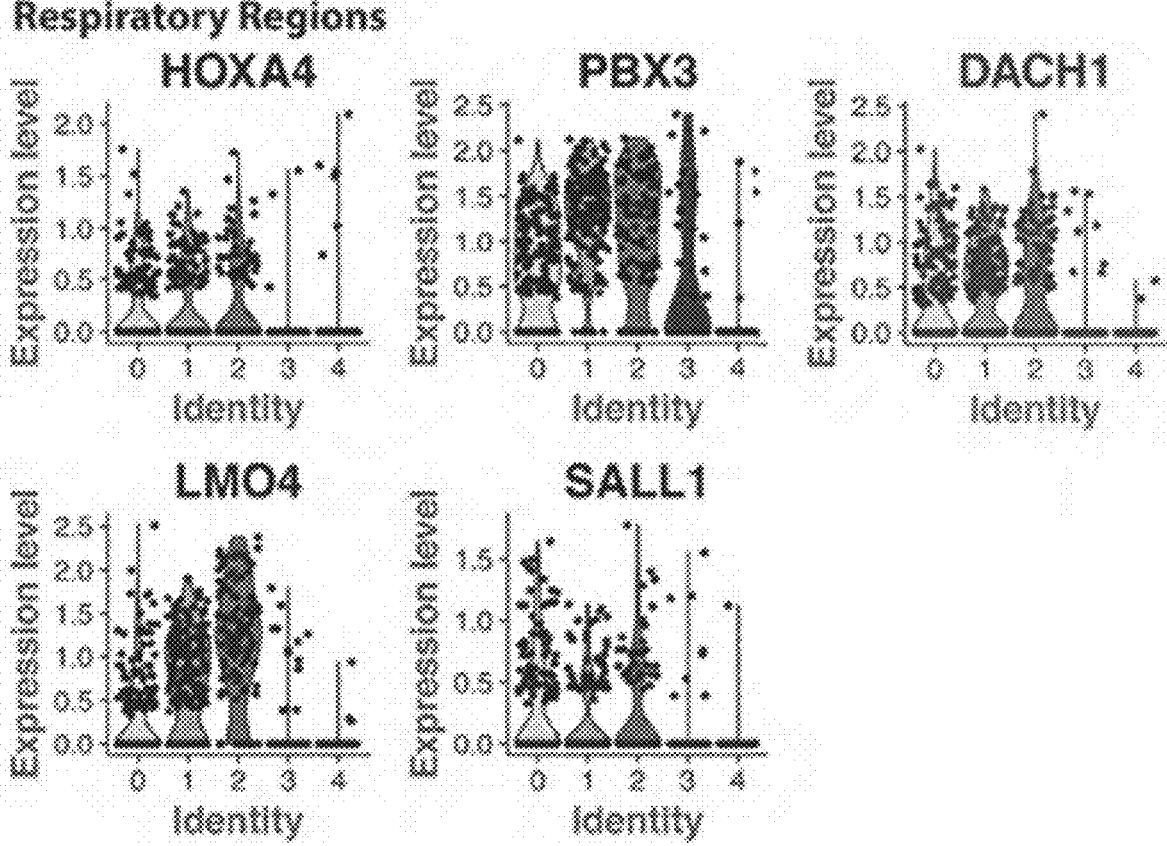
FIGS. 9A-9B show confirmation of respiratory phenotype.
Figure 9B:
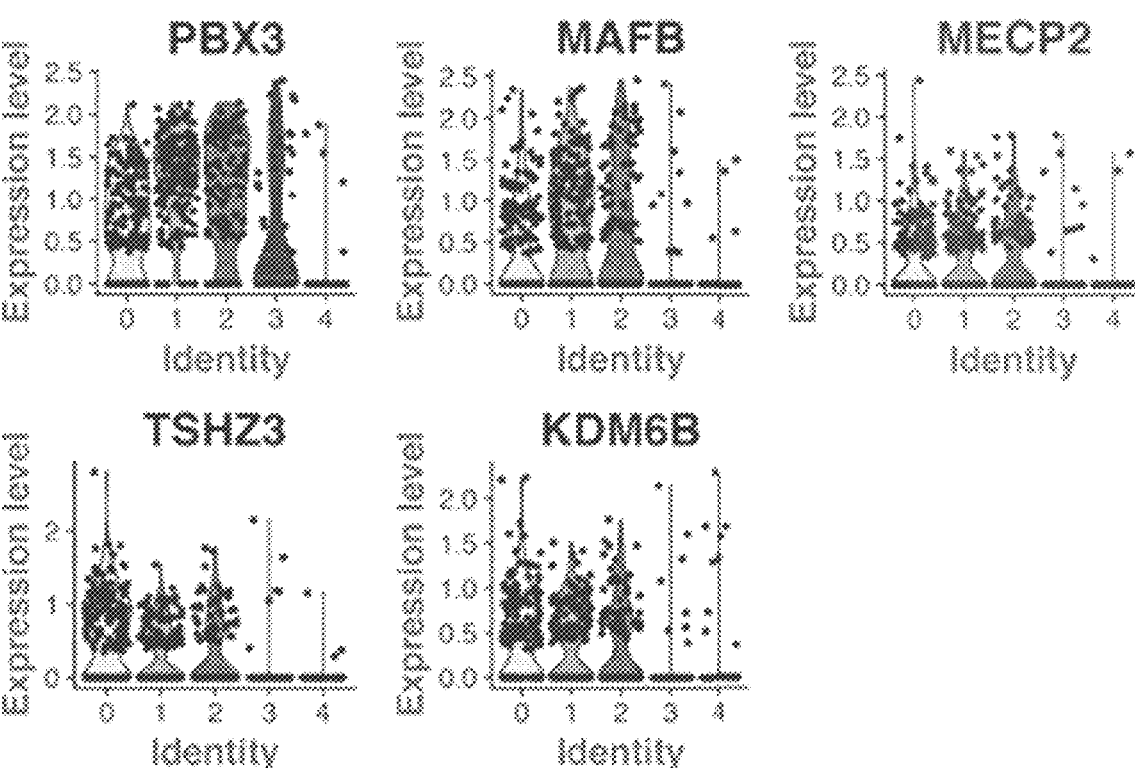

Cluster 1 was identified as the V2a interneurons, however, the identities of clusters 0, 2, 3 and 4 were unknown. Differential gene expression analysis was performed to detect genes that were upregulated in one cluster compared to all other clusters. The heatmap depicts the top 20 most differentially expressed genes for each cluster with the top 10 genes labeled for each cluster (FIG. 7) For clusters 0 through 2, transcription factors present in the respiratory hindbrain circuit were highly upregulated (bold). More specifically, Cluster 0 expressed high levels of PHOX2B, PHOX2A, and ADCYAP1, which are markers of chemosensing neurons that are present in the retrotrapezoid nucleus (FIG. 8A). Cluster 1 expressed high levels of CHX10, SOX14, and IRX3, markers of committed and progenitor V2a interneurons (FIG. 8B). Cluster 2 expressed high levels of LHX5, PAX2, and MAB21L2, markers of V0 interneurons located in the pre BötC (FIG. 8C) (Hayes, Kottick et al. 2017). Additionally, clusters 0, 1 and 2 had high expression of markers found in respiratory hindbrain regions including the BötC and pre BötC (HOXA4, PBX3, DACH1, LM04, SALLI, FIG. 9A (Yackle, Schwarz et al. 2017) as well as genes that when mutated, lead to respiratory dysfunction (PBX3, MAFB, MECP2, TSHZ3, and KDM6B, FIG. 9B, (Amir, Van den Veyver et al. 1999, Shahbazian and Zoghbi 2001, Blanchi, Kelly et al. 2003, Rhee, Arata et al. 2004, Burgold, Voituron et al. 2012). Together, the single cell transcriptional analysis supports that the culture contains several different neural subtypes present in the respiratory hindbrain circuit.

TABLE 2

| Top differentially expressed genes for each cluster from heatmap | | | | |
| Cluster 0 | Cluster 1 | Cluster 2 | Cluster 3 | Cluster 4 |
| --- | --- | --- | --- | --- |
| 1 PHOX2B | VSX2 | LHX5-AS1 | CETN2 | ENO1 |
| 2 PHOX2A | RAI14 | EPHB1 | DPCD | LDHA |
| 3 ADCYAP1 | NOVA1 | PAX2 | TXNDC17 | PKM |
| 4 LINC00682 | SOX14 | MAB21L2 | AC090498.1 | ZFAS1 |
| 5 RAMP1 | BASP1 | LMO4 | RPL17 | KDELR1 |
| 6 SPOCK3 | SOX4 | LHX5 | RPL34 | HNRNPM |
| 7 ROBO2 | NEUROD1 | PTN | SDCBP | GPI |
| 8 PDZRN3 | IRX3 | ID4 | RPS25 | FXYD7 |
| 9 SLIT2 | NRN1 | PROX1 | HMGB2 | TMEM97 |
| 10 PCDH7 | PCDH9 | PDZRN4 | SERF2 | RPL12 |
| 11 EBF1 | RND3 | MYCBP2 | GNG5 | LINC01089 |
| 12 ID2 | CCBE1 | LAMP5 | EEF1D | DOK5 |
| 13 TLN2 | PPP2R2B | LHX1 | EIF3E | CNN2 |
| 14 SPOCK1 | CRNDE | LRRN1 | ATP5I | FSTL1 |
| 15 SH3BGRL | CRABP2 | ARL4C | TAGLN2 | RPL39 |
| 16 ZFHX3 | GNAS | TNRC6C | TIMP1 | PPP1R1A |
| 17 ZNF385D | KCNIP4 | PIK3R1 | SNRPG | WDR66 |
| 18 HOXA5 | SYT1 | ANOS1 | B2M | S100A6 |
| 19 ASCL1 | TLE1 | TSHZ2 | RPL12 | PRPH |
| 20 LMO3 | RHOB | PCDH9 | MTRNR2L12 | NEAT1 |

In Vitro Confirmation of Hindbrain Populations

Figure 10A:
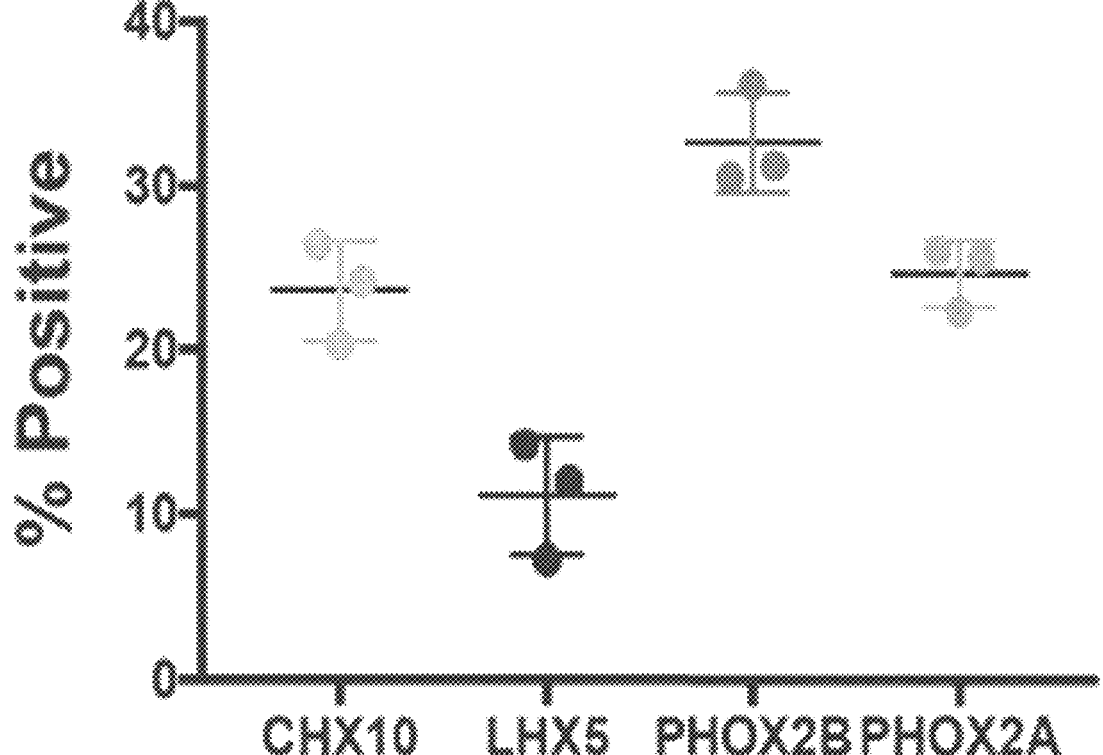
Figure 10B:
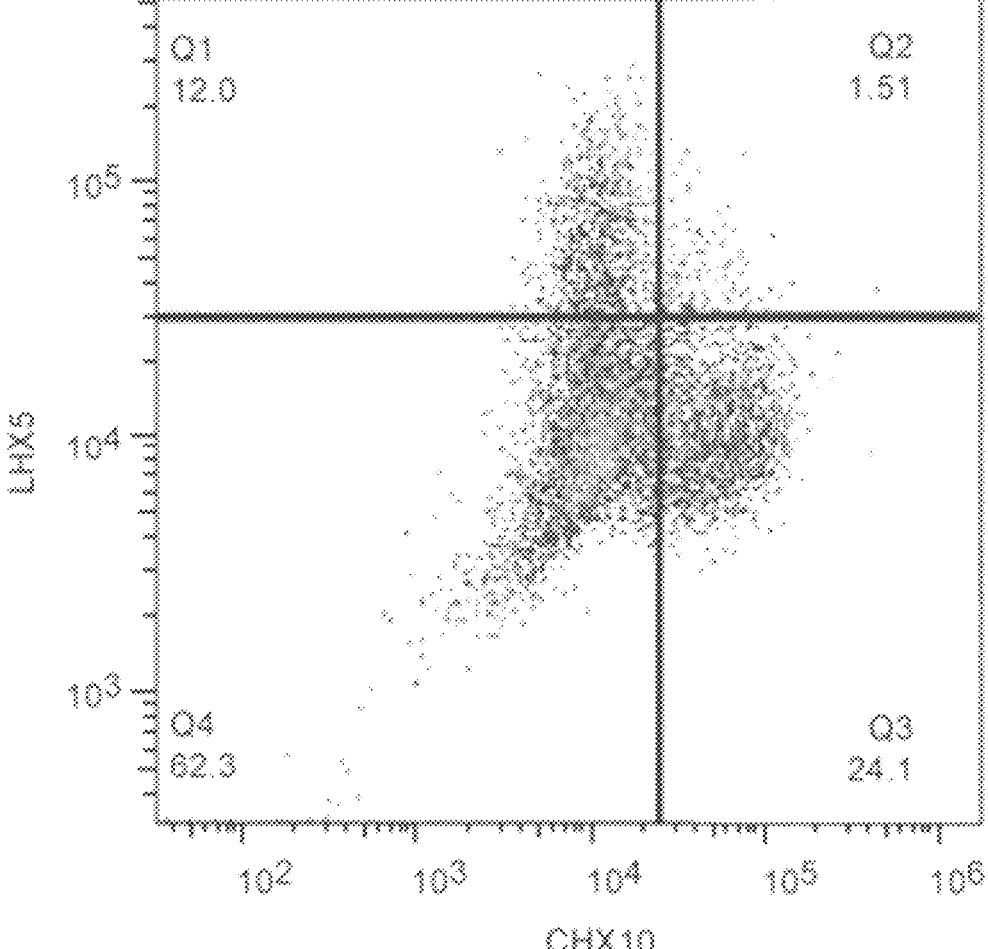
Figure 10D:
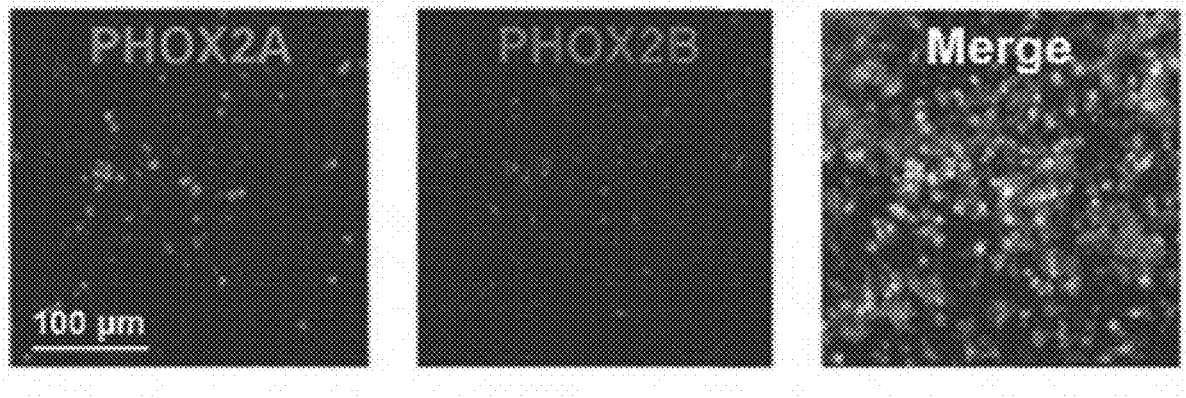
Figure 11A:
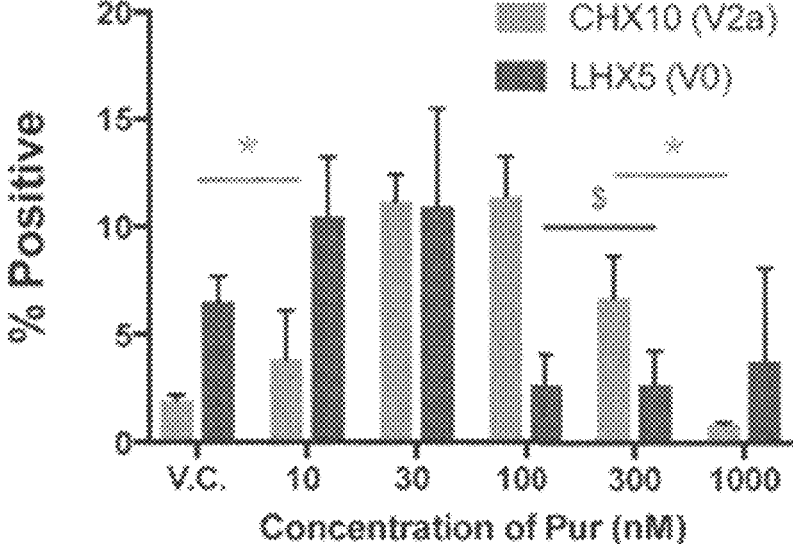
FIGS. 11A-11B show modulation of V2a and V0 interneuron in response to purmorphamine and retinoic acid concentration.
Figure 11B:
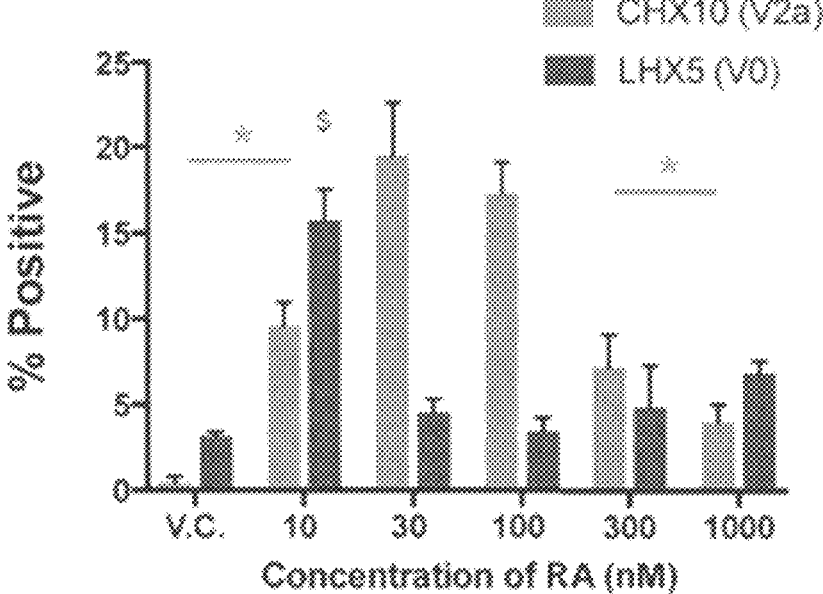
Figure 128:
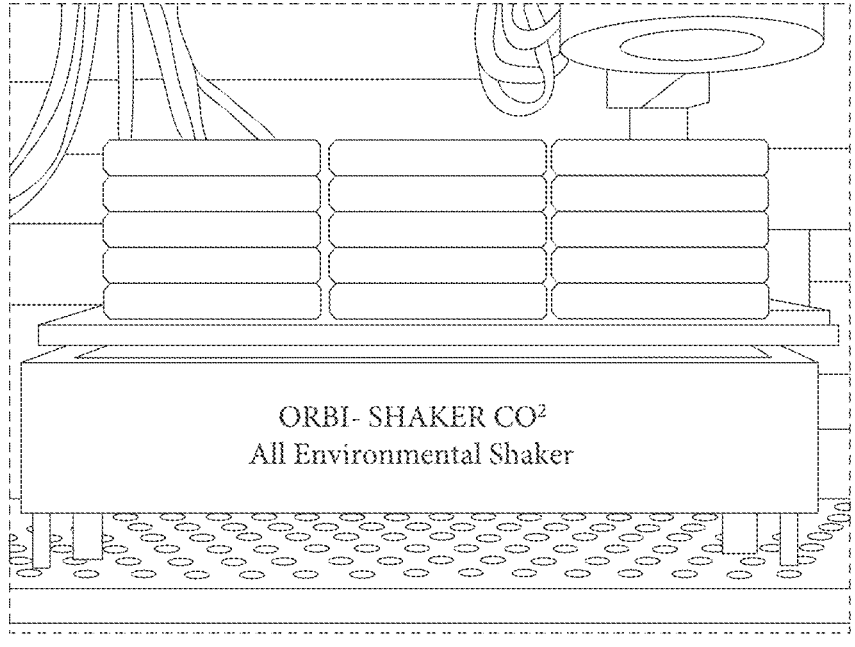

While the single cell RNA sequencing findings of a chemosensing and V0 interneuron were plausible given the signaling cues that were being provided, the results were confirmed in in vitro cultures. At day 17, CHX10, LHX5, PHOX2A, and PHOX2B were identified in the cultures at percentages similar to the single cell RNA sequencing representations (for cytometry: 23.6%, 11.2%, 24.6%, and 32.6%, respectively, FIG. 10A). Additionally, CHX10 and LHX5 were confirmed to be separate populations by dual staining and separation on the cytometry dot plot (FIG. 10B). Immunocytochemistry at day 17 confirmed the protein of all markers were present and distributed similarly throughout the dense cultures (FIGS. 10C-10D). Cultures were then dissociated and replated for 6 days to observe colocalization and neurite outgrowth. CHX10 and LHX5 expression was not co-localized, which visually confirmed the V2a and V0 interneurons as separate cell populations (FIG. 10E). As demonstrated by the single cell RNA sequencing, there was overlap of PHOX2A and PHOX2B expression (pointed arrowheads, FIG. 10F). However, PHOX2A-/PHOX2B+ (full arrowheads) but not PHOX2A+/PHOX2B- cells were detected potentially indicating that PHOX2B expression precedes PHOX2A expression (FIG. 10F). All of these populations were expressed Bill Tubulin, a neuronal marker, and have extensive neurite outgrowth (FIGS. 10E-10F). In vitro confirmation of transcription factor expression identified in clusters 0 through 2 (PHOX2B and PHOX2A, CHX10, and LHX5) gives further support that the protocol yields V2a, V0, and chemosensing neurons.

Manipulation of Hindbrain Interneuron Populations in Response to Shh and RA Treatment The hindbrain interneuron populations arise in response to RA and a ventrodorsal gradient of Shh. If Shh and RA signaling modulate these populations developmentally, it was hypothesized that the relative proportion of V2a and V0 interneurons should shift in response to changes in RA and Shh concentration in vitro. The pur concentration was varied while keeping RA concentration at 100 nM. CHX10 percentage was greater at 30 and 100 nM pur (p<0.05) while LHX5 percentage was increased at 10 and 30 nM pur compared to 100 nM pur (p<0.05, FIG. 10A). The RA concentration was then varied while keeping the pur concentration constant at 100 nM. CHX10 percentage peaked at 30-100 nM while LHX5 percentage peaked at 10 nM (FIG. 10B). These studies confirm that changing concentration of pur and RA modulates relative proportions of V2a and V0 interneurons in a way predicted by developmental gradients.

DISCUSSION

Multiple hindbrain phenotypes including V2a and V0 interneurons as well as a chemosensing population were identified by single cell RNA sequencing to be differentiated from hPSCs in response to pur, RA, and DAPT. The three populations were then identified to exist in the in vitro cultures by protein and changing pur and RA concentration could modulate the relative proportions of interneurons.

This study initially described two ways to enhance the V2a phenotype-replating and WNT activation (FIG. 1). Dissociation and replating steps have been utilized in differentiation protocols into other lineages, including cardiomyocytes, to purify the committed phenotype and deplete the stromal fraction (Burridge, Matsa et al. 2014). Following the replating step, there are some cells that do not attach. Without being bound by theory, our hypothesis is that the neuronal phenotypes have a higher ability to reattach during replating and the more proliferative cell types (including the mesenchymal and glial fraction identified in a previous single cell RNA sequencing study) are depleted, at least temporarily. This idea is supported by the single cell RNA sequencing of a replated population presented in this study wherein the mesenchymal and glial fractions are absent. One potential reason for selective adhesion may be that the mesenchymal and glial populations do not survive the dissociation process as well as the neurons, however, further experimentation will need to be performed to elucidate the mechanism that enhances the neuronal pool after replating.

Early activation of the WNT pathway was also found to increase the V2a interneuron fraction (FIG. 2B). Initially, WNT activation was explored to specify a thoracic spinal phenotype (Lippmann, Williams et al. 2015). However, once the single cell analysis revealed the hindbrain identity of the differentiation culture (FIG. 5), alternative mechanisms for WNT signaling came to light. There is a dichotomy of WNT signaling at the interface of midbrain and hindbrain development where WNT activation specifies a hindbrain phenotype and WNT signaling is inhibited in the midbrain (Ciani and Salinas 2005). Further, in studies where WNT activation alone is used as the caudalizing agent, the resulting neurons have a hindbrain/cervical phenotype and are not able to obtain a more caudal identity. In vivo, FGF and GDF11 signaling is necessary for development of thoracic and more caudal identities. This has been further supported in vitro where addition of FGFs and GDFs may be necessary to obtain thoracic phenotypes (Lippmann, Williams et al. 2015). Early activation of the WNT pathway using CHIR99021 may aid in defining the regional specificity by reinforcing hindbrain development pathways established by RA and Shh signaling.

The development of single cell RNA sequencing technologies have become a highly valuable tool in identification of heterogeneous differentiation populations. Human PSCs-derived differentiations often result in heterogeneous cultures that are only partially defined. Traditionally, large panels of antibodies or PCR primers have been used to try to identify what additional populations are present in the cultures, however, this technique is inherently biased and under-powered. Single cell analysis can provide information about $10^3$ genes present in a single cell where standard 96-well or multiplexed quantitative real-time PCR analysis provides on the order of $10^1$ to $10^2$ genes in the whole population. Bulk RNA sequencing can provide information on $10^3$ genes but there is no way to identify individual cell populations. However, single cell analysis does not come without its own caveats. The newness of single cell analysis means that the field is constantly improving the strategies to determine the in vivo identity of neuronal populations. Traditionally, a few known genes have determined neuronal identity and the field is only now beginning to assign transcriptome profiles to different neuronal subpopulations at various time points in development (Hayes, Kottick et al. 2017, Lake, Chen et al. 2018, Rosenberg, Roco et al. 2018). This can make identification of hPSC derived populations inherently difficult not only because the exact developmental timeline is unknown and likely heterogeneous, but also because it is a different species origin. Fortunately, recent publication of single cell data sets from respiratory regions at different developmental stages has been an important resource for the identification of our iPSC-derived populations (Hayes, Kottick et al. 2017).

The data presented here corresponds with a data set derived from the pre BötC of P0 mice (Hayes, Kottick et al. 2017). The study analyzed the transcriptional signature of cells that reside in the pre BötC and compared the cells that once expressed the V0 progenitor marker, Dbx1, and those that did not. In agreement with our data, the murine study identifies upregulation of Lhx5, Pax2, HoxA4, among others in the Dbx1$^+$ population. Additionally, Dbx1 transcript is not present in the P0 mice demonstrating that the marker turns off with maturation which supports why Dbx1 was not detected in the D17 cells. Further, PHOX2B is upregulated in the Dbx1$^-$ cells from the pre BötC region (Hayes, Kottick et al. 2017). This supports that PHOX2B expression is identified in a similar region yet separate from the V0 interneurons. Collectively, single cell transcriptomic analysis detected the presence of V0 interneurons and chemosensing neurons in the hPSC differentiated cultures.

In this study, three distinct populations were differentiated from one set of signaling molecules. The hindbrain originates as the neural tube and forms in response to a ventrodorsal gradient of Shh (Marklund, Alekseenko et al. 2014). This gradient specifies different interneuron subtypes wherein V2a interneurons lie ventral to V0 interneurons. The rostrocaudal identity is influenced by RA concentration. The RA gradient appears to peak at the base of rhombomere formation and decrease in the rostral direction toward the hindbrain (Glover, Renaud et al. 2006). In the data presented here, the relative proportions of interneurons can be modulated by Shh signaling. Lower concentrations of pur induce higher percentages of V0 interneurons and lower amounts of V2a interneurons. Conversely, a higher concentration of pur results in higher percentages of V2a interneurons over V0 interneurons. Additionally, lower concentrations of RA induce higher percentages of V2a and V0 interneurons potentially indicating that the lower concentration of RA is recapitulating developmental signaling and specifies the hindbrain region which in turn increases the amount of V2a and V0s. These data indicate that developmental pathways were being probed in vitro. The initial intent of the study was to find the right combination of signaling molecules that resulted in the highest CHX10 percentage to induce V2a interneurons. However, a defined combination of chemical signals and culture conditions has induced a regional identity that contains the V2a interneurons, more specifically the respiratory control centers in the hindbrain. Along with that has come induction of additional cell types (V0 interneurons and chemosensing neurons) that are developmentally located in a similar region and function together as a tissue.

By definition, a tissue is composed of multiple cell populations that function together to perform a task. To engineer a functioning tissue in vitro, it is necessary that multiple cell types interact and operate as a unit. Traditional tissue engineering approaches have been to derive individual cell populations that compose the tissue separately and then combine the defined cell populations together with a matrix or mold to form a tissue (Takebe, Sekine et al. 2013). However, because these cell population are derived or isolated separately, they may not mature at the same rate or contain proper support cell populations which therefore may not integrate to form the tissue-specific function. An alternate approach to in vitro tissue formation is co-emergence. Instead focusing on individual cell types separately, the concept of co-emergence is to differentiate multiple cell populations that arise from similar signaling mechanisms developmentally in one dish, which more accurately represents endogenous tissue formation (Sternfeld, Hinckley et al. 2017). In this study, a platform is demonstrated wherein multiple cell populations present in respiratory regions (Chemosensing, V2a and V0 interneurons) co-emerge from one developmentally relevant signaling environment. During development, differing neuronal populations arise from coordinated signaling events in combination with cell-cell signaling which is important to specification of neighboring cell types. Developmentally, V2a and V0 interneurons as well as the chemosensing population arise in the neural tube in response to Shh and RA signaling. The differentiation described here begins with a blank slate of PSCs that are first treated with dual SMAD inhibition to specify a neural progenitor state (Chambers, Fasano et al. 2009). Next, RA is added to promote a non-cortical phenotype and it is speculated that the concentration of RA used in this study is specifying a hindbrain/high cervical phenotype. Once the rostrocaudal identity is determined, Shh signaling drives the ventrodorsal identity (Dessaud, Ribes et al. 2010). At the stage where the Shh agonist is added to the in vitro culture, a multilayer cell sheet has formed therefore, it is possible that across the well, there are local regions of high and low Shh signaling that may specify different interneuron subtypes similar to the Shh gradient in vivo. This theory was supported by observing the change in relative proportions of interneurons in response to concentration of pur (FIG. 10). The mechanism of the chemosensing specification is still being investigated as developmentally, this population arises from the dorsal half of the neural tube in response to little Shh signaling (Sieber, Storm et al. 2007). However, the ability of these three populations to co-emerge in a dish and converge upon a combination of neurons that have a defined functional role in vivo seems to reflect that once the hPCSs have been pushed to a neural fate, the importance of cell-cell interactions are key in defining committed phenotypes.

Conclusion

Together, this work demonstrates how multiple neuronal populations that develop and function together in vivo can be differentiated from one set of signaling molecules in vitro from hPSCs. Single cell RNA-sequencing revealed the presence of multiple respiratory hindbrain populations in our cultures (FIG. 6) and these findings were further confirmed by protein expression analysis (FIG. 9). Additionally, the relative interneuron populations can be manipulated through changes in morphogen concentration demonstrating the ability to recapitulate the in vivo signaling environment in vitro (FIG. 10). After identifying that the cultures contain multiple neurons that have genetic signatures similar to those that arise developmentally in the hindbrain and are involved in respiration, this platform presents an opportunity to explore how in vivo signaling pathways have be probed in vitro. While the work described here focuses on development of a hindbrain phenotype, a similar concept could be applied when developing directed differentiation protocols for any lineage that results in co-emergence of multiple cell types.

REFERENCES

Alheid, G. F., P. A. Gray, M. C. Jiang, J. L. Feldman and D. R. McCrimmon (2002). "Parvalbumin in respiratory neurons of the ventrolateral medulla of the adult rat." *J Neurocytol* 31(8-9): 693-717.

Amir, R. E., I. B. Van den Veyver, M. Wan, C. Q. Tran, U. Francke and H. Y. Zoghbi (1999). "Rett syndrome is caused by mutations in X-linked MECP2, encoding methyl-CpG-binding protein 2." *Nat Genet* 23 (2): 185-188.

Azim, E., J. Jiang, B. Alstermark and T. M. Jessell (2014). "Skilled reaching relies on a V2a propriospinal internal copy circuit." *Nature* 508 (7496): 357-363.

Blanchi, B., L. M. Kelly, J. C. Viemari, I. Lafon, H. Burnet, M. Bevengut, S. Tillmanns, L. Daniel, T. Graf, G. Hilaire and M. H. Sieweke (2003). "MafB deficiency causes defective respiratory rhythmogenesis and fatal central apnea at birth." *Nat Neurosci* 6 (10): 1091-1100.

Bochorishvili, G., R. L. Stornetta, M. B. Coates and P. G. Guyenet (2012). "Pre-Botzinger complex receives glutamatergic innervation from galaninergic and other retrotrapezoid nucleus neurons." *J Comp Neurol* 520 (5): 1047-1061.

Bouvier, J., M. Thoby-Brisson, N. Renier, V. Dubreuil, J. Ericson, J. Champagnat, A. Pierani, A. Chedotal and G. Fortin (2010). "Hindbrain interneurons and axon guidance signaling critical for breathing." *Nat Neurosci* 13 (9): 1066-1074.

Burgold, T., N. Voituron, M. Caganova, P. P. Tripathi, C. Menuet, B. K. Tusi, F. Spreafico, M. Bevengut, C. Gestreau, S. Buontempo, A. Simeone, L. Kruidenier, G. Natoli, S. Casola, G. Hilaire and G. Testa (2012). "The H3K27 demethylase JMJD3 is required for maintenance of the embryonic respiratory neuronal network, neonatal breathing, and survival." *Cell Rep* 2 (5): 1244-1258.

Burridge, P. W., E. Matsa, P. Shukla, Z. C. Lin, J. M. Churko, A. D. Ebert, F. Lan, S. Diecke, B. Huber, N. M. Mordwinkin, J. R. Plews, O. J. Abilez, B. Cui, J. D. Gold and J. C. Wu (2014). "Chemically defined generation of human cardiomyocytes." *Nat Methods* 11 (8): 855-860.

Butts, J. C., D. A. McCreedy, J. A. Martinez-Vargas, F. N. Mendoza-Camacho, T. A. Hookway, C. A. Gifford, P. Taneja, L. Noble-Haeusslein and T. C. McDevitt (2017).

"Differentiation of V2a interneurons from human pluripotent stem cells." *Proc Natl Acad Sci USA* 114 (19): 4969-4974.

Chambers, S. M., C. A. Fasano, E. P. Papapetrou, M. Tomishima, M. Sadelain and L. Studer (2009). "Highly efficient neural conversion of human ES and iPS cells by dual inhibition of SMAD signaling." *Nat Biotechnol* 27 (3): 275-280.

Ciani, L. and P. C. Salinas (2005). "WNTs in the vertebrate nervous system: from patterning to neuronal connectivity." *Nat Rev Neurosci* 6 (5): 351-362.

Crone, S. A., K. A. Quinlan, L. Zagoraiou, S. Droho, C. E. Restrepo, L. Lundfald, T. Endo, J. Setlak, T. M. Jessell, O. Kiehn and K. Sharma (2008). "Genetic ablation of V2a ipsilateral interneurons disrupts left-right locomotor coordination in mammalian spinal cord." *Neuron* 60 (1): 70-83.

Crone, S. A., J. C. Viemari, S. Droho, A. Mrejeru, J. M. Ramirez and K. Sharma (2012). "Irregular Breathing in Mice following Genetic Ablation of V2a Neurons." *J Neurosci* 32(23): 7895-7906.

Dauger, S., A. Pattyn, F. Lofaso, C. Gaultier, C. Goridis, J. Gallego and J. F. Brunet (2003). "Phox2b controls the development of peripheral chemoreceptors and afferent visceral pathways." *Development* 130 (26): 6635-6642.

Example 2: Generation of Respiratory Hindbrain Organoids

Introduction

In Example 1, a monolayer culture system was described wherein multiple respiratory populations that typically arise in the hindbrain including V2a and V0 interneurons as well as a chemosensing population co-emerged. These populations work in tandem to control respiration in vivo. Monolayer cultures provide a platform to test culture conditions in a high-throughput manor, however, cell-cell interactions are limited. Therefore, we wanted to observe how these populations would organize and mature in a three-dimensional (3D) system where cell interactions are less constrained. The following study describes the formation of hindbrain organoids and evaluates the changes in morphology and cell-type specific markers during the induction and maturation processes. The organoids display synchronous activity as they mature similar to what has been reported from native respiratory structures. This study provides the first report of a hindbrain organoids system that contains cell populations critical to respiration.

3D cultures systems have been a common platform for neural stem cell differentiations since the onset of the field. The first directed motor neuron differentiation protocol began with spontaneous formation of the stem cells into clusters of cells called embryoid bodies (Wichterle, Lieberam et al. 2002). However, in recent years, 3D neural culture has expanded to include organoids wherein stem cells are directed to a neural fate as multiple cell types co-emerge with some organization that resembles aspects of the native tissue. While 3D culture models have been explored since the early 1990s (Barcellos-Hoff, Aggeler et al. 1989, Petersen, Ronnov-Jessen et al. 1992), one of the first reports of an organoid system recapitulated cerebral development (Lancaster, Renner et al. 2013). In the last 10 years, many different neural organoids have been described that recapitulate a variety of neural structures including the retina, forebrain, midbrain cerebellum, and hypothalamus (Eiraku, Watanabe et al. 2008, Wataya, Ando et al. 2008, Muguruma, Nishiyama et al. 2010, Kadoshima, Sakaguchi et al. 2013, Jo, Xiao et al. 2016). Ideally, more than just structural similarity, an organoid would have a greater ability to generate a tissue-specific function that is not possible in a two dimensional system. To date, an organoid system that resembles the hindbrain and provides a platform to probe respiratory control has not been described. This study expands the previously described 2D culture conditions to co-emerge multiple hindbrain respiratory populations and provides a 3D hindbrain-like organoid system to model the neural circuits that control respiratory rhythm generation.

Respiration is a controlled closed-loop system that broadly incorporates neurons, the muscles that control lung volume, and the partial pressure of $CO_2$ ($pCO_2$) in the blood stream. The main sensor in this circuit is the chemosensing neuron in the hindbrains that sense changes in $pCO_2$, which provide input onto pre-inspiratory and pre-expiratory neurons in the medulla (Goridis, Dubreuil et al. 2010, Ruffault, D'Autreaux et al. 2015). The pre-inspiratory and pre-expiratory neurons then transduce signals to the phrenic motor neurons that form a neuro-muscular junction with the diaphragm and intercostal muscles to control inspiration and expiration (Boulenguez, Gauthier et al. 2007). Oxygen exchange with the outside environment during inspiration and expiration alters $pCO_2$, which is then again sensed by the chemosensing population in the hindbrain, closing the respiration control circuit (Feldman, Mitchell et al. 2003, Guyenet, Stornetta et al. 2010). Researchers have worked to determine the phenotypic identity of the cells responsible for each of these critical circuit components.

The chemosensing neurons of the circuit are located in the retrotrapezoid nucleus/pre facial respiratory group (RTN/pFRG) (Mulkey, Stornetta et al. 2004, Stornetta, Moreira et al. 2006). This structure resides in the rostral aspect of the ventral respiratory group (VRG) in the ventrolateral medulla. The RTN is a nuclei of thousands of cells comprised of glutamatergic chemosensing neurons that express PHOX2B and detect $pCO_2$ in the bloodstream by a proton receptor (Wang, Shi et al. 2013). Together, the RTN/pFRG comprise the large majority of what have been called preinspiratory neurons in the respiratory rhythm generating circuit. The chemosensing neurons in the RTN are not rhythmic themselves but do form direct synapses with rhythmic inspiratory neurons located in the pre BötC (Mulkey, Stornetta et al. 2004, Guyenet, Mulkey et al. 2005).

The pre BötC is located caudal to the RTN in the VRG and is composed of a variety of cell types that are involved in respiratory rhythm generation as well as sighing behavior (Smith, Ellenberger et al. 1991). The cells of the pre BötC have been reported to be a combination of glutamatergic, glycinergic, and GABAergic neurons however, the excitatory signals are a necessary component for respiratory rhythm generation (Bouvier, Thoby-Brisson et al. 2010, Gray, Hayes et al. 2010). Consistent with their role in rhythm generation, neurons in the pre BötC produce a $Ca^{2+}$ flux that is synchronous and periodic (Koizumi, Koshiya et al. 2013). Recent studies implicate commissural V0 interneurons that arise from Dbx1+ progenitors to be a critical neuronal subtype responsible for the pacing behavior of the pre BötC by providing a synchronous oscillatory output to pre motor populations (Wu, Capelli et al. 2017).

Medullary V2a interneurons located in the medial reticular formation also provide excitatory input into the pre BötC. The V2a interneurons are located at the same rostrocaudal level but medial to the pre BötC in the medulla. Ablation of these cells results in an irregular breathing pattern (Crone, Viemari et al. 2012). Electrophysiological analysis combined with synaptic tracing revealed V2a interneurons form excitatory synapses with tonic input onto cells in the pre BötC. While the synaptic target of the V2a interneurons in the pre BötC was not identified, it was hypothesized that the V0 interneurons are a potential target due to the known interactions of V2a and V0 interneurons in spinal motor circuits (Crone, Viemari et al. 2012). Together, chemosensing neurons in the RTN/pFRG and V2a interneurons in the mRF provide excitatory drive to the V0 interneurons in the pre BötC, which then produce a rhythmic output to control respiration. Together, the chemosensing, V2a, and V0 interneurons form a specific balanced neural circuit that one disrupted connection could lead to dysfunction.

Congenital central hypoventilation syndrome (CCHS) is a disease caused by a polyalanine expansion in PHOX2B, which disrupts the function of chemosensing neurons (Amiel, Laudier et al. 2003, Trochet, Hong et al. 2005). The lack of $CO_2$ sensing causes individuals to take shallow breaths and results in a build-up of $CO_2$ and a lack of oxygen in the blood stream. Symptoms of CCHS are typically identified soon after birth and the current standard of care is a ventilator or a diaphragm pacemaker. While this disease is considered to be rare, it has been identified as a potential cause of Sudden Infant Death Syndrome (SIDS) (Weese-Mayer, Berry-Kravis et al. 2008). Additionally, symptoms of CCHS can arise later in life without genetic mutation but in response to injury. In this study, we use a cell line with a Y14X mutation in the PHOX2B loci that diminishes the chemosensing population in our cultures to model CCHS in organoid culture (Workman, Mahe et al. 2017)

The following study describes the first report of a hindbrain organoid composed of neurons that are involved in respiratory control. The neurodevelopment of and function of the hindbrain interneuron populations can now be studied by assessing the differentiation, maturation, and function of these organoids. Additionally, as the organoids mature, they can be used as a model to assess how changes in respiratory circuit composition in response to injury or disease alters the functional output.

Materials and Methods

Human Pluripotent Stem Cell Culture

Human PSCs—WTC and WTB iPSCs (generously donated by Bruce Conklin)—were grown to 70% confluence and passaged using ACCUTASE™ (cell detachment solution) (ACCUTASE™, San Diego, CA) to dissociate to single cells (incubated at 37° C. for 5 minutes). Dissociated cells were replated on MATRIGEL™ (a gelatinous extracellular matrix (ECM) mixture coated cultureware (hESC-qualified for ESCs and growth factor reduced for iPSCs) at a density of 10,000 cells per cm² with 10 µM ROCK inhibitor (Y-27632, Selleckchem, Houston, TX) in mTeSR (StemCell Technologies, Vancouver, Canada). All work with human ESC and iPSC lines have been approved by the University of California—San Francisco Human Gamete, Embryo and Stem Cell Research (GESCR) Committee.

V2a Interneuron Differentiation in 3D Organoid Culture

Human PSCs were seeded at 125 k cells/cm² in mTeSR supplemented with 10 µM ROCK inhibitor and 2 µM CHIR99102. For WNT treated cells, CHIR was supplemented into the media at each feed through day 7. 48 hours later, cell layers were dissociated using Accutase and counted. For organoid culture, 800 µm pyramidal PDMS inserts were placed into 24-well plates. 1 ml mTeSR containing 10 µM ROCK inhibitor was added to the wells containing the molds and the plate was centrifuged at 2,000×g for 3 minutes to get rid of any bubbles. Dissociated cells, either hPSCs or WNT pre-treated cells, were then added slowly into the wells at 10,000 cells per organoid in mTeSR supplemented with 10 µM ROCK inhibitor, 0.2 LDN193189, and 10 µM SB431542 (StemGent, Cambridge, MA). Twenty-four hours later, the organoids condensed to spheres and were washed out by gentle trituration with a p1000 pipette into a conical. After the organoids had settled, the spent media was aspirated and resuspended in mTeSR containing 10 µM ROCK inhibitor, 0.2 LDN193189, and 10 µM SB431542 and placed into 1 well of a 6-well plate. To change the media on the cells for the rest of the differentiation, the organoids were pipetted into a conical and allowed to settle. Old media was aspirated off and new media was used to resuspend the organoids and transfer them back to the 6 well. On day 3, medium was changed to mTeSR supplemented with dual SMAD inhibitors only. On day 5, the base medium was switched to neural induction medium (DMEM F: 12 (Corning, Corning, NY), N2 supplement (Life Technologies, Carlsbad, CA), L-Glutamine (VWR), 2 µg/ml heparin (Sigma Aldrich, St. Louis, MO), non-essential amino acids (Mediatech INC, Manassas, VA), penicillin-streptomycin (VWR) supplemented with fresh 0.4 µg/ml ascorbic acid (Sigma Aldrich) and 10 ng/ml brain derived neurotrophin factor (BDNF, R&D Systems, Minneapolis, MN)) supplemented with dual SMAD inhibitors and 10 nM-10 µM retinoic acid (Sigma Aldrich). On day 7, dual SMAD inhibition was ceased and 10 nM-10 µM retinoic acid, 10 nM-10 µM pur (EMD Millipore, Darmstast, Germany) and 1 µM N—[N-(3,5-difluorophenacetyl)-L-alanyl]-S-phenylglycine t-butyl ester (DAPT) were added to the neural induction medium. Medium was changed every 2 days throughout the differentiation, with fresh supplements added each time for up to 17 to 19 days.

Dissociation of V2a Interneuron Organoid Cultures

To dissociate organoid cultures, samples were collected and washed with 1 mL of PBS. The organoids were then transferred to 1 well of a 6-well plate with 2 ml of accutase and incubated on the rotary at 37° C. for 15 minutes. The organoids were triturated approximately 10 times every 15 minutes with a p1000 to break up cell clusters until the cells were completely dissociated—typically 45 minutes to 1 hour. The dissociated cells were then transpired to a 15 mL conical and diluted with 3 times the volume of PBS.

Neuronal Maturation

On day 17 of differentiation, organoids were switched to neural maturation medium (BRAINPHYS™ (neurophysiological basal medium) plus SM1 supplement (Stemcell Technologies (Bardy, van den Hurk et al. 2016)) supplemented with 10 ng/ml of BDNF, GDNF, CNTF, and IGF, R&D Systems). Medium was completely changed every 5 days for the remainder of the culture duration.

Flow Cytometry

At day 17 of differentiation, cells were completely dissociated using Accutase and stained with the Transcription Factor Buffer Set, which includes a fixation/permeabilization (FP) and wash/permeabilization (WP) buffer (BD Biosciences, Franklin Lakes, NJ). Dissociated samples were first fixed for 45 minutes at 4° C. in the FP buffer followed by a 20-minute block with WP buffer containing 5% normal donkey serum (NDS, Jackson Laboratory, Bay Harbor, ME). Primary antibodies against CHX10, LHX5, PHOX2A, and PHOX2B (Table 3) and the proper matching species isotype control were added into WP buffer containing 2% NDS and incubated at 4° C. for 45 minutes. After two washes with WP buffer, secondary antibodies donkey anti-mouse IgG, ALEXA FLUOR™ 488 (a fluorescent compound; Life Technologies), at a dilution of 1:200, were added to WP buffer and incubated at 4° C. for 45 minutes. After two washes with WP buffer, samples were passed through a 35-μm filter before assessing with a BD ACCURI™ C6 (BD) cytometer (minimum 10,000 events). Cytometry analysis was performed using FlowJo V10 (Flowjo, Ashland, OR).

Organoid Tissue Processing

Organoids were first fixed with 4% paraformaldehyde for 1 hour at room temperature while rotating on a rotisserie. The paraformaldehyde was removed, and the organoids were resuspended in PBS and stored at 4° C. until embedding was performed. For embedding, the tissues were resuspended in 300 μl HISTOGEL™ (specimen processing gel; Thermo Scientific), dispensed into a tissue mold and solidified at 4° C. for 1 hour. The HISTOGEL™ (specimen processing gel) molds containing the organoids were then dispensed into tissue processing cassettes and processed into paraffin blocks. Tissue blocks were sectioned into 5 μm sections, placed onto microscope slides and incubated at 37° C. overnight before antigen retrieval and staining.

Histological Processing and Immunostaining of Organoid Tissue Sections

Slides containing the paraffin sections were deparaffinized prior to staining using a series of xylene and alcohol washes. Slides were then washed 3 times in PBS for 5 minutes at room temperature. For antigen retrieval, slides were incubated in antigen unmasking solution (Vector Laboratories) at 95° C. for 35 minutes and cooled for 25 minutes at room temperature. Slides were washed 3 times in PBS for 5 minutes at room temperature. The individual sections were then outlined using a wax pen. The samples were permeabilized briefly with 0.2% triton for 5 minutes at room temperature. Following 3 washes for 5 minutes, the samples were blocked in PBS containing 5% NDS. Primary antibodies were added to PBS containing 2% NDS at a dilution listed in Table 3 and incubated on the samples overnight at 4° C. Following three 15 minutes washes, secondary antibodies were added at a dilution of 1:200 in PBS containing 2% NDS and incubated at room temperature for 1 hour. Following a 10-minute incubation of Hoechst in PBS, slides were washed 3 times in PBS for 5 minutes. The slides were mounted with PROLONG™ Gold (hard setting liquid mountant; Life Technologies) and cover glass. For long-term storage, the cover glass was secured with nail polish and kept in 4° C.

For hematoxylin and eosin (H&E) staining, a standard protocol was followed. Briefly, slides were deparaffinized and re-hydrated followed by 5 minutes of Gill's Hematoxylin (Newcomersupply) and a series of washes. Slides were then counterstained in Eosin-Y (Newcomersupply) for 1 minute followed by a series of alcohol then zylene washes. Slides were then coversliped with CYTOSEAL™ (mounting medium; Richard-Allen Scientific). Florescent slides were imaged using a Zeiss Axio Observer inverted widefield microscope equipped with an Apotome structured light attachment. An average intensity projection was performed on Z-stack images to create a single two-dimensional image spanning the entire thickness of the observed field. H&E slides were imaged using the Zeiss Axio Imager upright microscope. Images were processed using Zen Blue and Photoshop.

Immunocytochemistry and Imaging of Whole Mount Organoids

Whole mount organoids were fixed using 4% paraformaldehyde (VWR) for 1 hour at room temperature. For all steps of the staining process, samples were rotating on a rotisserie. The samples were then permeabilized using 0.1% TRITON® X (a non-ionic surfactant) in PBS for 15 minutes at 4° C. before blocking for 1 hour at 4° C. with PBS containing 0.1% bovine serum albumin (BSA) and 5% NDS. Primary antibodies (Table 3) were diluted in PBS containing 0.1% BSA and 2% NDS then incubated overnight. Samples were washed three times with PBS for 15 minutes at room temperature before incubating with secondary antibodies (Life Technologies) diluted in PBS containing 0.1% BSA and 2% NDS. Hoechst was added to the samples for 10 minutes then washed. Organoids were imaged with a Zeiss LSM880 Confocal. Intensity levels were uniformly adjusted using Zen Blue.

Phase Imaging Quantification

Phase contrast images of the organoids were taken using the EVOS® FL Imaging System. The size analysis performed in FIG. 12 was performed manually using Image J. The size analysis performed in FIG. 13 was done using a Python script to first segment the organoids using a watershed segmentation algorithm. The long and short axis was then extracted from the segmented image and plotted using Prism 7 software.

TABLE 3

Antibodies used for flow cytometry and immunostaining

| Antibody Target | Species | Vendor | Cat. Number | Application | Dilution |
|---|---|---|---|---|---|
| βIII Tubulin | rabbit | Covance | PRB-435P-100 | ICC | 1 to 1000 |
| CHX10 | mouse | Santa Cruz | sc-374151 | Flow and ICC | 1 to 1000 |
| E-Cadherin | mouse | Abcam | AB1416 | ICC | 1 to 400 |
| EVX1/2 | mouse | DHSB | 99.1-3A2 | ICC | 1 to 100 |
| GABA | rabbit | Sigma-Aldrich | A2052 | ICC | 1 to 1000 |
| Glial Fibrillary Acidic Protein (GFAP) | chicken | Aves Labs | GFAP | ICC | 1 to 1000 |
| GXB2 | rabbit | Proteintech | 21639-1-AP | ICC | 1 to 50 |
| Ki67 | rabbit | Abcam | AB15580 | ICC | 1 to 500 |
| LHX5 | goat | R&D | AF6290 | Flow and ICC | 1 to 250 |
| Myelin Basic Protein (MBP) | chicken | Thermo Fisher | PA1-10008 | ICC | 1 to 1000 |
| N-Cadherin | rabbit | Abcam | AB76057 | ICC | 1 to 50 |
| NESTIN | mouse | Santa Cruz | sc-23927 | ICC | 1 to 100 |
| NeuN | chicken | Millipore (EMD) | abN91 | ICC | 1 to 200 |
| NeuN | rabbit | Millipore (EMD) | ABN91 | ICC | 1 to 200 |
| OCT4 | goat | Santa Cruz | sc-8629 | ICC | 1 to 400 |
| OLIG2 | rabbit | Millipore (EMD) | AB9610 | ICC | 1 to 500 |
| PAX6 | mouse | Santa Cruz | sc-81352 | ICC | 1 to 200 |
| PH3 | mouse | Cell Signaling | 33775 | ICC | 1 to 500 |
| PHOX2A | mouse | Santa Cruz | 81978 | Flow and ICC | 1 to 250 |
| PHOX2B | mouse | Santa Cruz | 376997 | Flow | 1 to 500 |
| PHOX2B | goat | R&D | AF4940 | ICC | 1 to 250 |
| SOX2 | mouse | Abcam | AB79352 | ICC | 1 to 200 |
| Synaptophysin | rabbit | Synaptic Systems | 101 002 | ICC | 1 to 200 |

TABLE 3-continued

| Antibodies used for flow cytometry and immunostaining | | | | | |
|---|---|---|---|---|---|
| Antibody Target | Species | Vendor | Cat. Number | Application | Dilution |
| Tau | mouse | BioLegend | 835201 | ICC | 1 to 250 |
| VGLUT2 | rabbit | Synaptic Systems | 135 403 | ICC | 1 to 500 |
| ZO1 | mouse | Life Technologies | 359100 | ICC | 1 to 400 |

Calcium Imaging and Analysis

Endogenous GCaMP6 signal was used to detect calcium flux in differentiations performed with the WTC GCaMP6 cell line. Alternatively, cultures of cells that lacked GCaMP expression were washed with PBS and the medium was replaced with NEUROBASAL™ (neural cell culture medium) plus Fluo4 AM (5 μM, Life Technologies) for 1 hour at 37° C. The cultures were then washed with fresh Neurobasal and allowed to recover for an additional 1-hour minutes at 37° C. before recording on a Zeiss Axio Observer. To assess $Ca^{2+}$ fluctuations, cultures were imaged at a rate of 17 frames per second. To analyze the results, ROI were selected by hand using Zen software. For organoids, the outer edge of the tissue was selected and for monolayer cultures, individual neurons were selected. The relative fluorescent units (RFU) measured at the ROIs were processed using Python3. A detrend function with a robust linear regression was performed for normalization and a 4 Hz lowpass Butterworth filter was applied to minimize noise.

Statistical Analysis

Statistical analysis was performed using Prism 6 software. The mean and +standard deviation were calculated for a minimum of three biological replicates for all data unless otherwise noted. One-way analysis of variance (ANOVA) followed by appropriate post hoc pairwise comparisons Tukey's tests were used when three or more groups were specified. Specific statistical analysis is mentioned within the corresponding figure legend. Variances were confirmed to not differ significantly with the Brown-Forsythe test.

Results

3D Differentiation of Hindbrain Respiratory Populations

Figure 12C:
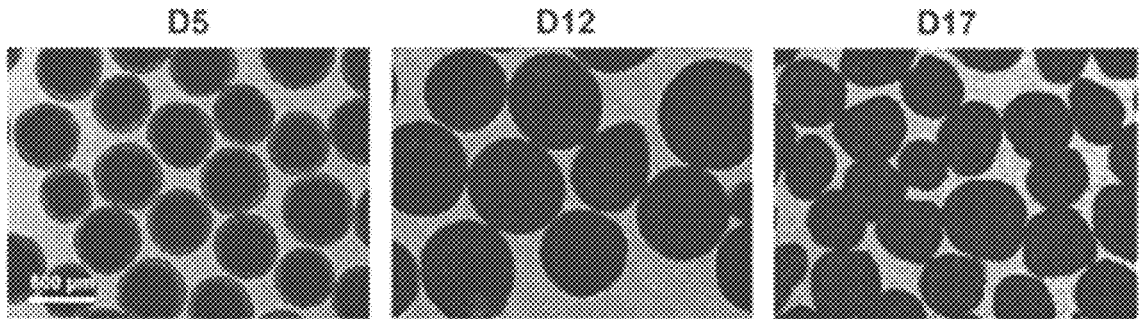
Figure 12D:
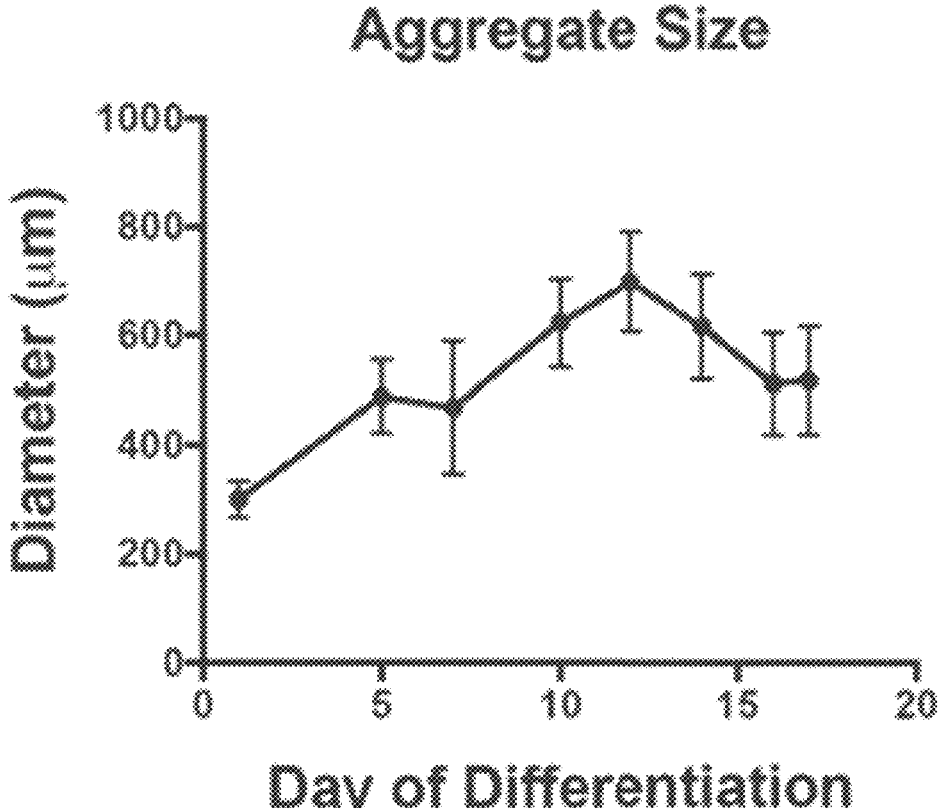

V2a interneurons, V0 interneurons, and chemosensing neurons are each important to respiratory control and were induced using a hindbrain differentiation in monolayer. In 2D culture systems, however, cell-cell interactions are limited as the cells are constrained to the surface of the plate. Here, a 3D differentiation platform is described to observe the self-organization and function of the hindbrain interneuron populations with culture duration. The hindbrain differentiation was performed in 3D to determine if the respiratory populations could be induced in suspension culture. For 3D organoid culture, hiPSCs were first pre-treated with CHIR99021 for two days in monolayer prior to aggregation. The cell layers were dissociated and plated into pyramidal molds overnight to create consistent organoids in a high throughput manner (FIG. 12A) The newly formed organoids were then transferred to a 10 cm dish and cultured for the remainder of the differentiation in suspension (FIG. 12B). Visual inspection of phase imaging throughout the differentiation revealed the organoids were largest around day 12 and remain circular until later time points (FIG. 12C). Quantification of the phase images confirmed the organoids began approximately 300 μm in diameter and grew to a peak diameter of approximately 700 μm at day 12 (FIG. 12D). The organoid diameter began to decrease on day 14 and levels off at a diameter of approximately 500 μm at day 17

Figure 12E:
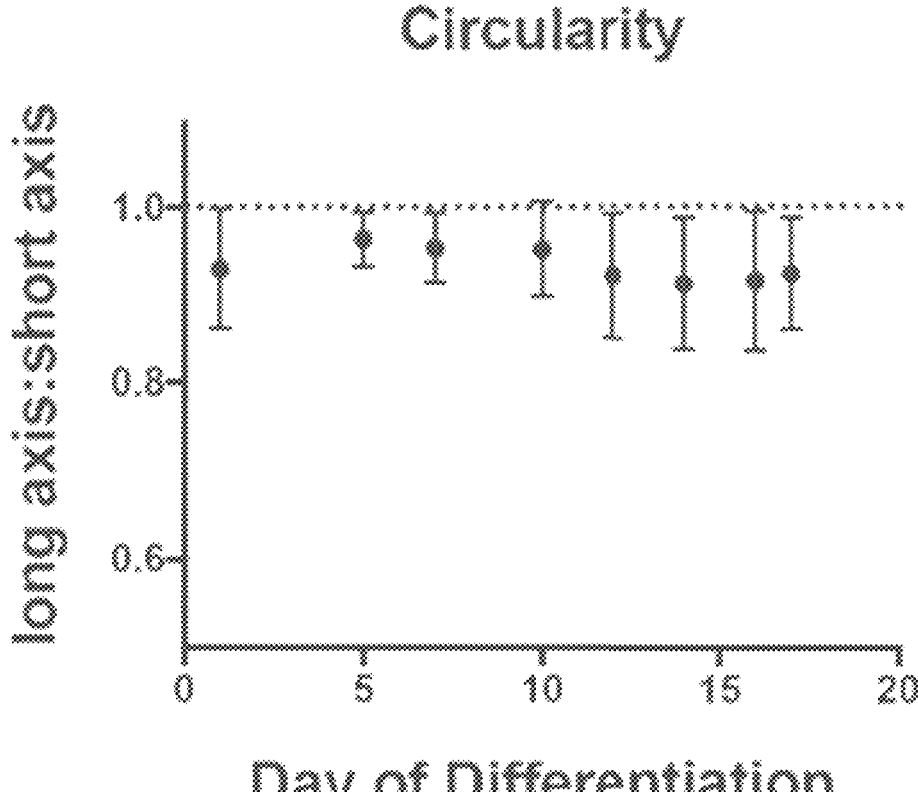

(FIG. 12D). The organoids also became less circular at later time points of the differentiation, which may reflect morphogenic changes are occurring (FIG. 12E).

Figure 12F:
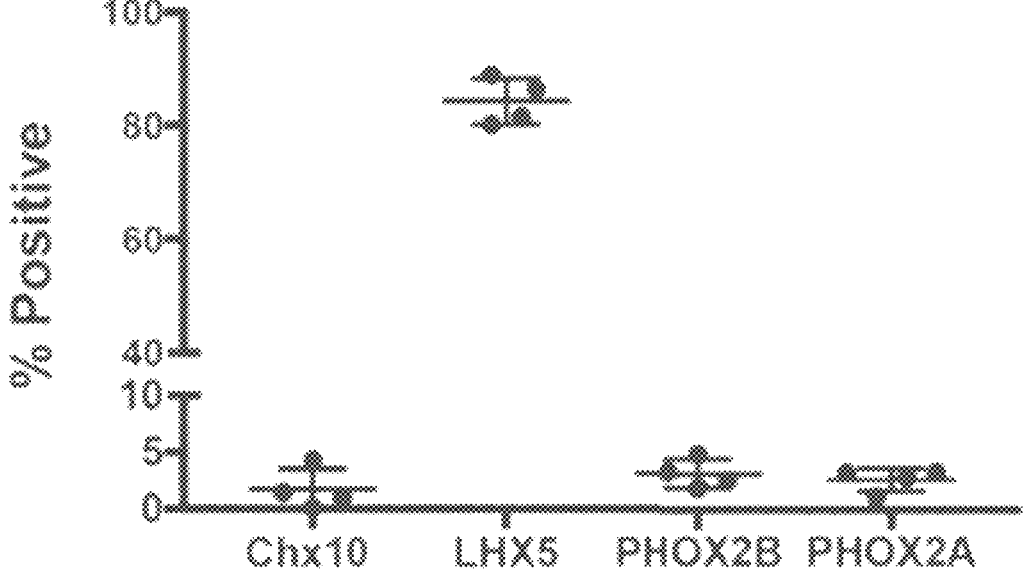
Figure 12G:
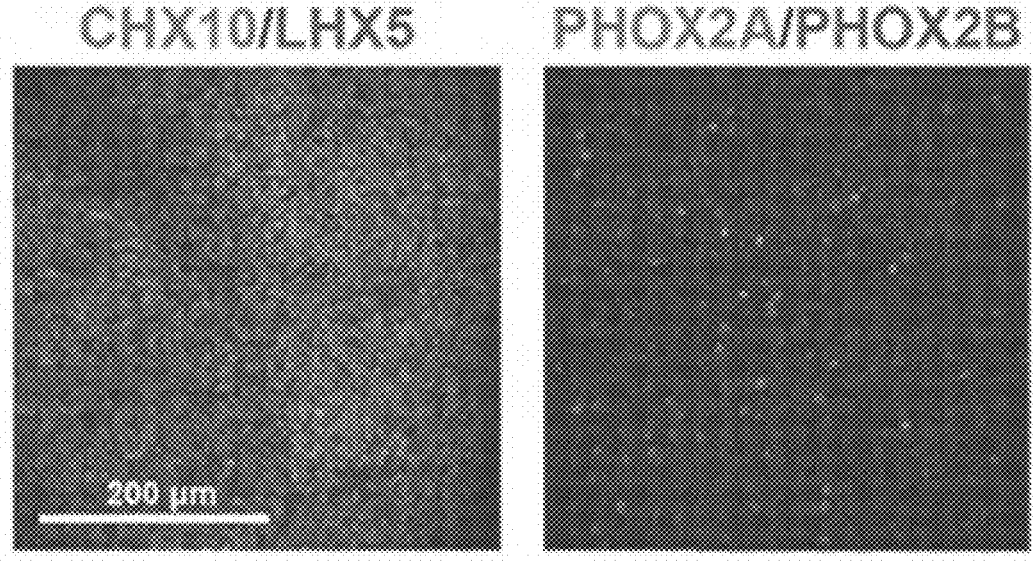

Using the same concentrations of pur (100 nM) and RA (100 nM) that were defined as optimal concentrations for V2a interneurons in monolayer differentiations, the 3D culture system resulted in small percentages of CHX10$^+$, PHOX2A$^+$, and PHOX2B$^+$ cells (<5%) but high concentrations of LHX5$^+$ cells (~80%, FIG. 12F). The cytometry results were visually confirmed through whole mount immunostaining of the organoids (FIG. 12G). Not surprisingly, it appeared the effective concentration of the small molecules was different in monolayer vs. organoid cultures possibly due to different diffusion rates. Therefore, it was postulated that to define a more balanced population of the three cell types, different concentrations of signaling molecules might be needed in 3D compared to 2D.

Modulation of V2a and V0 Interneurons in Response to Sonic Hedgehog Signaling

Figure 13A:
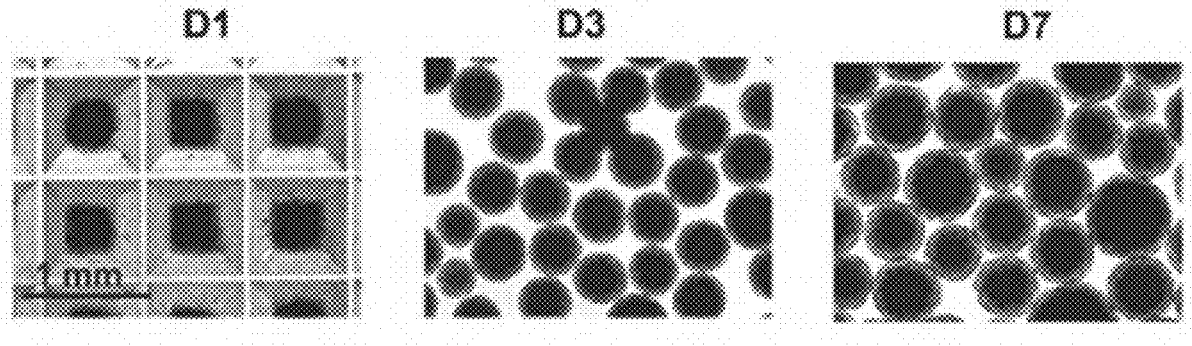
FIGS. 13A-13D show cellular composition of the organoids is modulated by pur concentration.
Figure 13B:
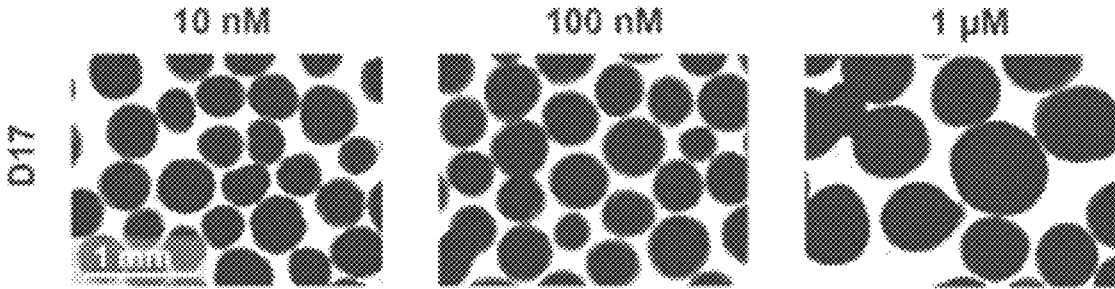
Figure 13C:
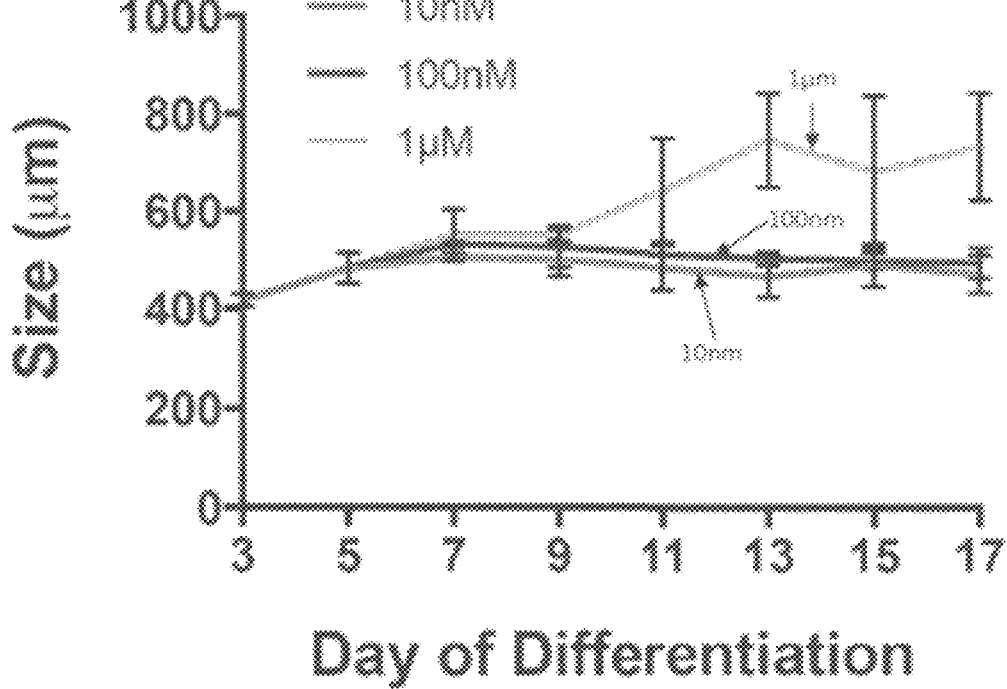
Figure 13D:
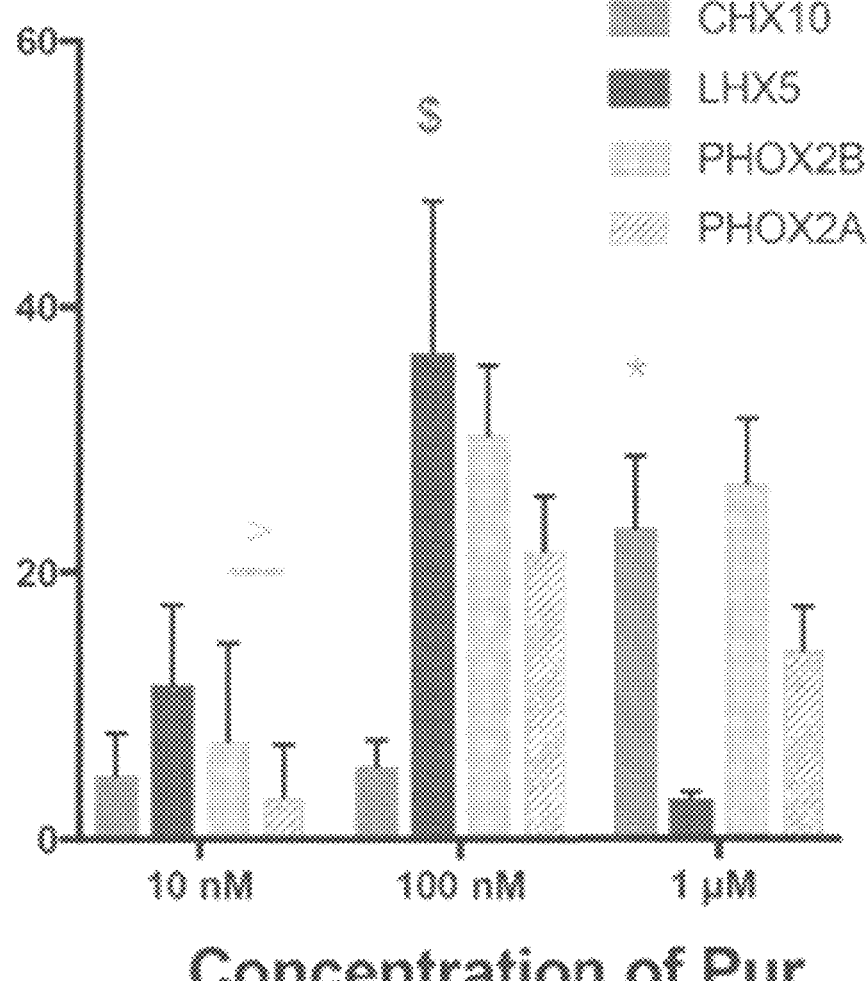

Previous monolayer studies demonstrated that changing Shh signaling modulated relative proportions of V2a and V0 interneurons similar to the way progenitor domains develop in response to ventral-to dorsal Shh gradient. Therefore, it was postulated that the cellular composition of the organoids could be modulated similarly. The differentiation was performed using 10 nM, 100 nM, or 1 u M pur. The organoids were homogenous and round at early stages of the differentiation (day 1 to day 7, FIG. 13A). However, by the end of the differentiation, the 10 nM and 100 nM pur groups were smaller than the 1 μM pur group indicating the pur concentration is having some effect on organoid morphogenesis potentially through limiting proliferation (FIG. 13B). In this study, the size analysis of the organoids was performed using a segmentation algorithm as a more unbiased approach than analysis by hand. Throughout the differentiation, the 10 nM and 100 nM pur groups maintained a relatively constant diameter (~500 μm), but the 1 μM pur group grew in size beginning on day 9 and was approximately 700 μm by day 17 (FIG. 13C). To assess how pur concentration influenced cell fate determination, the relative proportions of V2a interneurons, V0 interneurons, and chemosensing neurons were analyzed on day 17 via flow cytometry (FIG. 13D). Using 10 nM pur, low percentages of all subtypes were observed (V0$^{low}$V2a$^{low}$) suggesting the low amount of shh signaling was inefficient at driving neuronal commitment. 100 nM pur resulted in high percentages of LHX5 (36.5%) and low percentages of CHX10 (3.5%, V0$^{high}$V2a$^{low}$), consistent with previous organoid experiments. 1 μM pur resulted in low percentages of LHX5 (3.1%) and high percentages of CHX10 (23.3%, V0$^{low}$V2a$^{high}$). PHOX2A and PHOX2B percentages were highest in the 100 nM and 1 μM pur condition. This experiment demonstrates how relative proportions of the V2a and V0 interneurons can be modulated in response to Shh signaling, thus providing control over the population in order to probe how each of the interneurons affect the respiratory circuit.

Developmental Timeline of Organoid Culture

Self-organization is an important aspect of organoid culture. Therefore, we were interested in how these cell types emerge given a 3D environment. A longitudinal study was performed to assess how the V2a, V0 and chemosensing populations develop in the organoids, The analyzed organoids were treated with 1 μM pur.

Figure 14A:
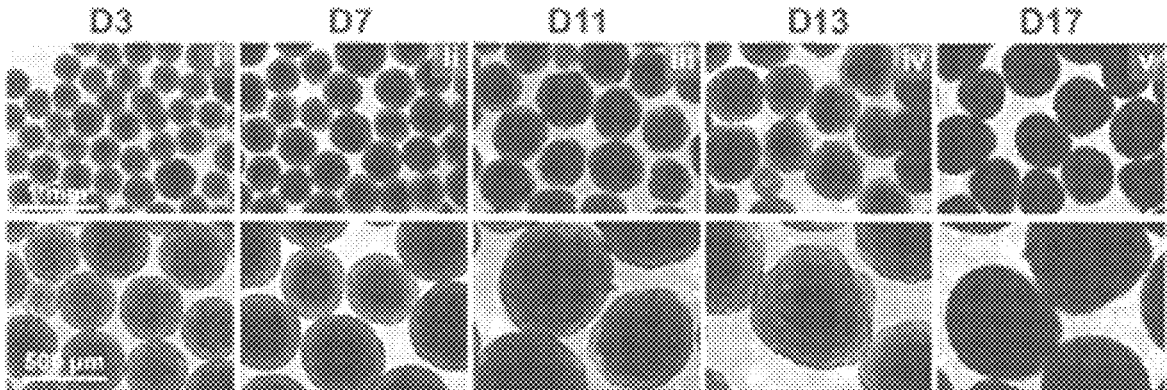
FIGS. 14A-14B show phase contrast and H&E of organoids throughout the differentiation.
Figure 14B:
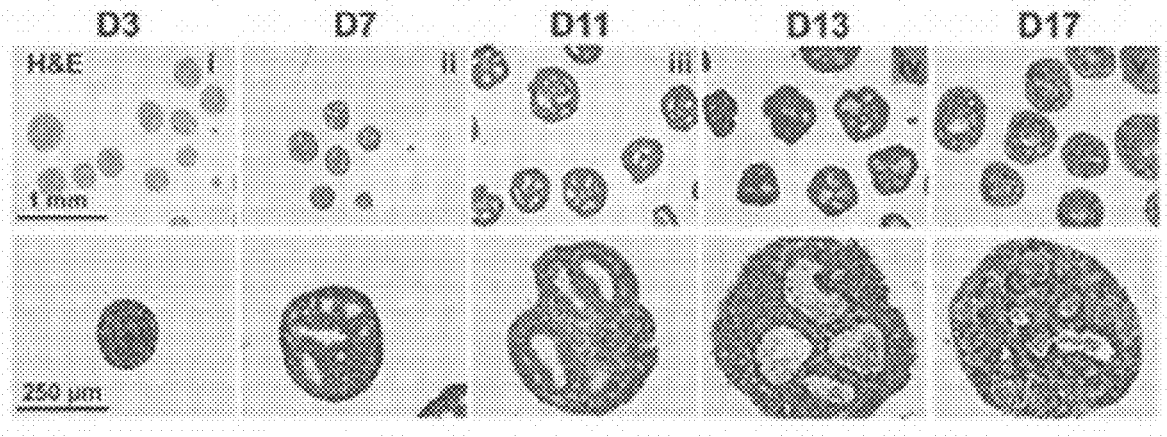

The organoids appeared to grow throughout the hindbrain differentiation process as visualized through phase imaging. Gross morphological changes in organoids where observed including a transition from smooth to irregular boundaries and a transient swirling pattern created by cell organization (FIG. 14A). During neural tube formation, the neuroepithelium elongates and compacts around the central canal then proliferates and differentiates to become the progenitor domains of the neural tube. In in vitro cell culture, a circular organization of condensed and proliferating progenitor cells that resembles early neural tube formation is identified as a neural rosette (Wilson and Stice 2006). H&E was performed to observe these morphological changes in tissue sections. Small lumens formed in the organoids by day 3 of the differentiation (FIG. 14 Bi). By day 7, rosette-like structures were beginning to form as the lumens began to enlarge and nuclei around the lumen became more radially aligned (FIG. 14Bii). More developed rosette structures were apparent by day 11 as indicated by elongated nuclei arranged around the lumens (FIG. 14Biii). Additionally, the perimeter of the organoids became less smooth consistent with the phase images (FIG. 14Aiii). The rosette structures were still visible by day 13 but the regions adjacent to the lumens appear to become more filled with nuclei (FIG. 14Biv). By day 17, the organoids became rounder and the luminal spaces surrounded by rosettes became smaller (FIG. 14Bv). The H&E analysis demonstrated additional morphological changes, including the formation of rosette structures, thus expanding on observations obtained via phase imaging and revealing recapitulation of some aspects of neural development.

Figure 15A:
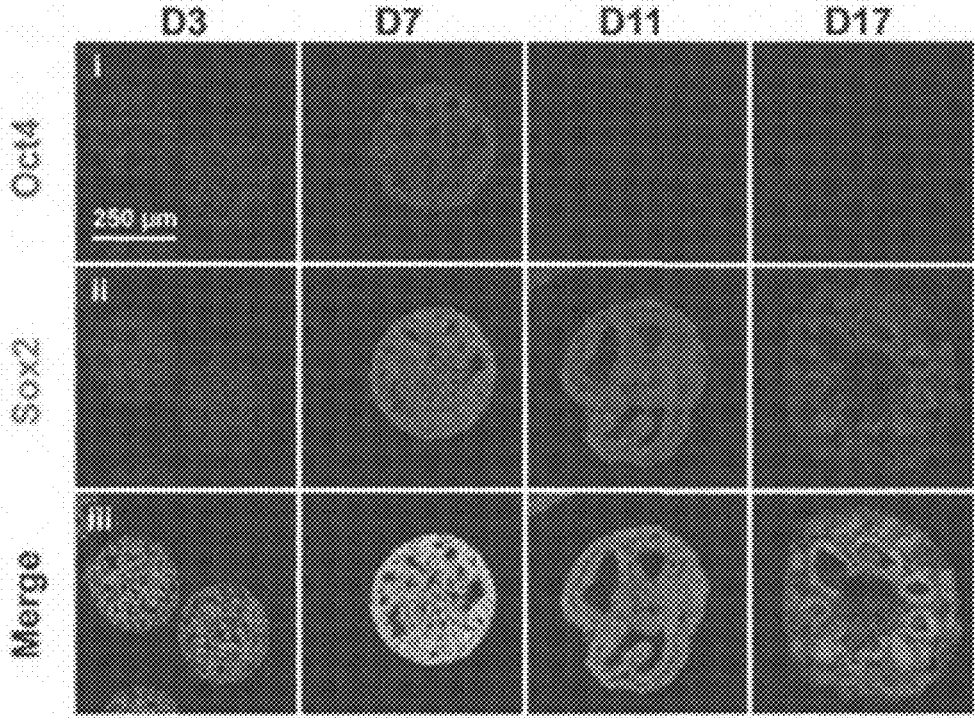
FIG. 15A-15B show analysis of pluripotency and proliferation in organoid sections throughout differentiation.
Figure 15B:
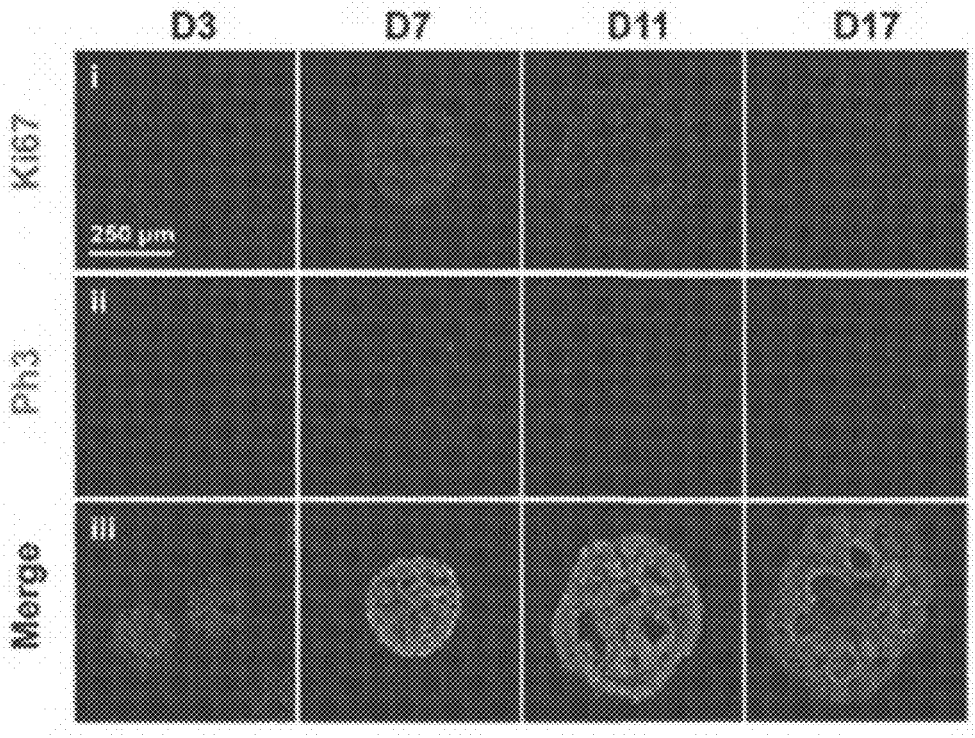

The H&E results revealed structures that resembled neural rosettes, therefore additional analysis was performed to examine if the correct markers were expressed as the organoids developed. First, the expression of pluripotency and proliferation markers was assessed throughout the neural induction process. OCT4, a marker of pluripotency, was present in the organoids at day 3 and through day 7 but was absent by day 11 indicating the hPSCs were differentiating to a committed lineage (FIG. 15Ai). SOX2, a marker of pluripotency and early ectoderm was present and colocalized with OCT4 at day 3 and 7 (FIG. 15Aiii). By day 11, SOX2 expression persisted contrary to decreases in OCT4 confirming the emergence of a neuralectoderm phenotype. At day 17, SOX2 expression was present predominantly in the rosette-like structures indicating the many of the cells in these areas were still neural progenitors (FIG. 15Aii). Neural progenitors are a dividing cell population; therefore, the presence of proliferating cells was explored using Ki67. Most of the cells in the organoid were proliferating at day 3 but Ki67 expression began to diminish by day 11 (FIG. 15Bi). A small number of proliferating cells were present at day 17 but were localized to the rosette-like structures similar to SOX2 expression (FIG. 15Bi). Actively dividing cells, detected by phospho-histone H3 (PH3), were colocalized with Ki67 throughout the induction process but at lower frequency because the time a cell spends dividing is only a fraction of the cell cycle. By day 17 they were localized the rosette structures along with the Ki67 expression (FIG. 15Bii-iii). Together, at early time points, cells throughout the organoid are rapidly dividing but as cells begin to differentiate into committed lineages, the proliferation is more concentrated to the rosette structures.

To detect when different stages of neural commitment were occurring, the presence of early neural markers (Nestin and Bin Tubulin) as well as the transition from E-Cadherin expression to N-Cadherin expression was assessed. While Nestin and Bin Tubulin are early neural markers, Nestin is expressed by neural progenitors while BILI Tubulin continues to be expressed in committed, yet immature, neurons. Nestin and Bull Tubulin expression was robust by day 11 indicating a neural progenitor phenotype and continued throughout the duration of the culture period (FIG. 16Aiii). While Nestin and $\beta_{III}$ Tubulin colocalized at day 11, by day 17, Nestin expression appeared to be more highly expressed within the rosette structures while $\beta_{III}$ Tubulin was more diffuse throughout the organoid (FIG. 16Aiii). This change in expression pattern further confirmed the progenitor phenotype of the rosettes but also provided evidence that the cells outside of the neural rosettes were maturing to committed neurons. (FIG. 16Ai-ii). This fate transition was also demonstrated through a change in Cadherin expression. As cells differentiate down the neural lineage, there is a switch in Cadherin expression from E-Cadherin in pluripotent cells to N-Cadherin as cells commit to a neural fate (Hatta and Takeichi 1986, Detrick, Dickey et al. 1990). E-Cadherin outlined individual cells day 3 organoids but by day 7 became more colocalized to the luminal structures and turned off by day 11 (FIG. 16Bi). Little N-Cadherin expression was observed on day 7 but by day 11 it was located at the luminal structures and on the edges of the organoids (FIG. 16Bii). By Day 17, N-Cadherin was expressed more robustly and was observed throughout the organoids with a greater intensity of staining around the lumens (FIG. 16Bii). This data supports emergence of an early neural progenitor by day 7 that continues to mature throughout the induction.

Two additional hallmarks of neural tube and neural rosette formation are the colocalization of ZO-1 with N-Cadherin at the apical surface of the lumen indicated of boundary formation and the presence of the neural progenitor marker, PAX6 (Aaku-Saraste, Hellwig et al. 1996). Diffuse expression of ZO-1, a tight junction marker, was present at the edges of the lumen at day 3 but condensed to form a tight luminal border by day 17. (FIG. 17Ai). ZO-1 expression colocalized with N-Cadherin on days 11 and 17 similar to what has been identified during neural tube formation (FIG. 17Aiii). PAX6, an early neural transcription factor was present at day 3 throughout the aggregates and began to turn off by day 11. At later time points, PAX6 was colocalized to the rosette structures (FIG. 17Bi). Bull Tubulin expression was highest at day 17 and could be identified around the PAX6+ cells (FIG. 17Bii). The combination of nuclear organization with the expression of tight-junction, Cadherin, and neural progenitor markers reveals the presence of neural rosettes reminiscent of native neural tube development in the differentiating organoids.

As the neural tube develops, neural progenitor domains expand near the central canal then migrate to more lateral positions in the spinal cord as the neurons mature into committed phenotypes. To determine the timing of how the respiratory populations (V2a, V0, and chemosensing) emerge in the organoid, the expression of more subtype-specific markers were examined. GBX2, a marker expressed in the developing hindbrain was identified at day 11 with expression localized mainly to the rosette regions. From day 13 to day 17, GBX2 expression diminishes and becomes more diffuse throughout the organoid (FIG. 18Ai). CHX10, marking the committed V2a population, was greatest at day 15 and appeared to be localized away from the rosette structures (FIG. 18Aii). CHX10 appeared to co-localize with GBX2 but not all GBX2+ cells were CHX10+ (FIG. 18Aiii). This result suggests that CHX10+ cells have a hindbrain lineage and implies that GBX2 expression precedes the emergence of more committed hindbrain phenotypes within the organoid. LHX5, a marker of V0 interneurons, was expressed in the organoids at day 15 and was localized to the rosette structures (FIG. 18Bi). EVX1/2, a marker of committed V0 interneurons was robustly expressed by day 17 and was observed throughout the organoid (FIG. 18 Bii). Further, LHX5 appeared to colocalize with EVX1/2 but not all EVX1/2" cells were LHX5⁺, which might suggest LHX5 expression precedes EVX1/2 expression (FIG. 18Biii). PHOX2B, a marker for chemosensory neurons, was expressed at low levels at day 13 but increased by day 15 and continued through day 17. PHOX2A expression emerged later than PHOX2B at day 15 and also continued through day 17. Both PHOX2A and PHOX2B expression appeared to be located in the outer region of the organoid on day 15 and 17. The longitudinal examination of the induction process revealed the organoids undergo a differentiation program similar to what occurs in the developing neural tube from early neural commitment to maturation into post-mitotic neurons of the respiratory hindbrain region.

Phenotypic Analysis of Maturing of Organoid Cultures

To observe how the organoids mature, samples described in FIG. 12 were switched to BrainPhys medium supplemented with growth factors at D17. Via phase imaging, the organoids continued to grow and become more spherical after 17 days of culture before appearing to plateau in growth day 40 (FIG. 19A). A sample of organoids were taken every 10 days and processed for histological sectioning to assess maturation. H&E staining revealed a change in nuclear density as the organoids matured. The D17 organoids were very nuclear dense but the nuclei become more diffuse as the cultures matured. The sparse nuclei with increased extracellular space is more similar to native neural tissue which is less nuclear dense. Additionally, the size of the nuclei increased with culture duration indicative of maturation (FIG. 19B). Interestingly, the lumens that form during the induction process were no longer observed.

Expression of a variety of mature markers were analyzed throughout the culture duration. Expression of Bin Tubulin, a marker of immature filaments, was highest at day 30 and appeared to decrease by day 50 (FIG. 20A). Tau, a marker of mature filaments, had low level of expression at day 17, but the expression became more robust by day 50 (FIG. 20B). This indicates that the immature filaments are being replaced by more mature axonal proteins with culture duration. Expression of NeuN, a marker of mature neurons, was present at low levels from day 17 to day 40 but expression was heavily distributed throughout the organoid by day 50 (FIG. 20C). Vesicular glutamate transporter 2 (VGLUT2), a marker of glutamatergic neurons, and synaptophysin, a pre-synaptic marker, were both expressed at day 40 and became brighter and more abundant at day 50 (FIGS. 20D and 20E), indicating the organoids expressed markers needed to be functional. Lastly, a few cells expressed glial fibrillary acidic protein (GFAP), indicative of astrocytes, by day 50 (FIG. 20F). While the main focus has been on neurons, the presence of glial phenotypes is key to a recapitulating native tissue, which contains both neuronal and glial phenotypes.

At 100 days of culture, the organoids had smooth edges with more cell-dense regions visible towards the center (FIG. 21A). H&E staining revealed nuclei are present throughout the organoids and a swirling pattern of nuclei appeared to have formed in some of the organoids (FIG. 21B). Analysis of mature neuronal markers was performed to observe how the organoids had matured by 100 days. Similar to D50 samples, the organoids contained NeuN⁺ cells. However, at D100, there were many more GFAP⁺ cells that appeared to intermingle with Tau⁺ axons localized to the NeuN regions (FIG. 21C). GABA expression, marking inhibitory populations was present but interestingly largely localized to NeuN-regions (FIG. 21D). The organoids con-tained high abundance of the excitatory marker, VGlut2, a phenotype of the chemosensing population and the V2a and V0 interneurons (FIG. 21E). There also continued to be high abundance of synaptophysin indicating synapses are being formed (FIG. 21F). Not surprisingly, CHX10 was not present in the D100 culture but there was evidence of OLIG2, marking the presence of oligodendrocyte precursors (FIG. 21G). Staining for myelin basic protein (MBP) was minimal indicating that more time may be necessary for myelination to occur or there are too few OLIG2⁺ cells (FIG. 21G). Together, the immunostaining results show that the organoids are inducing a mature neuronal phenotype that is primarily glutamatergic with a small GABAergic population. Additionally, the presence of glia, including GFAP⁺ astrocytes and progenitor oligodendrocytes, were potentially providing functional support to the neurons.

Functional Analysis of Maturing of Organoid Cultures

The maturation of the organoids was next assessed by measuring $Ca^{2+}$ flux. The study was performed using the WTC11 GCaMP iPS cell line, which allowed for easy assessment of calcium flux every 5 to 6 days of the maturation process. At early time points (D17 to D38), little calcium flux was observed in individual organoids. However, at D42, whole organoids began to fire synchronously with a periodic rate (FIG. 22A). From that point onward, the organoids were imaged as a field of samples instead of as individual organoids. At day 52, all organoids were active but had different periodicities (FIG. 22B). The synchronous activity did stop after 3-5 minutes of the cultures being out of the incubator, suggesting potential sensitivity to ambient air and temperature (FIG. 22Bii). By day 69, the frequency of $Ca^{2+}$ activity was more variable between organoids and by day 92, $Ca^{2-}$ fluctuations were less common and less periodic. These changes in functional readout may be driven by changes in glial populations or increased synaptic connection, which correlate with the immunostaining results where few glial and synaptic populations are identified by day 50 but increase by day 100.

To observe if the cellular composition of the organoids was important to the periodic synchronous activity, $Ca^{2+}$ flux was measured in the organoids differentiated with varying concentrations of pur. A functional comparison was made between the three samples that had different composition of interneurons: $V0^{low}V2a^{low}$ (10 nM pur), $V0^{high}V2a^{low}$ (100 nM pur), and $V0^{low}V2a^{high}$ 1 µM pur). Calcium fluctuations were initially observed at day 33 and imaged every 5 to 6 days thereafter (FIG. 23). The $V0^{low}V2a^{low}$ group had few periodic synchronous events throughout the measured time period (FIG. 23A). Both the $V0^{high}V2a^{low}$ and $V0^{low}V2a^{high}$ group displayed periodic synchronous $Ca^{2+}$ fluctuations, though the $V0^{high}V2a^{low}$ group was more rhythmic overall and the $V0^{low}V2a^{high}$ appeared more sporadic (FIGS. 23B and 23C). These results suggest the cellular composition does impact the functional response in that the interneurons are needed for the rhythmic activity and that more V0 interneurons increase the rhythmicity. This study probes the influence of the interneuron populations but not the PHOX2A/PHOX2B population, as it was not changed in response to Shh signaling, which is an important piece of the neural circuit.

Model of CCHS in Organoid Culture

Figure 24E:
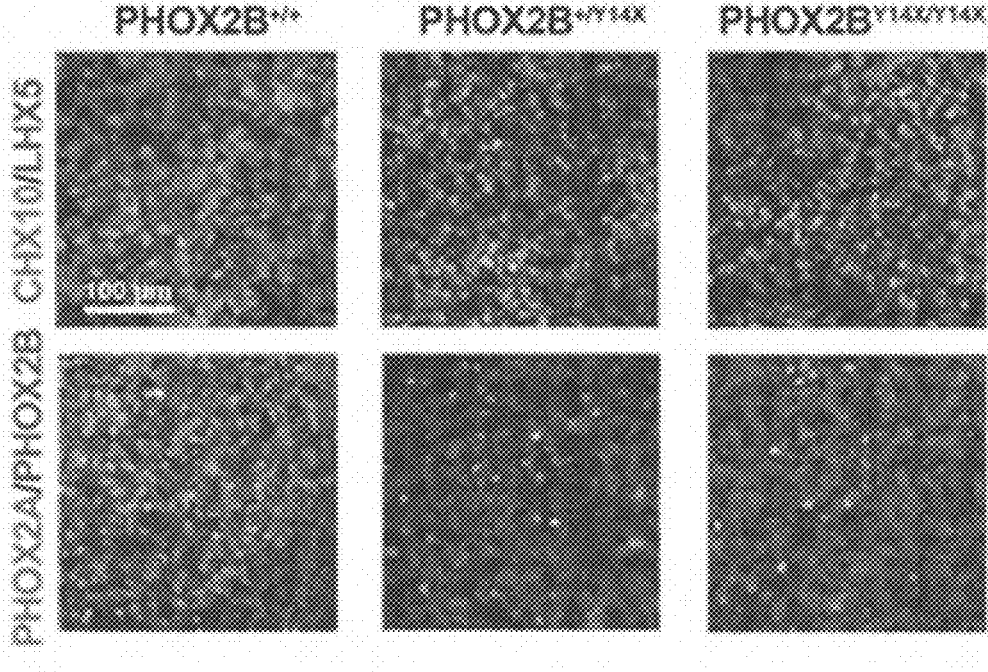

CCHS is a disease caused by a PHOX2B mutation that results in the loss of $CO_2$ sensing and thus loss of respiratory control. The hindbrain differentiation was performed in organoid and monolayer culture simultaneously using a heterozygous and homozygous PHOX2B mutant hiPSC cell line (PHOX2B$^{+/Y14X}$ and PHOX2B$^{Y14X/Y14X}$) along with the isogenic control line (PHOX2B$^{+/+}$) (Workman, Mahe et al. 2017). All cell lines formed organoids normally and there were no discernable differences between the WT and mutant organoids via phase microscopy (FIG. 23A). On day 17 of organoid and monolayer culture, PHOX2B was detected in the PHOX2B$^{+/+}$ line (~20%) but was diminished in the PHOX2B$^{+/Y14X}$ and PHOX2B$^{Y14X/Y14X}$ lines (~5%) (FIGS. 23B and 23C). Consequently, expression of PHOX2A was also diminished in the PHOX2B$^{+/Y14X}$ and PHOX2B$^{Y14X/Y14X}$ lines (~2%) compared to the PHOX2B$^{+/+}$ line (~15%). However, the effect of the mutation on V2a and V0 interneuron cultures differed in the organoid and monolayer cultures. In organoid culture, CHX10% was higher in the mutant lines (~45%) compared to the PHOX2B$^{+/+}$ line (~15%) but LHX5% was highest in the PHOX2B$^{+/+}$ (~35%) line compared to mutant lines (~15%). In monolayer culture, a different result was observed where LHX5% was highest in the mutant lines (~45%) compared to the PHOX2B$^{+/+}$ line (~20%). Similar percentages of CHX10 were detected across all lines in monolayer cultures. These relative percentages in organoid and monolayer culture were confirmed through immunostaining (FIGS. 24E and 24F). This data suggests that the inhibition of PHOX2B does not adversely affect the differentiation of V2a and V0 interneurons and actually increased the differentiation efficiency of V2a interneurons in organoid culture and V0 interneurons in monolayer culture potentially because the PHOX cells are no longer competing for signaling giving more opportunity for V2a and V0 development.

To assess how the organoid and monolayer cultures matured, the samples were switched to BrainPhys supplemented with growth factors. At day 38, both samples were treated with the Ca$^{2+}$ dye, Fluo4, to observe if the mutant cell lines were capable of producing the periodic synchronous fluctuations. All organoid groups displayed some periodic synchronous activity with the fluctuations being more prevalent in the PHOX2B$^{+/Y14X}$ and PHOX2B$^{Y14X/Y14X}$ organoids (FIG. 25A). Interestingly, all monolayer cultures had active neurons as displayed through calcium flux but they appeared to not be synchronous (FIG. 25B). Together, these data suggest the PHOX2B population is not responsible for the synchronous activity and that the 3D structure is critical to synchronization.

DISCUSSION

This study describes a platform to differentiate respiratory hindbrain organoids from hPSCs. When transitioning from a monolayer to a 3D platform, the need for higher concentrations of signaling molecules to permeate the organoids was considered. The first organoid differentiation was performed with the same concentration of molecules as the monolayer system, which was optimized for V2a interneurons. Using the same concentration of pur as the monolayer differentiation (100 nM), the percentage of V0 interneurons was high while percentage of CHX10 and PHOX2A/2B was very low (FIG. 12F). The ventrodorsal Shh gradient in the developing neural tube is organized such that the dorsal V0 interneurons receive lower amounts of signaling compared to the more ventral V2a interneurons. It was then hypothesized that a higher concentration of pur would result in an increased percentage of V2a interneurons in the organoids. This was confirmed through testing different concentrations of pur wherein a higher concentration (1 μM) resulted in a higher V2a population at the expense of the V0 population (FIG. 13D). The implication of these results was two-fold. First, the relative proportions of interneurons could be controlled through developmentally inspired mechanisms and second, the small molecule kinetics may be slower in a ~102 μm thick organoid compared to a ~10$^1$ μm thick monolayer culture.

Histological sectioning of the organoids through time revealed distinct organizations that recapitulated neural development. Most interestingly, was the formation of neural rosette-like structures with open lumens observed through H&E (FIG. 14B). While the definition of neural rosettes comes from a phenomenon observed during hPSC in vitro culture, they are believed to model neuroepithelium forming the neural tube in vivo (Wilson and Stice 2006). Expression of a variety of markers was used to further confirm the presence of neural rosettes. Developmentally, cells of the neural tube initially express E-Cadherin but as the neural tube forms, E-Cadherin expression stops and N-Cadherin expression begins (Hatta and Takeichi 1986, Detrick, Dickey et al. 1990). Similar transition of E-cadherin to N-Cadherin expression was observed in the organoids from days 3-7 (FIG. 15B). Next, condensation of N-Cadherin and the tight junction marker ZO-1 was observed at the luminal boarder in the organoids (FIG. 16A) similar to the condensation of these markers at the apical surface of neural tube formation (Aaku-Saraste, Hellwig et al. 1996) Additionally, the elongated nuclei comprising the rosettes in the center of the organoid were positive for neuroepithelial transcription factors SOX2 and PAX6, two defining populations of the early neural tube (Zhang, Huang et al. 2010) (FIG. 15A and FIG. 17B). Cells that make up the early neural tube are actively proliferating as the spinal cord develops. Similarly, proliferating cells are observed mainly in the rosette structures at later time points (FIG. 15B). Additionally, the hindbrain progenitor marker, GBX2, emerged closer to the rosette structures but the markers of committed neurons (CHX10, EVX1, PHOX2A, PHOX2B) are dispersed more throughout the organoid, away from the rosettes (FIGS. 18A-18C). LHX5 expression also appears to be closer to the rosettes potentially indicating that LHX5 expression is potentially an early marker for V0 interneurons before EVX1/2 expression begins.

The 3D differentiation recapitulates cell organization and temporal expression of neural development markers similar to that of the developing neural tube. The densely-packed elongated nuclear structures that are apparent after sectioning of the organoids have been observed in our monolayer cultures before however, a lumen never appeared. This could result from the cells being constrained to the 2D surface whereas the 3D differentiation platform provides the necessary 3D cell-cell interactions to form a lumen. One consideration when interpreting the results is that the histological analysis was performed only on organoids that were treated with 1 μM pur. We have demonstrated that different proportions of V2a, V0, and chemosensing neurons are induced in response to pur concentration; therefore, future studies are needed to compare how cellular organization changes in response to pur concentration.

As the organoids culture for up to 100 days, they express markers of maturation. While NeuN is visible at D17, the expression increases throughout culture (FIGS. 20C and 21C). The high abundance of VGLUT2 confirms the glutamatergic phenotypes of V2a and V0 interneurons as well as the chemosensing population (FIG. 21E). The initial focus of the differentiation had been on neuronal phenotypes; however, functional neural tissues contain glial phenotypes that are critical for tissue function. There is early evidence of GFAP$^+$ cells at D50 but by 100 days of culture, there is a large population indicative of a potential astrocytic population (FIGS. 20F and 21C). Recently, astrocytes have been implicated as an important cell population in the Pre BötC in which astrocytic vesicle release influences the rate of respiration (Sheikhbahaei, Turovsky et al. 2018). The high population of GFAP$^+$ cells may be recapitulating the predominance of astrocytes in the Pre BötC, which are a necessary part of the respiratory circuitry. Additionally, the cultures contain OLIG2$^+$ cells, which have the potential to mature into myelinating oligodendrocytes (FIG. 21F). The organoid cultures described here not only have a combination of neurons important for respiratory control but also have the glial phenotypes needed for a functional tissue.

At around 40 days of culture, the organoids began to exhibit synchronous, periodic Ca$^{2+}$ activity that is measurable and visible throughout the entire tissue (FIG. 22). The synchrony was visible in organoid cultures but not in comparable monolayer cultures (FIG. 25B) indicating the importance of the 3D platform. However, it was not clear which population in the organoid was driving this activity. From literature, it is known the chemosensing population changes synaptic output in response to pCO$_2$ but the activity of PHOX2B$^+$ neurons are not rhythmogenic (Mulkey, Stornetta et al. 2004, Guyenet, Mulkey et al. 2005). The V2a and V0 interneurons, which are a part of the respiratory circuit that we have differentiated, have been described to have rhythmic activity (Crone, Viemari et al. 2012, Wu, Capelli et al. 2017). Explanted slice culture of the murine pre BötC, which contains V0 interneurons, retain the ability generate respiratory rhythms autonomously (Smith, Ellenberger et al. 1991, Feldman, Mitchell et al. 2003) Additionally, Ca$^{2+}$ flux recordings of neurons in the rat pre BötC show similar periodicity that are observed in the organoid culture (Koizumi, Koshiya et al. 2013). The data shown in FIG. 22 that displayed periodic synchronous activity was collected from organoids with a high population of V0 interneurons. Further, the more rhythmogenic activity was observed by the V0$^{high}$V2a$^{low}$ cultures compared to the V0$^{low}$V2a$^{low}$ and V0$^{low}$V2a$^{high}$ cultures overtime (FIG. 23). Lastly, the synchronous activity was still detectable when the chemosensing population was absent using the PHOX2B$^{Y14X/Y14X}$ and PHOX2B$^{Y14X/Y14X}$ cell lines (FIG. 23). All of this data suggests that the synchronous activity in the organoids may be a measure of the V0 interneuron activity. However, further experimentation in an environment that controls for temperature and CO2 as the organoids mature will aid in elucidating the role of each population in the organoid.

CONCLUSION

This study describes the first report of a hindbrain organoid that is composed of V2a interneurons, V0 interneurons, and a chemosensing population of neurons important in the control of respiration. Analysis of the induction process revealed the organoid develops through a process similar to native neural tube development. Control over the cellular composition of the organoid was demonstrated through changing the pur concentration. The organoids matured to contain neurons that were primarily glutamatergic with an astrocyte support population consistent with the cellular composition of the pre BötC. Lastly, the organoids displayed synchronous Ca$^{2+}$ activity that is reminiscent of the native functioning pre BötC. This organoid platform could provide the first insight into human respiratory development and function. In the future, these organoids could potentially be used to track neural connectivity, assess how disease phenotypes affect respiratory output, and test new drug therapies during respiratory distress.

REFERENCES

Aaku-Saraste, E., A. Hellwig and W. B. Huttner (1996). "Loss of occludin and functional tight junctions, but not ZO-1, during neural tube closure—remodeling of the neuroepithelium prior to neurogenesis." Dev Biol 180(2): 664-679.

Amiel, J., B. Laudier, T. Attie-Bitach, H. Trang, L. de Pontual, B. Gener, D. Trochet, H. Etchevers, P. Ray, M. Simonneau, M. Vekemans, A. Munnich, C. Gaultier and S. Lyonnet (2003). "Polyalanine expansion and frameshift mutations of the paired-like homeobox gene PHOX2B in congenital central hypoventilation syndrome." Nat Genet 33 (4): 459-461.

Barcellos-Hoff, M. H., J. Aggeler, T. G. Ram and M. J. Bissell (1989). "Functional differentiation and alveolar morphogenesis of primary mammary cultures on reconstituted basement membrane." Development 105 (2): 223-235.

Bardy, C., M. van den Hurk, B. Kakaradov, J. A. Erwin, B. N. Jaeger, R. V. Hernandez, T. Eames, A. A. Paucar, M. Gorris, C. Marchand, R. Jappelli, J. Barron, A. K. Bryant, M. Kellogg, R. S. Lasken, B. P. Rutten, H. W. Steinbusch, G. W. Yeo and F. H. Gage (2016). "Predicting the functional states of human iPSC-derived neurons with single-cell RNA-seq and electrophysiology." Mol Psychiatry 21 (11): 1573-1588.

Boulenguez, P., P. Gauthier and A. Kastner (2007). "Respiratory neuron subpopulations and pathways potentially involved in the reactivation of phrenic motoneurons after C2 hemisection." Brain Res 1148:96-104.

Bouvier, J., M. Thoby-Brisson, N. Renier, V. Dubreuil, J. Ericson, J. Champagnat, A. Pierani, A. Chedotal and G. Fortin (2010). "Hindbrain interneurons and axon guidance signaling critical for breathing." Nat Neurosci 13 (9): 1066-1074.

Crone, S. A., J. C. Viemari, S. Droho, A. Mrejeru, J. M. Ramirez and K. Sharma (2012). "Irregular Breathing in Mice following Genetic Ablation of V2a Neurons." J Neurosci 32 (23): 7895-7906.

Detrick, R. J., D. Dickey and C. R. Kintner (1990). "The effects of N-cadherin misexpression on morphogenesis in *Xenopus* embryos." Neuron 4 (4): 493-506.

Eiraku, M., K. Watanabe, M. Matsuo-Takasaki, M. Kawada, S. Yonemura, M. Matsumura, T. Wataya, A. Nishiyama, K. Muguruma and Y. Sasai (2008). "Self-organized formation of polarized cortical tissues from ESCs and its active manipulation by extrinsic signals." Cell Stem Cell 3(5): 519-532.

Feldman, J. L., G. S. Mitchell and E. E. Nattie (2003). "Breathing: rhythmicity, plasticity, chemosensitivity." Annu Rev Neurosci 26:239-266.

Goridis, C., V. Dubreuil, M. Thoby-Brisson, G. Fortin and J. F. Brunet (2010). "Phox2b, congenital central hypoventilation syndrome and the control of respiration." Semin Cell Dev Biol 21(8): 814-822.

Gray, P. A., J. A. Hayes, G. Y. Ling, I. Llona, S. Tupal, M. C. Picardo, S. E. Ross, T. Hirata, J. G. Corbin, J. Eugenin and C. A. Del Negro (2010). "Developmental origin of preBotzinger complex respiratory neurons." J Neurosci 30(44): 14883-14895.

Guyenet, P. G., D. K. Mulkey, R. L. Stornetta and D. A. Bayliss (2005). "Regulation of ventral surface chemoreceptors by the central respiratory pattern generator." J Neurosci 25(39): 8938-8947.

Guyenet, P. G., R. L. Stornetta and D. A. Bayliss (2010). "Central respiratory chemoreception." J Comp Neurol 518(19): 3883-3906.

Hatta, K. and M. Takeichi (1986). "Expression of N-cadherin adhesion molecules associated with early morphogenetic events in chick development." Nature 320(6061): 447-449.

Jo, J., Y. Xiao, A. X. Sun, E. Cukuroglu, H. D. Tran, J. Goke, Z. Y. Tan, T. Y. Saw, C. P. Tan, H. Lokman, Y. Lee, D. Kim, H. S. Ko, S. O. Kim, J. H. Park, N. J. Cho, T. M. Hyde, J. E. Kleinman, J. H. Shin, D. R. Weinberger, E. K. Tan, H. S. Je and H. H. Ng (2016). "Midbrain-like Organoids from Human Pluripotent Stem Cells Contain Functional Dopaminergic and Neuromelanin-Producing Neurons." Cell Stem Cell 19(2): 248-257.

Kadoshima, T., H. Sakaguchi, T. Nakano, M. Soen, S. Ando, M. Eiraku and Y. Sasai (2013). "Self-organization of axial polarity, inside-out layer pattern, and species-specific progenitor dynamics in human ES cell-derived neocortex." Proc Natl Acad Sci USA 110(50): 20284-20289.

Koizumi, H., N. Koshiya, J. X. Chia, F. Cao, J. Nugent, R. Zhang and J. C. Smith (2013). "Structural-functional properties of identified excitatory and inhibitory interneurons within pre-Botzinger complex respiratory microcircuits." J Neurosci 33(7): 2994-3009.

Lancaster, M. A., M. Renner, C. A. Martin, D. Wenzel, L. S. Bicknell, M. E. Hurles, T. Homfray, J. M. Penninger, A. P. Jackson and J. A. Knoblich (2013). "Cerebral organoids model human brain development and microcephaly." Nature 501(7467): 373-379.

Muguruma, K., A. Nishiyama, Y. Ono, H. Miyawaki, E. Mizuhara, S. Hori, A. Kakizuka, K. Obata, Y. Yanagawa, T. Hirano and Y. Sasai (2010). "Ontogeny-recapitulating generation and tissue integration of ES cell-derived Purkinje cells." Nat Neurosci 13(10): 1171-1180.

Mulkey, D. K., R. L. Stornetta, M. C. Weston, J. R. Simmons, A. Parker, D. A. Bayliss and P. G. Guyenet (2004). "Respiratory control by ventral surface chemoreceptor neurons in rats." Nat Neurosci 7(12): 1360-1369.

Petersen, O. W., L. Ronnov-Jessen, A. R. Howlett and M. J. Bissell (1992). "Interaction with basement membrane serves to rapidly distinguish growth and differentiation pattern of normal and malignant human breast epithelial cells." Proc Natl Acad Sci USA 89(19): 9064-9068.

Ruffault, P. L., F. D'Autreaux, J. A. Hayes, M. Nomaksteinsky, S. Autran, T. Fujiyama, M. Hoshino, M. Hagglund, O. Kiehn, J. F. Brunet, G. Fortin and C. Goridis (2015). "The retrotrapezoid nucleus neurons expressing Atoh1 and Phox2b are essential for the respiratory response to CO(2)." Elife 4.

Sheikhbahaei, S., E. A. Turovsky, P. S. Hosford, A. Hadjihambi, S. M. Theparambil, B. Liu, N. Marina, A. G. Teschemacher, S. Kasparov, J. C. Smith and A. V. Gourine (2018). "Astrocytes modulate brainstem respiratory rhythm-generating circuits and determine exercise capacity." Nat Commun 9(1): 370.

Smith, J. C., H. H. Ellenberger, K. Ballanyi, D. W. Richter and J. L. Feldman (1991). "Pre-Botzinger complex: a brainstem region that may generate respiratory rhythm in mammals." Science 254(5032): 726-729.

Stornetta, R. L., T. S. Moreira, A. C. Takakura, B. J. Kang, D. A. Chang, G. H. West, J. F. Brunet, D. K. Mulkey, D. A. Bayliss and P. G. Guyenet (2006). "Expression of Phox2b by brainstem neurons involved in chemosensory integration in the adult rat." J Neurosci 26(40): 10305-10314.

Trochet, D., S. J. Hong, J. K. Lim, J. F. Brunet, A. Munnich, K. S. Kim, S. Lyonnet, C. Goridis and J. Amiel (2005). "Molecular consequences of PHOX2B missense, frameshift and alanine expansion mutations leading to autonomic dysfunction." Hum Mol Genet 14(23): 3697-3708.

Wang, S., Y. Shi, S. Shu, P. G. Guyenet and D. A. Bayliss (2013). "Phox2b-expressing retrotrapezoid neurons are intrinsically responsive to H+ and CO2." J Neurosci 33(18): 7756-7761.

Wataya, T., S. Ando, K. Muguruma, H. Ikeda, K. Watanabe, M. Eiraku, M. Kawada, J. Takahashi, N. Hashimoto and Y. Sasai (2008). "Minimization of exogenous signals in ES cell culture induces rostral hypothalamic differentiation." Proc Natl Acad Sci USA 105(33): 11796-11801.

Weese-Mayer, D. E., E. M. Berry-Kravis, I. Ceccherini and C. M. Rand (2008). "Congenital central hypoventilation syndrome (CCHS) and sudden infant death syndrome (SIDS): kindred disorders of autonomic regulation." Respir Physiol Neurobiol 164(1-2): 38-48.

Wichterle, H., I. Lieberam, J. A. Porter and T. M. Jessell (2002). "Directed differentiation of embryonic stem cells into motor neurons." Cell 110(3): 385-397.

Wilson, P. G. and S. S. Stice (2006). "Development and differentiation of neural rosettes derived from human embryonic stem cells." Stem Cell Rev 2(1): 67-77.

Workman, M. J., M. M. Mahe, S. Trisno, H. M. Poling, C. L. Watson, N. Sundaram, C. F. Chang, J. Schiesser, P. Aubert, E. G. Stanley, A. G. Elefanty, Y. Miyaoka, M. A. Mandegar, B. R. Conklin, M. Neunlist, S. A. Brugmann, M. A. Helmrath and J. M. Wells (2017). "Engineered human pluripotent-stem-cell-derived intestinal tissues with a functional enteric nervous system." Nat Med 23 (1): 49-59.

Wu, J., P. Capelli, J. Bouvier, M. Goulding, S. Arber and G. Fortin (2017). "A V0 core neuronal circuit for inspiration." Nat Commun 8(1): 544.

Zhang, X., C. T. Huang, J. Chen, M. T. Pankratz, J. Xi, J. Li, Y. Yang, T. M. Lavaute, X. J. Li, M. Ayala, G. I. Bondarenko, Z. W. Du, Y. Jin, T. G. Golos and S. C. Zhang (2010). "Pax6 is a human neuroectoderm cell fate determinant." Cell Stem Cell 7(1): 90-100.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method of generating a three-dimensional organoid comprising a population of hindbrain cells comprising a heterogeneous population of interneurons, the method comprising:

a) treating a population of mammalian pluripotent stem cells (PSCs) in vitro with a Wingless-Int (WNT) signaling pathway activator;

b) culturing the cells of a) in a first neural induction medium comprising a retinoic acid signaling pathway activator; and c) culturing the cells of b) in a second neural induction medium comprising the retinoic acid signaling pathway activator, a sonic hedgehog (Shh) signaling pathway activator; and a Notch signaling pathway inhibitor;

wherein the culturing results in generation of the population of hindbrain cells comprising the heterogeneous population of interneurons, wherein the heterogeneous population of interneurons comprises V2a interneurons, V0 interneurons, chemosensing interneurons, or a combination thereof, and generation of the three-dimensional organoid, wherein said culturing the population of PSCs is performed on a three-dimensional substrate or a pyramidal mold.

2. The method of claim 1, wherein the retinoic acid signaling pathway activator comprises a retinoic acid receptor agonist, the Shh signaling pathway activator comprises a Smoothened agonist, the Notch signaling pathway inhibitor comprises an inhibitor of Notch receptor activation, or a combination thereof.

3. The method of claim 1, wherein one or more of the retinoic acid signaling pathway activator, or the Shh signaling pathway activator is present in the neural induction medium at a concentration of from about 1 nM to about 2 μM.

4. The method of claim 1, wherein the Shh signaling pathway activator is present in the neural induction medium at a concentration of from about 30 nM to about 100 nM thereby enriching the heterogeneous population of interneurons for V0 interneurons.

5. The method of claim 4, wherein the heterogeneous population of interneurons is enriched for PHOX2A+ and PHOX2B+ chemosensing interneurons.

6. The method of claim 1, wherein the Shh signaling pathway activator is present in the neural induction medium at a concentration of about 1 μM thereby enriching and the heterogeneous population of interneurons for V2a interneurons.

7. The method of claim 1, wherein the Notch signaling pathway inhibitor is present in the neural induction medium at a concentration of about 250 nM to about 10 AM.

8. The method of claim 1, wherein the neural induction medium further comprises one or more SMAD signaling pathway inhibitors.

9. The method of claim 1, wherein the WNT signaling pathway activator is a GSK3 inhibitor.

10. The method of claim 1, wherein the WNT signaling pathway activator is selected from the group consisting of CHIR99021, WAY-316606, IQ1, QS11, SB-216763, BIO, and DCA.

11. The method of claim 1, wherein the culturing further comprises contacting the population of PSCs with a third neural induction medium comprising the retinoic acid signaling pathway activator, the Shh signaling pathway activator, and the Notch signaling pathway inhibitor.

12. The method of claim 1, wherein the first neural induction medium further comprises one or more Notch signaling pathway inhibitors, one or more SMAD signaling pathway inhibitors, or a combination thereof.

13. The method of claim 1, wherein c) is performed about two days after b).

14. The method of claim 1, wherein the cells are cultured for a period of 7 to 13 days after b).

15. The method of claim 11, wherein the second neural induction medium and the third neural induction medium do not comprise one or more SMAD signaling pathway inhibitors.

16. The method of claim 1, further comprising contacting the population of PSCs of a) with a ROCK inhibitor and one or more SMAD signaling pathway inhibitors prior to contact with the first neural induction medium of b).

17. The method of claim 1, wherein the population of PSCs is cultured on a cell culture substrate comprising a coating of extracellular matrix components.

18. The method of claim 1, wherein the population of PSCs are seeded on a cell culture substrate at a density of about 100,000 cells/cm$^2$ to about 200,000 cells/cm$^2$.

19. The method of claim 1, wherein the PSCs comprise embryonic stem cells (ESCs) or induced pluripotent stem cells (iPSCs).

20. The method of claim 1, wherein the PSCs are human H7 ESCs, H1 ESCs, WTC iPSCs, or WTB iPSCs.

21. The method of claim 1, wherein at least 10%, at least 20%, at least 30%, at least 40%, or at least 50% of the population of hindbrain cells comprising the heterogeneous population of interneurons are CHX10+ V2a interneurons, LHX5+ V0 interneurons, PHOX2A+ chemosensing interneurons, PHOX2B+ chemosensing interneurons, or a combination thereof.

22. The method of claim 1, wherein 20% to 40% of the population of hindbrain cells comprising the heterogeneous population of interneurons are CHX10+ V2a interneurons, LHX5+ V0 interneurons, or a combination thereof.

23. The method of claim 1, wherein 10% to 60% of the population of hindbrain cells comprising the heterogeneous population of interneurons are LHX5+ V0 interneurons, PHOX2A+ chemosensing interneurons, PHOX2B+ chemosensing interneurons, or a combination thereof.

24. The method of claim 1, wherein gene expression in the population of hindbrain cells comprising the heterogeneous population of interneurons is increased, compared to the population of PSCs, for one or more genes selected from: PHOX2A, PHOX2B, ADCYAP1, CHX10, SOX14, IRX3, LHX5, PAX2, MAB21L2, SOX21, EVX1, and EVX2.

25. The method of claim 1, wherein gene expression in the chemosensing interneurons is increased compared to the population of PSCs for one or more genes selected from: PHOX2A, PHOX2B, and ADCYAP1.

26. The method of claim 1, wherein gene expression in the V2a interneurons is increased compared to the population of PSCs for one or more genes selected from: CHX10, SOX14, and IRX3.

27. The method of claim 1, wherein gene expression in the V0 interneurons is increased compared to the population of PSCs for one or more genes selected from: LHX5, PAX2, MAB21L2, EVX1, and EVX2.

28. The method of claim 1, further comprising:

reseeding at least some of the population of hindbrain cells comprising the heterogeneous population of interneurons onto a neural maturation substrate; and culturing the seeded population of hindbrain cells comprising the heterogeneous population of interneurons in a neural maturation medium, thereby generating a mature population of hindbrain cells comprising the heterogeneous population of interneurons.

29. The method of claim 1, wherein the heterogeneous population of interneurons of the mature population is electrically excitable.

30. The method of claim 1, wherein the neural induction medium further comprises a ROCK inhibitor.

31. The method of claim 1, wherein the population of hindbrain cells is a population of respiratory hindbrain cells.

32. The method of claim 1, wherein the three-dimensional organoid comprises a diameter of about 100 μm to about 1000 μm.

33. The method of claim 1, wherein the three-dimensional organoid comprises a diameter of about 500 μm to about 700 μm.

* * * * *